(12) United States Patent
Singh et al.

(10) Patent No.: US 7,279,585 B2
(45) Date of Patent: Oct. 9, 2007

(54) LIPOPHILIC ELECTROPHORETIC PROBES

(75) Inventors: Sharat Singh, San Jose, CA (US); Hasan Tahir, Foster City, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 566 days.

(21) Appl. No.: 10/618,956

(22) Filed: Jul. 14, 2003

(65) Prior Publication Data

US 2004/0022843 A1 Feb. 5, 2004

Related U.S. Application Data

(60) Provisional application No. 60/441,034, filed on Jan. 17, 2003, provisional application No. 60/399,047, filed on Jul. 26, 2002.

(51) Int. Cl.
*C07D 311/82* (2006.01)
(52) U.S. Cl. .................................................. 549/223
(58) Field of Classification Search ................ 548/224; 549/224, 223
See application file for complete search history.

(56) References Cited

U.S. PATENT DOCUMENTS

| | | | | |
|---|---|---|---|---|
| 4,331,590 A | 5/1982 | Bocuslaski | | 260/112 B |
| 4,444,879 A | 4/1984 | Foster | | 435/7 |
| 4,650,750 A | 3/1987 | Giese | | 435/7 |
| 4,780,421 A | 10/1988 | Kameda | | 437/518 |
| 5,208,148 A | 5/1993 | Haugland | | 435/14 |
| 5,340,716 A | 8/1994 | Ullman | | 435/6 |
| 5,360,819 A | 11/1994 | Giese | | 514/538 |
| 5,516,636 A | 5/1996 | McCapra | | 435/6 |
| 5,516,931 A | 5/1996 | Giese | | 560/59 |
| 5,532,171 A | 7/1996 | Motsenbocker | | 436/533 |
| 5,602,273 A | 2/1997 | Giese | | 560/60 |
| 5,604,104 A | 2/1997 | Giese | | 435/7.1 |
| 5,610,020 A | 3/1997 | Giese | | 435/7.1 |
| 5,622,929 A | 4/1997 | Willner | | 514/8 |
| 5,650,270 A | 7/1997 | Giese | | 435/6 |
| 5,705,622 A | 1/1998 | McCapra | | 536/23.1 |
| 5,763,263 A | 6/1998 | Dehlinger | | 435/287 |
| 5,800,999 A | 9/1998 | Bronstein | | 435/6 |
| 5,807,675 A | 9/1998 | Davalian | | 435/6 |
| 5,843,666 A | 12/1998 | Akhavan-Taft | | 435/6 |
| 5,898,005 A | 4/1999 | Singh | | 436/527 |
| 6,027,890 A | 2/2000 | Ness | | 435/6 |
| 6,194,213 B1 | 2/2001 | Barbera-Guillem | | 435/968 |
| 6,235,520 B1 | 5/2001 | Malin | | 435/287 |
| 6,251,581 B1 | 6/2001 | Ullman | | 435/4 |
| 6,375,930 B2 | 4/2002 | Young | | 424/9.362 |
| 2002/0006378 A1 | 1/2002 | Young | | 424/111 |

FOREIGN PATENT DOCUMENTS

WO WO95/27204 10/1995

OTHER PUBLICATIONS

Nampalli, S. "Fluorescence Resonance Energy Transfer Dye Nucleotide Terminators: A New Synthetic.Approach for High-Throughput DNA Sequencing", Nucleosides, Nucleotides & Nucleic Acids, 20(4-7), 361-7 (2001).*

Boose et al, "Principles of AlphaScreen Amplified Luminescent Proximity Homogeneous Assay", AlphaScreen Technology, Application Note ASC-001, Packard Bioscience, BioSignal Package Inc.

Giese, "Electrophoric Release Tags: Ultra sensitive Molecular Labels Providing Multiplicity", Trends in Analytical Chemistry, vol. 2, No. 7, 1983, pp. 166-168.

Lum et al, "Ability of Specific Monoclonal Antibodies and Conventional Antisera Conjugated to Hematoporphyrin to Label and Kill Selected Cell Lines Subsequent to Light Activation", Cancer Research vol. 45, 1985, pp. 4380-4386.

Oseroff et al, "Antibody-Targeted Photolysis: Selective Photodestruction of Human T-Cell Leukemia Cells using Monoclonal Antibody-Chlorin $e_6$ Conjugates", Proc. Natl. Acad. Sci USA, vol. 83, 1986, pp. 8744-8748.

Rakestraw et al., "Antibody-Targeted Photolysis: In vitro Studies with SN(IV) Chlorin $e_6$ Covalently Bound to Monoclonal Antibodies Using a Modified Dextran Carrier" Proc. Natl Acad Sci USA,, vol. 87, 1990, pp. 4217-4221.

Strong et al., "Antibody-Targeted Photolysis" Annals New York Academy of Sciences, vol. 745, 1994, pp. 297-320.

Ulman, Edwin F. et al., Luminescent oxygen channeling immunoassay: Measurement of particle binding kinetics by chemiluninescence Proc. Atl. Acad. Sci. USA, vol. 91, Jun. 1994, pp. 5426-5430.

Yarmush et al., "Antibody Targeted Photolysis", Critical Reviews in Therapeutic Drug Carrier Systems, vol. 10, 1993, pp. 197-252.

Yermul et al, "Selective Killing of lymphocytes by Phototoxic Liposomes", Proc. Natl. Acad. Sci. USA, vol. 84, 1987, pp. 246-250.

Beaudet et al, "Homogeneous Assays for Single-Nucleotide Polymorphism Typing Using AlphaScreen", Genome research, II:600-608, 2001.

BioSignal, "Whole Cell Camp Functional Assay", AlphScreen, Technical Note AN002-Asc, Packard Instrument Company.

Baldwin et al., Synthesis of a Small Molecule Combinatorial Library Encoded with Molecular Tags. Journal of American Chemical Society, (1995) vol. 117, pp. 5588-5589.

Database CAPLUS on ACS, AN: (1997), vol. 42, No. 20-22, pp. 3137-3145.

(Continued)

*Primary Examiner*—Rebecca Anderson
*Assistant Examiner*—Michael P. Barker
(74) *Attorney, Agent, or Firm*—Fenwick & West LLP

(57) ABSTRACT

Compounds, compositions, and methods for labeling membranes are disclosed. Compounds of formula G-L-E are described wherein G is a lipophilic group, L is a cleavable linkage and E is an electrophoretic group. The compounds become associated with membranes, and can be cleaved with a cleavage-inducing moiety thereby releasing the detectable electrophoretic group.

13 Claims, 17 Drawing Sheets

OTHER PUBLICATIONS

Geysen et al., Isostope or Mass Encoding of Combinatorial Libraries. Chemistry & Biology, (Aug. 1996), vol. 3, No. 8, pp. 679-688.

Taga et al, Capillary Electrophoretic Determination of the Association Constant of a Protein and a Neutral Carbohydrate by Introducing Mercaptoanesulfonate Tags to the Carbohydrate, Journal of Chromatogrpahy A, (Apr. 16, 1999), vol. 839, No. 1-2, pp. 157-166.

Bayer et al., "On the Mode of Liposome-Cell Interactions Biotin-Conjugated Lipids as Ultrastructural Probes" Biochimica et Biophysica Acto, 550 (1979), pp. 464-473 © Elsevier/North-Holland Boimedical Press.

Barinaga-Rementeria Ramirez et al., "Affinity Partitioning for Membrane Purifcation Exploiting the Biotin-NeutrAvidin Interaction: Model Study of Mixed Liposomes and Membranes", Journal of Chromatography A, 971 (2002) 117-127.

Plant et al., "Generic Liposomes Reagent for Immunoassays", Annalytical Biochemistry 176, pp. 420-426 (1989).

Davenport "Fluorescence Probes for Studying membrand heterogeneity" Methods in Enzymology, vol. 278 (1997) pp. 487-512.

Edidin "Fluorescent Labeling of Cell Surfaces" Methods in Cell Biology, vol. 29 (1989) pp. 87-101.

* cited by examiner

Thiazole cleavable linkage

Oxazole cleavable linkage

Olefin cleavable linkage

Thioether cleavable linkage

Pro28-amide

Pro29-amide

Pro33-amide

Pro34-amide

Pro35-amide

Pro36-amide

Pro36-amide

LIPOPHILIC ELECTROPHORETIC PROBES

This patent application claims priority from U.S. provisional applications Ser. No. 60/399,047 filed Jul. 26, 2002 and 60/441,034 filed 17 Jan. 2003, both of which are incorporated herein by reference in their entirety.

TECHNICAL FIELD

The present invention pertains to compositions, formulations and methods for labeling membranes.

BACKGROUND OF THE INVENTION

Determination of the binding behavior of cell membrane receptor proteins toward natural or artificial ligands is important for many biological and medical studies. In the field of target or drug discovery, high throughput screening efforts are key to isolating target-specific binders, agonists, or antagonists. Many of these therapeutic or diagnostic targets are cell surface antigens that, upon recognition by natural or synthetic binding molecules, trigger a network of signal transduction and gene regulation events inside the cell that result in cellular responses important in the initiation or maintenance of a disease. Target antigens may also differentially reside on the surface of cells and signify a unique state of physiology or disease progress in the tissue or organ. In researching these cell surface targets, the isolation of target-specific binders provides an invaluable tool for detection and perturbation at the molecular level.

Assays for cell surface receptors have normally been based on a ligand-receptor interaction in which the ligand is labeled and the amount of labeled ligand bound to the receptor is measured. Types of assays include screening for monolconal antibodies against biomarkers and therapeutic targets specific for diseased cells that are not found on normal cells, and screening for ligands or pharmacological agents specific for surface antigens that are endogenously expressed or over-expressed as recombinant proteins on different cell lines. Such assays often involve complicated procedures of separating the receptor proteins to be assayed from cellular material and therefore cannot be done in realtime. Further, it may be necessary to label several kinds of ligands or receptors, because receptors are normally specific to only one antigenic determinant.

WO 01/42489 describes a method for fluorescence detection of lipid membranes using lipophilic functionalized nanocrystals to label the membranes. The labeled membranes are then exposed to an excitation light source, and fluorescence emitted from the excited nanocrystals is detected. In a photodynamic therapy method of U.S. Pat. No. 6,375,930, a photosensitive texaphyrin is conjugated to estradiol or cholesterol. Red blood cells or white blood cells, are then loaded with the conjugates. The complex, upon exposure to light, ruptures depositing its contents.

However, there are several drawbacks to using fluorescent substrates for the analysis of cells. For example, it is difficult to get the substrate through the outer cell membrane without disrupting the cell. Moreover, there is the problem of cell leakage. Thus, following enzymatic hydrolysis of fluorescein di-62-galactopyranoside, the resulting fluorescein rapidly leaks out of the cell, with a half life of about 10 minutes. There remains a need, therefore, for compositions and methods for labeling membranes.

SUMMARY OF THE INVENTION

In one aspect, the invention pertains to a compound of formula:

$$G\text{-}(L\text{-}E)_m$$

wherein G is a lipophilic moiety capable of incorporating into a lipid membrane; L is a cleavable linker; E is an electrophoretic tag; and m is an integer greater than 1 and less than 100.

Another aspect of the invention pertains to compound of formula:

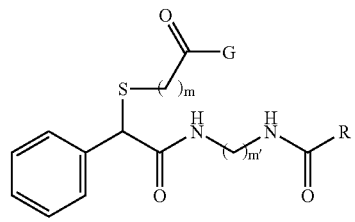

wherein G is a lipophilic moiety capable of incorporating into a lipid membrane; R comprises a detectable moiety; and m and m' are integers independently chosen from 1 to 10. In certain aspects, the lipophilic moiety (G) has the formula:

$$X\text{—}((CH_2)_n\text{—}CH_3)_{n'}$$

wherein X is a direct bond, O, S, or N: n is an integer between 5 and 25; and n' is 1 or 2.

Yet another aspect of the invention pertains to a mixture comprising a plurality of compounds having the formula:

$$G\text{-}(L\text{-}E)_m$$

wherein G is a lipophilic moiety capable of incorporating into a lipid membrane; L is a cleavable linker; E is an electrophoretic tag; m is an integer greater than 1 and less than 100; and wherein E of each compound of the plurality is individually detectable.

Another aspect of the invention pertains to lipid membranes labeled with compounds of formula:

$$G\text{-}(L\text{-}E)_m$$

wherein G is a lipophilic moiety capable of incorporating into a lipid membrane; L is a cleavable linker; E is an electrophoretic tag; and m is an integer greater than 1 and less than 100.

Another aspect of the invention pertains to the internalization of the G-L-E or G-(L-E)$_m$ compounds of the invention. In one aspect, the compounds are incorporated into the lipid bilayer, such as the cellular membrane of an intact cell. The cell, thus labeled, can then be exposed to a ligand, such as an agonist or an antagonist. The interaction of the ligand with the receptor on the cell induces the internalization of the lipophilic compounds of the invention. The electrophoretic tags on the surface of the cell can be released by cleavage of the cleavable linker, and the amount of released electrophoretic tags can be compared to controls. The effect of different ligands can thus be quantified.

In another aspect, compounds of the invention defined generally by the formula G-(L-E)$_m$ include lipophilic moieties that are bound to cleavable linkages and electrophoretic tags by way of a capture moiety and a capture agent, such as a biotin and avidin. Preferably, such compounds of the invention are defined by the formula:

$$G\text{-}(b_1)(b_2)\text{-}(L\text{-}E)_m$$

wherein G, L, E, and m are as defined above, and $b_1$ is a capture moiety and $b_2$ is its corresponding capture agent.

That is, $b_1$ and $b_2$ are moieties that form a strong non-covalent linkage between lipophilic moiety, G, and the cleavable linkages, L, and electrophoretic tags, E. Compounds of this embodiment may be conveniently produced in modular form. For example, compounds of the form, G-$b_1$, may be used with many different cells or membranes, and compounds of the form, $b_2$-(L-E)$_m$, may be added to provide specific labels. In one aspect, compositions of the invention include a plurality, or set, of compounds of the form $b_2$-(L-E)$_m$ together with one or more compounds of the form, G-$b_1$.

These and other aspects of the present invention will become evident upon reference to the following detailed description and attached drawings. In addition, various references are set forth herein which describe in more detail certain procedures or compositions, and are therefore incorporated by reference in their entireties.

DETAILED DESCRIPTION OF THE INVENTION

Figure 1A:
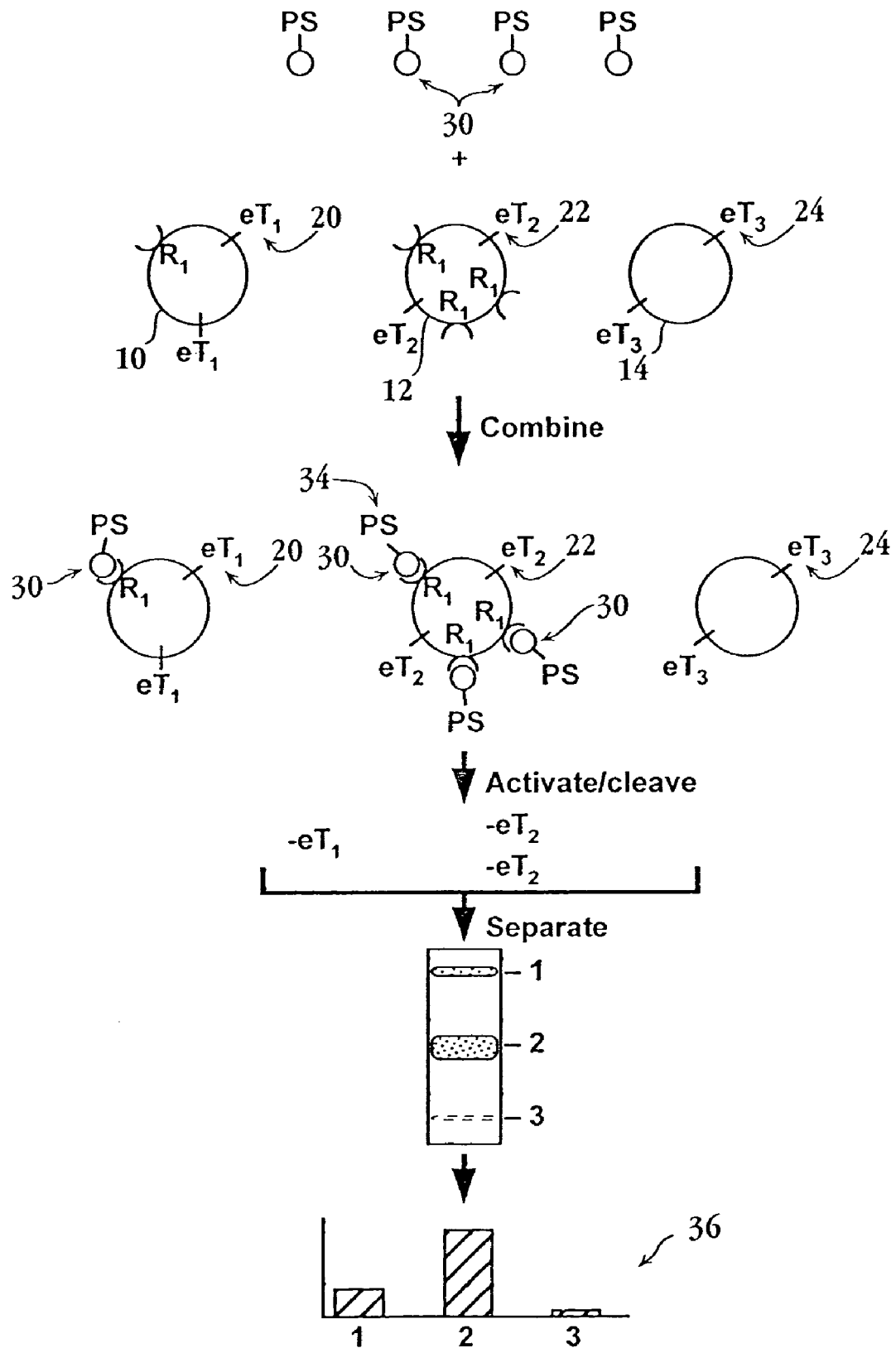
FIG. 1A illustrates a homogeneous assay format employing compounds of the invention.

Unless otherwise defined below, the terms used herein have their normally accepted scientific meanings. Definition of standard chemistry terms may be found in reference works, including Carey and Sundberg (1992) "Advanced Organic Chemistry 3$^{rd}$ Ed." Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art. Such techniques are explained fully in the literature. See, for example, G. Barany and R. B. Merrifield (1980) "The Peptides: Analysis, Synthesis, Biology" Vol. 2, E. Gross and J. Meienhoffer, eds. Academic Press, New York., *Methods In Enzymology* (S. Colowick and N. Kaplan eds., Academic Press, Inc.); *Remington's Pharmaceutical Sciences,* 18th Edition (Easton, Pa.: Mack Publishing Company, 1990).

All publications, patents and patent applications cited herein, whether supra or infra, are hereby incorporated by reference in their entirety.

It must be noted that, as used in this specification and the appended claims, the singular forms "a," "an," and "the" include plural referents unless the content clearly dictates otherwise. Thus, for example, reference to "an oligonucleotide" includes a mixture of two or more oligonucleotides, and the like.

I. Definitions

In describing the present invention, the following terms will be employed, and are intended to be defined as indicated below.

The term "alkyl" as used herein refers to a straight, branched, or cyclic hydrocarbon chain fragment or radical containing between about one and about fifty carbon atoms, more preferably between about one and about twenty carbon atoms (e.g., methyl, ethyl, n-propyl, iso-propyl, cyclopropyl, n-butyl, iso-butyl, tert-butyl, cyclobutyl, adamantyl, noradamantyl and the like). Straight, branched, or cyclic hydrocarbon chains having eight or fewer carbon atoms will also be referred to herein as "loweralkyl". The hydrocarbon chains may further include one or more degrees of unsaturation, i.e., one or more double or triple bonds (e.g., vinyl, propargyl, allyl, 2-buten-1-yl, 2-cyclopenten-1-yl, 1,3-cyclohexadien-1-yl, 3-cyclohexen-1-yl and the like). Alkyl groups containing double bonds such as just described will also be referred to herein as "alkenes". Similarly, alkyl groups having triple bonds will also be referred to herein as "alkynes". However, as used in context with respect to cyclic alkyl groups, the combinations of double and/or triple bonds do not include those bonding arrangements that render the cyclic hydrocarbon chain aromatic.

Representative examples of alkanes useful as alkyl group substituents of the present invention include methane, ethane, straight-chain, branched or cyclic isomers of propane, butane, pentane, hexane, heptane, octane, nonane and decane, with methane, ethane and propane being preferred. Alkyl groups having up to about thirty, or up to about fifty carbon atoms are contemplated in the present invention. Representative examples of substituted alkyls include alkyls substituted by two or more functional groups as described herein.

Representative examples of alkenes useful as alkenyl group substituents include ethene, straight-chain, branched or cyclic isomers of propene, butene, pentene, hexene, heptene, octene, nonejne and decene, with ethene and propene being preferred. Alkenyl groups having up to about thirty or fifty carbon atoms, and up to about five double bonds, or more preferably, up to about three double bonds are contemplated in the present invention.

Representative examples of alkynes useful as alkynyl group substituents include ethyne, straight-chain, branched or cyclic isomers of propyne, butyne, pentyne, hexyne, heptyne, octyne, nonyne and decyne, with ethyne and propyne being preferred. Alkynyl groups having up to about thirty, or up to about fifty carbon atoms, and having up to about five or up to about three triple bonds are contemplated in the present invention.

The term "halo" or "halogen" as used herein refers to the substituents fluoro, bromo, chloro, and iodo.

The term "carbonyl" as used herein refers to the functional group —C(O)—. However, it will be appreciated that this group may be replaced with well-known groups that have similar electronic and/or steric character, such as thiocarbonyl (—C(S)—); sulfinyl (—S(O)—); sulfonyl (—SO$_2$—); phosphonyl (—PO$_2$—), and methine. Other carbonyl equivalents will be familiar to those having skill in organic chemistry.

The term "aryl" as used herein refers to cyclic aromatic hydrocarbon chains having twenty or fewer carbon atoms, e.g., phenyl, naphthyl, biphenyl and anthryl. One or more carbon atoms of the aryl group may also be substituted with, e.g.: alkyl; aryl; heterocycle; halogen; nitro; cyano; hydroxyl, alkoxyl or aryloxyl; thio or mercapto, alkyl- or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylocarbonyl; iminyl, or aryl- or alkyliminyl; sulfo; alkyl- or arylsulfonyl; hydroximinyl, or aryl- or alkoximinyl; carbamido; or thiocarbamido. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heterocycleoxy, heteroaryloxy, and heteroaralkylthio) are defined by analogy to the above-described terms.

The aryl may be a compound whose molecules have the ring structure characteristic of benzene, naphthalene, phenanthrene, anthracene, and the like, i.e., the 6-carbon ring of benzene or the condensed 6-carbon rings of the other aromatic derivatives. For example, an aryl group may be phenyl or naphthyl, and the term as used herein includes both unsubstituted aryls and aryls substituted with one or more nitro, carboxy, sulfonic acid, hydroxy, oxyalkyl or halide substituents. In this case, the substituent on the phenyl or naphthyl may be added in a synthetic step after the condensation step which forms the macrocycle.

The term "aralkyl" as used herein refers to an aryl group that is joined to a parent structure by an alkyl group as described above, e.g., benzyl, α-methylbenzyl, phenethyl, and the like.

The term "heterocycle" as used herein refers to a cyclic alkyl group or aryl group as defined above in which one or more carbon atoms have been replaced by a non-carbon atom, especially nitrogen, oxygen, or sulfur. Non-aromatic heterocycles will also be referred to herein as "cyclic heteroalkyl". Aromatic heterocycles are also referred to herein as "heteroaryl". For example, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridazinyl, triazinyl, piperidinyl, morpholinyl, thiomorpholinyl, pyrazinyl, piperazinyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pyridinyl, quinuclidinyl, carbazolyl, acridiniyl, phenazinyl, phenothiazinyl, phenoxazinyl, purinyl, benzimidazolyl, benzthiazolyl, and benzoxazolyl.

A "protein" or a "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein. Full-length proteins, analogs, and fragments thereof are encompassed by the definition. The terms also include postexpression modifications of the polypeptide, for example, glycosylation, acetylation, phosphorylation and the like. Furthermore, as ionizable amino and carboxyl groups are present in the molecule, a particular polypeptide may be obtained as an acidic or basic salt, or in neutral form.

A polypeptide may be obtained directly from the source organism, or may be recombinantly or synthetically produced.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in a desired detectable range.

As used herein, a "solid support" refers to a solid surface such as a magnetic bead, latex bead, microtiter plate well, glass plate, nylon, agarose, acrylamide, and the like.

"Liposome" refers to a generally spherical cluster or aggregate of amphiphilic compounds, typically in the form of one or more concentric layers, for example, bilayers. The liposomes may be formulated, for example, from the phosphorus or silicon amphiphilic or conventional amphiphilic compounds, including lipids, such as ionic and/or non-ionic lipids, and/or a combination phosphorus and/or silicon amphiphilic compounds and conventional amphiphilic compounds.

"Micelle" refers to colloidal entities formulated from amphiphilic compounds, including the phosphorus or silicon amphiphilic compounds, as well as conventional lipids. Micelles may comprise a monolayer, hexagonal H2 phase configuration or a bilayer configuration.

"Antibody" means an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular polypeptide is maintained.

"Antibody binding composition" means a molecule or a complex of molecules that comprise one or more antibodies and derives its binding specificity from an antibody. Antibody binding compositions include, but are not limited to, antibody pairs in which a first antibody binds specifically to a target molecule and a second antibody binds specifically to a constant region of the first antibody; a biotinylated antibody that binds specifically to a target molecule and strepavidin derivatized with moieties such as electrophoretic tags or photosensitizers; antibodies specific for a target molecule and conjugated to a polymer, such as dextran, which, in turn, is derivatized with moieties such as electrophoretic tags or photosensitizers; antibodies specific for a target molecule and conjugated to a bead, or microbead, or other solid phase support, which, in turn, is derivatized with moieties such as electrophoretic tags or photosensitizers, or polymers containing the latter.

"Capillary electrophoresis" means electrophoresis in a capillary tube or in a capillary plate, where the diameter of the separation column or thickness of the separation plate is between about 25-500 microns, allowing efficient heat dissipation throughout the separation medium, with consequently low thermal convection within the medium.

A "sieving matrix" or "sieving medium" means an electrophoresis medium that contains crosslinked or non-crosslinked polymers which are effective to retard electrophoretic migration of charged species through the matrix.

"Specific" in reference to the binding of two molecules or a molecule and a complex of molecules refers to the specific recognition of one for the other and the formation of a stable complex as compared to substantially less recognition of other molecules and the lack of formation of stable complexes with such other molecules. Preferably, "specific" in reference to binding means that to the extent that a molecule forms complexes with other molecules or complexes, it forms at least fifty percent of the complexes with the molecule or complex for which it has specificity. Generally, the molecules or complexes have areas on their surfaces or in cavities giving rise to specific recognition between the two molecules. Exemplary of specific binding are antibody-antigen interactions, enzyme-substrate interactions, polynucleotide hybridizations and/or formation of duplexes, cellular receptor-ligand interactions, and so forth.

As used herein, the term "spectrally resolvable" in reference to a plurality of fluorescent labels means that the fluorescent emission bands of the labels are sufficiently distinct, i.e. Sufficiently non-overlapping, that electrophoretic tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558, 4,811,218, or the like, or in Wheeless et al, pgs. 21-76, in Flow Cytometry: Instrumentation and Data Analysis (Academic Press, New York, 1985).

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

In one aspect, the compounds of the invention comprise the formula $G-(L-E)_m$. The compounds comprise a lipophilic group (G), a cleavable linkage (L) and an electrophoretic group (E). Each lipophilic group can have one L-E attached to it or can have several L-E moieties attached to it, where m can be between 1 and 1000, preferably between 1 and 100, and more preferably between 1 and 10. In compounds where more than 1 electrophoretic group is present, E can be the same or can be different such that each E is capable of being individually detected. Preferably, whenever more than one electrophoretic groups, E, are present on a single lipophilic group, each electrophoretic group is the same.

Compositions and compounds of the invention may be used for labeling membranes, such as cellular membranes and liposomes. In such uses, after forming a membrane labeled with one or more electrophoretic tags, a cleavage-inducing moiety is brought into close proximity with cleavable linkages on the compounds of the invention such that the electrophoretic tags are released and detected. The methods may be practiced in either a homogeneous or a non-homogeneous format, as illustrated in FIGS. 1A and 1B.

Figure 1B:
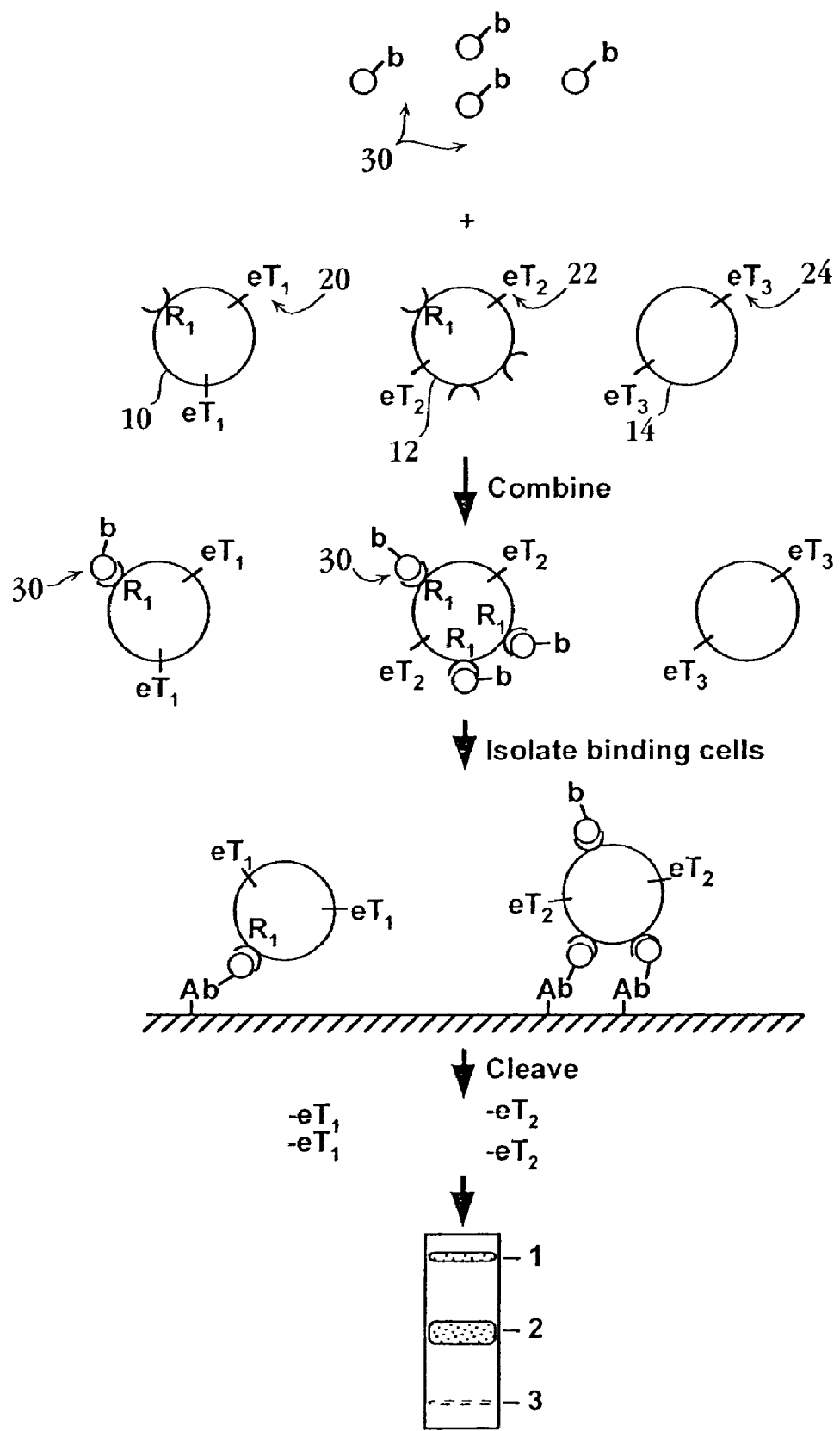
FIG. 1B illustrates a non-homogeneous assay format employing compounds of the invention.

FIG. 1A illustrates an exemplary method for using compositions of the invention to determine the cell surface binding affinity of a test compound among a plurality of cell types. FIG. 1A shows a plurality of cells 10, 12, 14 of different cell types. Each cell may or may not contain a surface moiety recognized by the test compound, such as receptor $R_1$ in the Figure. Each cell type is labeled with a cell-specific electrophoretic probe of the invention 20, 22, 24 (also designated $eT_1$, $eT_2$, $eT_3$). The lipophilic anchor moieties of the probes can be incorporated into the cell membrane by incubation for about an hour at 37° C./5% $CO_2$. Preferably, the cells are then chilled, e.g. 4° C., for the binding assay. At these low temperatures, leaching of incorporated lipophilic probes from the cell surface into the extracellular environment is minimized, and cross-labeling of different cell populations with different probes is avoided.

With continued reference to FIG. 1A, the mixture of cells is incubated, e.g. at 4° C. for one hour, with a test compound 30. In the embodiment of FIG. 1A, where the assay is carried out in a homogeneous format, each test compound is conjugated, directly or indirectly, to a cleavage-inducing group (designated as "PS" in the figure).

The cleavage-inducing group may be linked directly to the test compound, or it may be linked to a secondary compound which binds to the test compound, e.g. a secondary antibody effective to bind to any test MAB. Alternatively, the test compound, or the secondary antibody, may be labeled with biotin, in which case the mixture can be incubated with streptavidin-conjugated photosensitizer.

The cleavage-inducing group is effective to cleave the linkages of electrophoretic probes on cells only within a limited proximity, effectively on the same cell as the bound compound. An example is a sensitizer group (indicated by 34) that is capable of generating a short-lived active chemical species, such as singlet oxygen, under selected activation conditions, e.g., photoillumination. Accordingly, activation of photosensitizer (PS) groups in such an assay mixture will cleave electrophoretic probes only if the probes are in close proximity to said photosensitizer group; that is, on the same cell surface to which a test compound is bound.

As can be appreciated from FIG. 1A, binding of test compound to a cell places the conjugated sensitizer group in proximity with the cleavable linker of the electrophoretic probe anchored to the cell surface. The cell mixture is then treated to activate the cleaving groups, i.e. illuminated to active photosensitizers (e.g. at 640-800 nm for a phthalocyanine sensitizer), generating singlet oxygen in the proximity of the bound sensitizer groups. The singlet oxygen is sufficiently short-lived that only surface-bound sensitizer, as opposed to any unbound, solution-phase sensitizer, is effective to cleave electrophoretic probes bound to cells. The reaction thus selectively cleaves the electrophoretic probes on cells to which the test compound is bound, such as probes 20 and 22 in FIG. 1A, releasing the specific "tags" from the probes labeling these cell types.

The released tags are then separated and analyzed, preferably by electrophoresis. The separated peaks are detected, e.g. by fluorescence emission detection of fluorescent labels in the tags. Because the separation characteristics of the eTags released from the respective cells are known, the multiplex data output, shown schematically at 36 in FIG. 1A, can be used to identify the cell samples to which the test compound binds. Intensity of peaks can also be used to determine the relative extent of binding of the test compound to different cells, if the test compound binds to more than one cell.

Preferably, the labels employed in the electrophoretic tags are such that peak height or area of different tags can be directly correlated to the number of tags detected. For example, a set of probes may employ the same label and different mobility modifying groups, as discussed further below.

A known amount of a "standard" eTag may be added to the test assay to provide a standard for calibrating the mobility and peak characteristics of the released tag(s). A positive control antibody (e.g. anti-HLA-A,B,C) can also be included, to ensure detection of release of different eTags from different cell samples. The measured peak height or area under the curve (AUC) of the standard eTag ($T_{std}$), relative to the known amount of standard eTag added, can be used to calculate the amount of test and control eTags from the measured peak heights or AUC in the electropherogram.

The assays may also be carried out in a heterogeneous format, as illustrated in FIG. 1B. Heterogeneous techniques normally involve a separation step, where cells having bound ligand are separated from other assay components, e.g. non-binding cells and unbound ligand. Homogeneous assays do not require, but may employ, a separation step. Separation can be achieved in a variety of ways, each employing a reagent bound to a solid support that distinguishes between binding and non-binding cells. The solid support may be a vessel wall, e.g., microtiter well plate well, capillary, plate, slide, beads, including magnetic beads, liposomes, or the like. The primary characteristics of the solid support are that it (1) permits segregation of the binding cells from non-binding cells and (2) does not interfere with the formation of the binding complex, nor the other operations of the determination.

The solid support may bind the cell-ligand complex directly or indirectly. For direct binding, the surface may be activated with various functionalities that will form covalent bonds with a test binding compound. For indirect binding, which is preferred, the surface noncovalently binds the test compound, or it binds an intermediate compound, such as biotin, which is linked to the test compound.

A heterogeneous assay is illustrated in FIG. 1B. After binding of the test compound to the differently labeled cell types, as above, the binding cells are separated from non-binding cells. This can be accomplished, for example, by employing test compounds linked to an affinity molecule, such as biotin, and capturing cells containing bound test compound on a surface containing a binding partner for the affinity molecule, such as streptavidin (as depicted in FIG. 1B).

The non-binding cells and/or unbound ligand are generally removed by washing the support. Where particles or beads are employed, these may be separated from the supernatant before washing, by filtration, centrifugation, magnetic separation, etc.

The captured cells are then treated, as above, to cleave the attached electrophoretic probes. In a this format, cleavage of the electrophoretic probes on binding cells need not be proximity dependent, since cells not having bound ligand have been removed. Therefore, a larger variety of cleavage protocols can be used. Cleavage may still employ a sensitizer, as described above, to cleave an oxidatively labile linkage, but it may also employ various types of chemical, photochemical, or enzymatic cleavage of a variety of cleavable linking groups, such as are known in the art. For example, non-limiting examples of chemically cleavable linkages include disulfides (cleavable by reduction, typically using dithiothreitol), azo groups (cleavable with dithionate), sulfones (cleavable with basic phosphate, with or without dithiothreitol), glycols, cleavable by periodate, and esters, cleavable by hydrolysis. Photolabile linkers include, for example, azo linkages and o-nitrobenzyl ethers.

After washing, the support may be combined with a solvent into which the e-tag reporters are to be released. Depending on the nature of the cleavable bond and the method of cleavage, the solvent may include any additional reagents for the cleavage. Where reagents for cleavage are not required, the solvent is conveniently an electrophoretic buffer. For example, where the cleavable linkage is photolabile, the medium may be irradiated with light of appropriate wavelength to release the e-tag reporters into the buffer.

If the cleavage reagent should interfere with electrophoretic analysis, it may be necessary to separate the e-tag reporters from the cleavage reagent solution. Depending on the nature of the e-tag reporters and the reagent, the e-tag reporters may be sequestered from the reagent by using ion exchange columns, liquid chromatography, an initial electrophoretic separation, and the like. Alternatively, a capture ligand can be bound to the e-tag moiety, to remove any interfering components in the mixture.

Following release of the electrophoretic tags from the probes, the tags are separated by electrophoresis and analyzed as above.

The Lipophilic Group (G)

In one aspect, the compounds of the invention comprise a lipophilic moiety or a lipopilic group (G). The lipophilic group is capable of binding to the membranes such that all or substantially all of the compounds of the invention are bound to the membranes rather than being free in solution. The lipophilic moiety or functionality thus imparts lipophilicity or lipid solubility which decreases the wettability of surfaces by water and the solubility in water of compounds to which it is bound. The lipophilic moiety (G) can contain 1 to 50 or more atoms, usually carbon atoms substituted with hydrogen or halogen and can include alkyl, alkylidene, aryl and aralkyl. The lipophilic group or functionality will normally have one to six straight or branched chain alkyl groups of at least 5 carbon atoms, more usually at least 10 carbon atoms, and preferably at least 15 carbon atoms, not more than 50 carbon atoms, more usually not more than 30 carbon atoms. The alkyl group will normally be terminal and may be bonded to rings of 5 or 6 members, which may be alicyclic, heterocyclic, or aromatic. The lipophilic moiety may additionally be bonded to photosensitizers or chemiluminescent compounds. Thus, the lipophilic group contains an alkyl group of formula $-(CH_2)_nCH_3$ where n is an integer between 1 and 50.

The precursors to the lipophilic moiety can be the alkyl compounds having a polar group that may be a single functionality or a complex group of functionalities at one of the hydrocarbon chains. The polar group can serve to attach G with the cleavable linkage moiety (L). The polar group can be an acyl group, particularly carboxy and phosphoryl esters, a hydroxylic group, which may be employed for forming an ether or ester link, an amino group, which may serve to provide an alkylamino, an amide, amidine, or urea link, or a mercaptan, which may serve to form a thioether group with an activated olefin, and the like. Thus, the lipophilic moiety is linked to the cleavable linkage moiety via an alkyl ($CH_2$), amide, sulfonamide, carboxyamide, carboxylate ester, urethane, urea, or thiourea. The lipohilic moiety can thus be chosen from the large variety of potential fatty acid components, such as, for example, myristic acid, palmitic acid, or stearic acid or a substituted or unsubstituted sphingosine.

sequence of a protein, utilizing the hydrophobic and hydrophilic properties of each of the 20 natural amino acids is described in Kyte et al. (1982) J. Mol. Biol. 157: 105-132

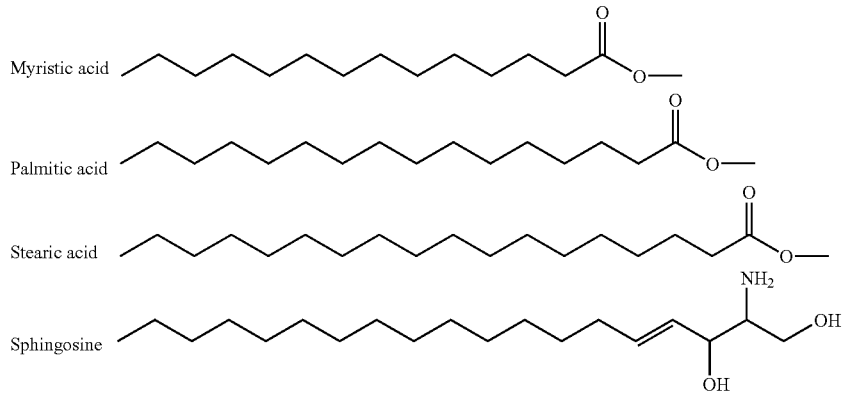

In another aspect, lipophilic moiety includes cholesterol; steroids including progestagens such as progesterone, glucocorticoids such as cortisol, mineralocorticoids such as aldosterone, androgens such as testosterone and androstenedione, and estrogens such as estrone and estradiol; glycolipids such as cerebroside, or ganglioside; molecules having isoprenoid side chains such as vitamin $K_2$, coenzyme $Q_{10}$, chlorophyll, or carotenoids; low density lipoprotein (LDL), and the like. Generally any sterol capable of attachment or which can be modified for attachment to the cleavable linkage (L) may be used in the practice of the present invention. For example, such sterols include but are not limited to cholesterol, vitamin D, phytosterols (including but not limited to sitosterol, campesterol, stigmasterol, and the like), steroid hormones, and the like.

Figure 2:
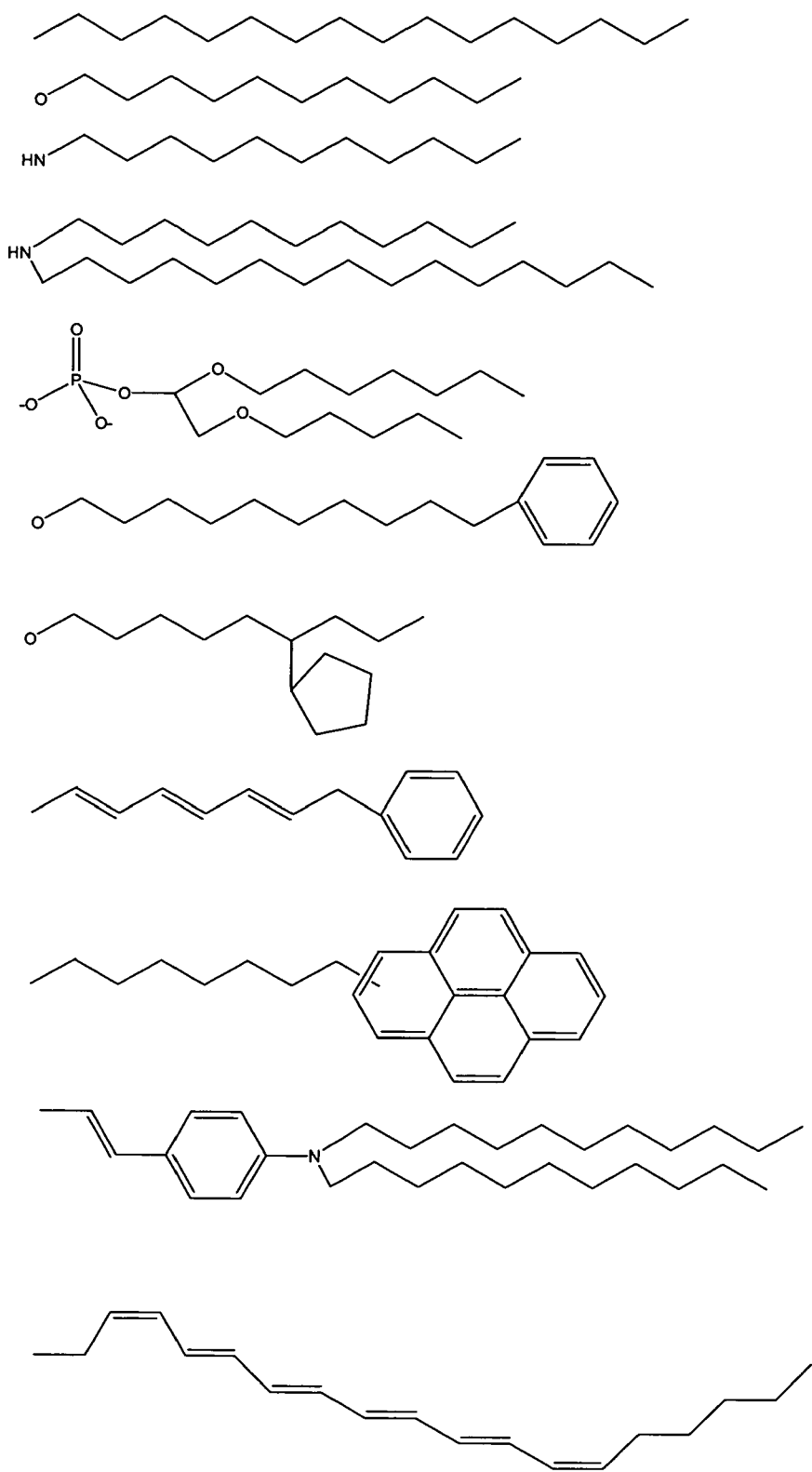
FIG. 2 depicts exemplary lipophilic groups.
Figure 3A:
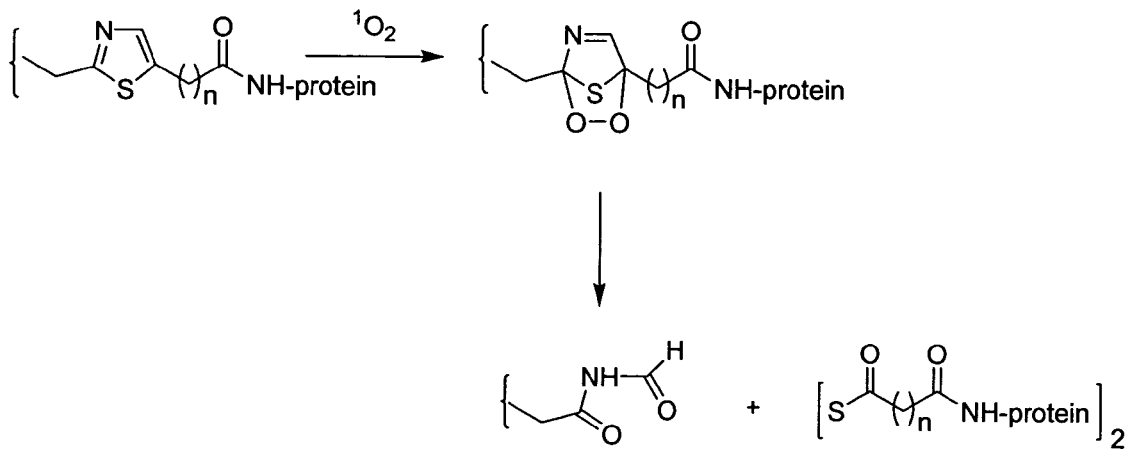
FIGS. 3A-3F illustrate oxidation-labile linkages and their respective cleavage reactions mediated by singlet oxygen.
Figure 3B:
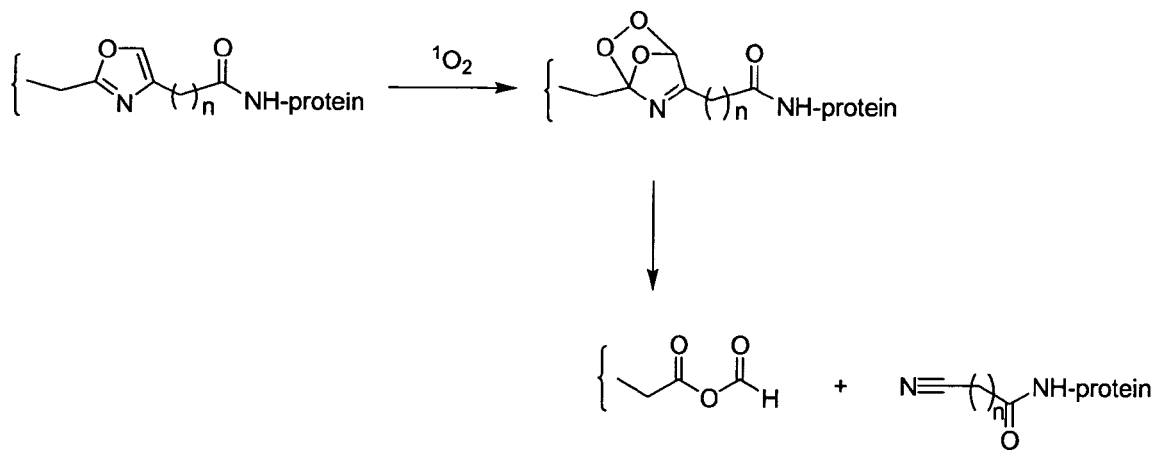
Figure 3C:
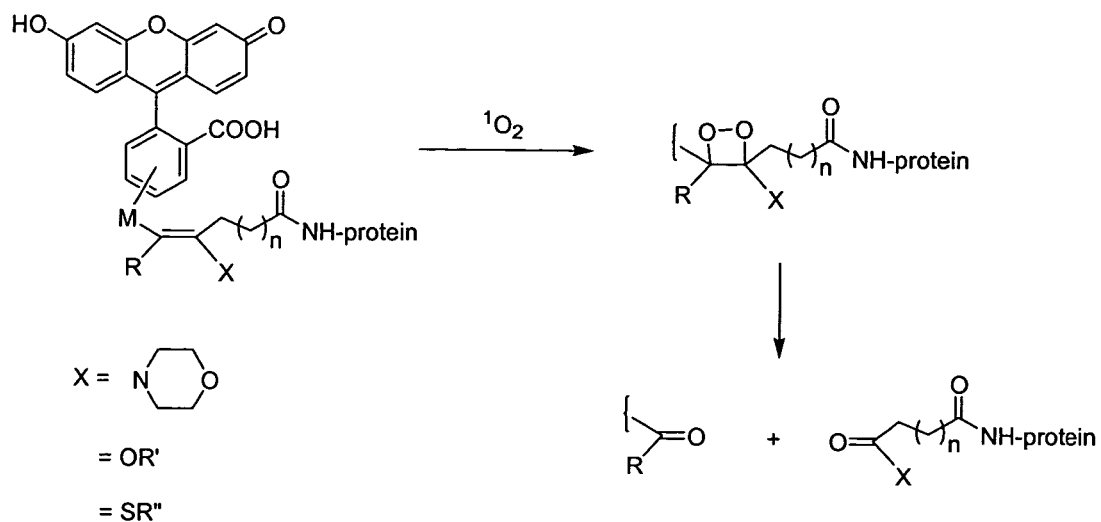
Figure 3D:
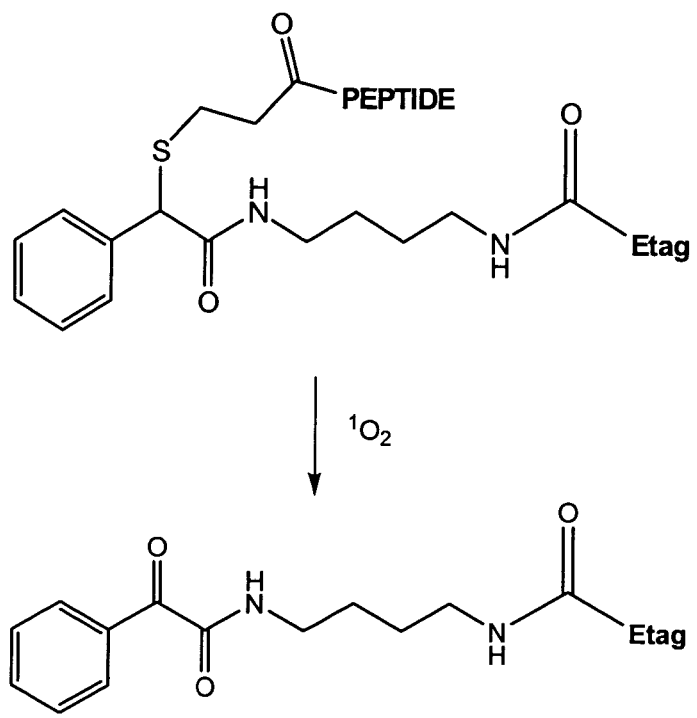
Figure 3E:
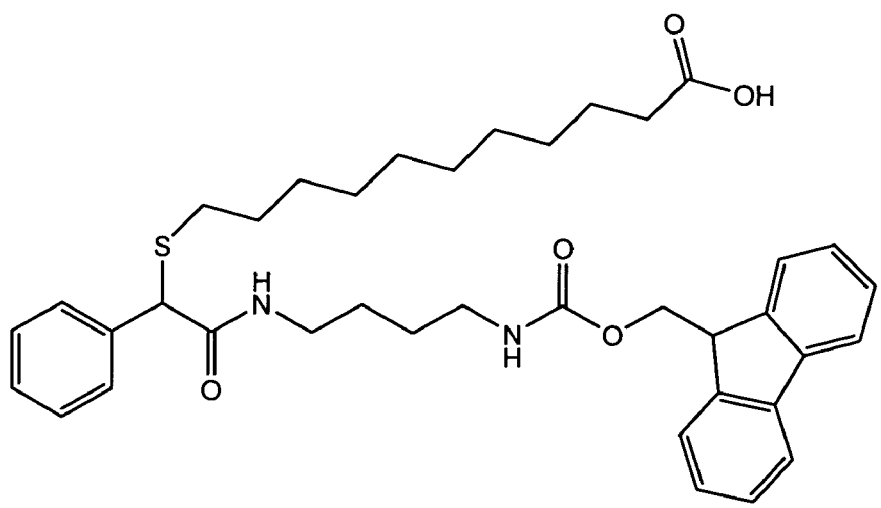
Figure 3F:
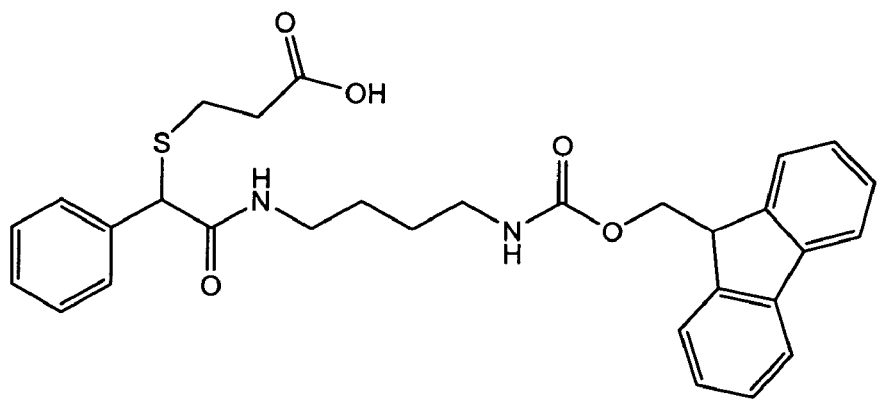

In one aspect of the invention, G represents amphiphilic compounds, particularly phospholipids. The phospholipids are based upon alkyl carboxylic acid esters of alkyl polyols, where at least one hydroxylic group is substituted with a carboxylic acid ester, where the alkyl group is as defined above. The alkyl group can thus have from about 1 to 50, more usually from about 10 to 20 carbon atoms, which may have from 0 to 5, more usually from 0 to 2, sites of ethylenic saturation and at least one hydroxyl group substituted with phosphate to form a phosphate ester. The phosphate group may be further substituted with small aliphatic compounds which are of di or higher functionality, and generally having hydroxyl or amino groups. Thus, the liphophilic moiety may include phospholipids such as phosphatidyl choline, phosphatidyl serine, phosphatidyl ethanolamine, phosphatidyl inositol, or cardiolipin, and sphingolipids such as sphingomyelin; Representative lipophilic groups are illustrated in FIG. 2.

In another aspect, G can be a peptide, more particularly a liphophilic or a greasy peptide, that is capable of associating with a bilayer, such as membranes. A greasy peptide generally refers to any peptide whose affinity for lipid surfaces is measured by a dissociation constant of $K^d$ about $10^{-6}$ or less. The ability of a greasy peptide to keep the compounds anchored in the membrane can be verified empirically, or can be predicted on the basis of a high proportion of lipophilic residues and relatively few charged residues using known algorithms. For example, use of a computer program that formulates a hydropathy scale from the amino acid and Hopp and Woods (1981) Proc. Natl. Acad. Sci. 78: 3824-3828. In one aspect, the greasy peptide can be a transmembrane domain that is capable of anchoring the compounds of the invention in the membranes. The transmembrane domain is thus sufficiently lipophilic to penetrate the lipid bilayer and keep the compounds inserted in the membrane in a stable fashion. Typically, the transmembrane domain will span the entire lipid bilayer one or more times. The transmembrane domain can be derived from the receptor under investigation, such as G-protein coupled receptors, and can provide a second signal. Alternatively, artificially designed polypeptide sequences can be used for transmembrane domains in this invention. When G is a transmembrane domain, it can be attached to the cleavable linkage (L) by known methods, such as via an amide bond.

The Cleavable Linkage (L)

Cleavable linkage, L, can be virtually any chemical linking group that may be cleaved under conditions that do not degrade the structure or affect detection characteristics of the released electrophoretic tag, E. Whenever membrane anchored electrophoretic probes are used in a homogeneous assay format, cleavable linkage, L, is cleaved by a cleavage agent that acts over a short distance so that only cleavable linkages in its immediate proximity are cleaved. Typically, such an agent must be activated by making a physical or chemical change to the reaction mixture so that the agent produces a short lived active species that diffuses to a cleavable linkage to effect cleavage. In a homogeneous format, the cleavage agent is preferably attached to a binding moiety, such as an antibody, that targets prior to activation the cleavage agent to a particular site in the proximity of the membrane anchored electrophoretic probe, such as a receptor or like molecules, in the same membrane. In such embodiments, a cleavage agent is referred to herein as a "cleavage-inducing moiety," which is discussed more fully below.

In a non-homogeneous format, labeled objects, such as biological cells, liposomes, or the like, with desired properties, are separated or isolated from objects not having such properties. Thus, a wider selection of cleavable linkages and cleavage agents are available for use with the invention. Cleavable linkages may not only include linkages that are labile to reaction with a locally acting reactive species, such as hydrogen peroxide, singlet oxygen, or the like, but also linkages that are labile to agents that operate throughout a reaction mixture, such as base-labile linkages, photocleavable linkages, linkages cleavable by reduction, linkages cleaved by oxidation, acid-labile linkages, peptide linkages cleavable by specific proteases, and the like. References describing many such linkages include Greene and Wuts, Protective Groups in Organic Synthesis, Second Edition (John Wiley & Sons, New York, 1991); Hermanson, Bioconjugate Techniques (Academic Press, New York, 1996); and Still et al, U.S. Pat. No. 5,565,324. Exemplary cleavable linkages are illustrated in Table 1.

TABLE 1

| Linking Group | Cleavage Reagent |
| --- | --- |
| silyl | fluoride or acid |
| A | hv |
| B | $Ce(NH_4)_2(NO_3)_6$ |
| —NCO$_2$— | $HO^-$, $H^+$, or $LiAlH_4$ |
| C | $O_3$, $OsO_4/IO_4$, or $KMnO_4$ |
| D | 1) $O_2$ or $Br_2$, MeOH |
|   | 2) $H_3O^+$ |
| —Si— | oxidation, $H^+$, $Br_2$, $Cl_2$, etc. |
| E | $H_3O^+$ |
| F | $H_3O^+$ |
| G | F or $H^+$ |
| H, where x is a keto, ester, amide, $NO_2$, sulfide, sulfoxide, sulfone, and related electron withdrawing groups. | base, $HO^-$ |
| I | $H_3O^+$ or reduction (e.g. $Li/NH_3$) |
| J | $(Ph_3P)_3RhCl(H)$ |
| K | Li, Mg, or BuLi |
| M | $Hg^{+2}$ |
| N, where x is halogen or pseudohalogen | Zn or Mg |
| O | oxidation (e.g. $Pb(OAc)_4$ or $H_5IO_6$) |
| P, where X is a electron withdrawing group | base |

Illustrative cleavable linking groups and cleavage reagents
(L) shows the point of attachment of the electrophoretic tag (E).

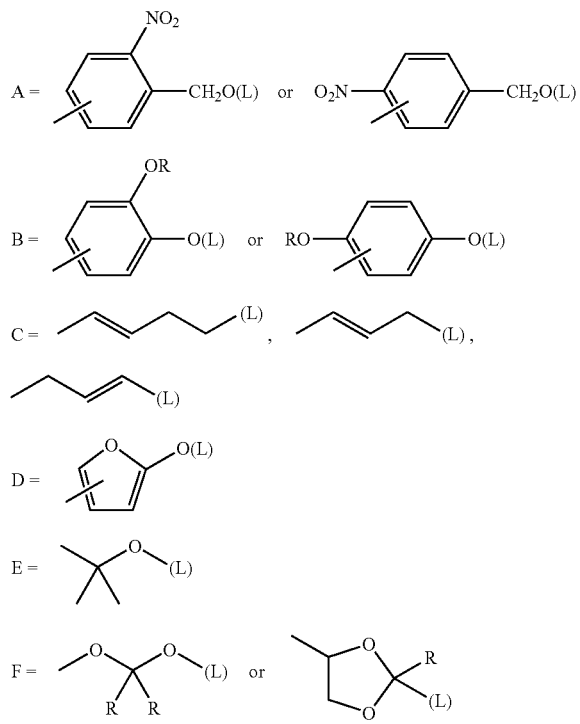

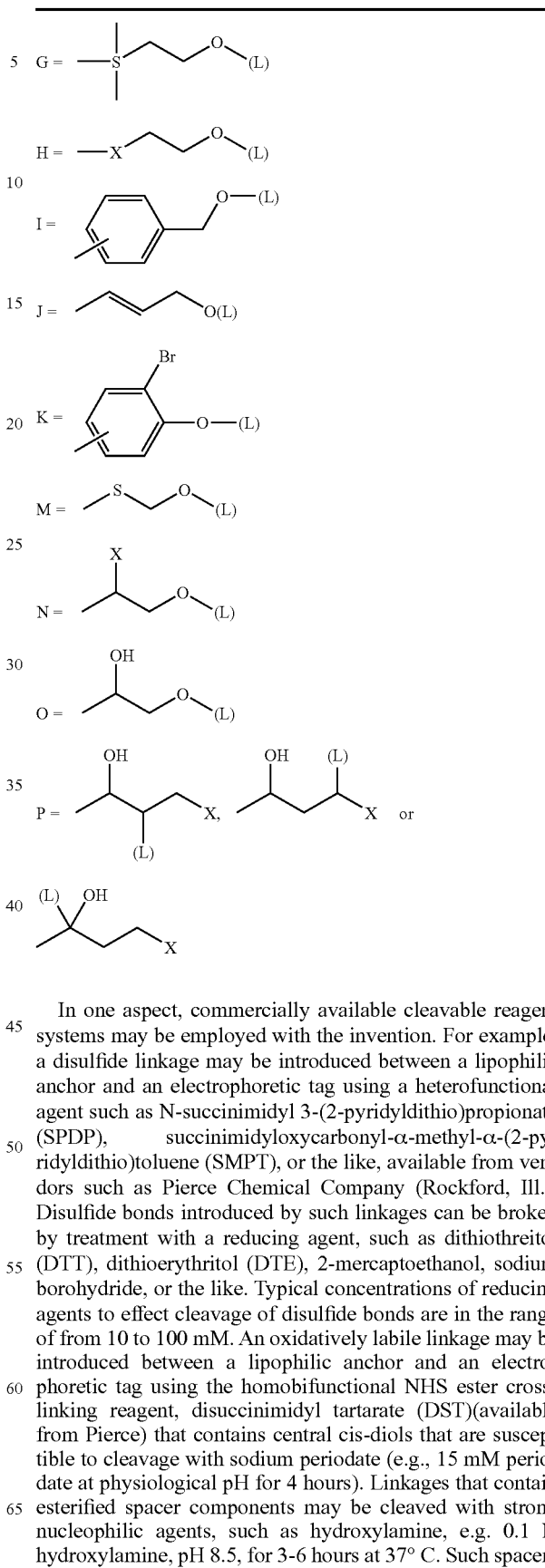

In one aspect, commercially available cleavable reagent systems may be employed with the invention. For example, a disulfide linkage may be introduced between a lipophilic anchor and an electrophoretic tag using a heterofunctional agent such as N-succinimidyl 3-(2-pyridyldithio)propionate (SPDP), succinimidyloxycarbonyl-α-methyl-α-(2-pyridyldithio)toluene (SMPT), or the like, available from vendors such as Pierce Chemical Company (Rockford, Ill.). Disulfide bonds introduced by such linkages can be broken by treatment with a reducing agent, such as dithiothreitol (DTT), dithioerythritol (DTE), 2-mercaptoethanol, sodium borohydride, or the like. Typical concentrations of reducing agents to effect cleavage of disulfide bonds are in the range of from 10 to 100 mM. An oxidatively labile linkage may be introduced between a lipophilic anchor and an electrophoretic tag using the homobifunctional NHS ester cross-linking reagent, disuccinimidyl tartarate (DST)(available from Pierce) that contains central cis-diols that are susceptible to cleavage with sodium periodate (e.g., 15 mM periodate at physiological pH for 4 hours). Linkages that contain esterified spacer components may be cleaved with strong nucleophilic agents, such as hydroxylamine, e.g. 0.1 N hydroxylamine, pH 8.5, for 3-6 hours at 37° C. Such spacers can be introduced by a homobifunctional cross-linking agent such as ethylene glycol bis(succinimidylsuccinate)(EGS) available from Pierce (Rockford, Ill.). A base labile linkage can be introduced with a sulfone group. Homobifunctional cross-linking agents that can be used to introduce sulfone groups in a cleavable linkage include bis[2-(succinimidyloxycarbonyloxy)ethyl]sulfone (BSOCOES), and 4,4-difluoro-3,3-dinitrophenylsulfone (DFDNPS). Exemplary basic conditions for cleavage include 0.1 M sodium phosphate, adjusted to pH 11.6 by addition of Tris base, containing 6 M urea, 0.1% SDS, and 2 mM DTT, with incubation at 37° C. for 2 hours.

Photocleavable linkages include those disclosed in Rothschild et al, U.S. Pat. No. 5,986,076.

In one aspect, whenever compounds of the invention are used in a homogeneous assay format, cleavable linkage, L, is cleaved by a short-lived active species that is generated by a cleavage-inducing moiety, such as an enzyme, sensitizer, or the like. Typically, the short-lived active species is an oxidizing agent, such as singlet oxygen, superoxide anion, hydrogen peroxide, or the like, and cleavable linkage, L, is cleaved whenever the local concentration of such active species is sufficiently high. Such oxidatively labile linkages include thioethers, selenoethers, olefins, and the like. In one aspect, olefin linkages of the invention include moieties of the following structure:

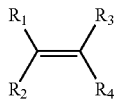

where $R_1$-$R_4$ is a carbon-containing group which may also contain a heteroatom such as oxygen, nitrogen, sulfur, or halogen, for example. $R_1$-$R_4$ can be independently selected from the group consisting of hydrogen, alkyl, heteroalkyl, heteroaryl, heteroaralkyl, aryloxy, aryl, substituted aryl, hydroxyaryl or substituted hydroxyaryl, acyloxyaryl or substituted acyloxyaryl, silyloxyaryl or substituted siloxyaryl, aminoaryl or substituted aminoaryl, and sulfonamidoaryl or substituted sulfonamidoaryl. Any of the $R_1$-$R_4$ groups may be joined together to form one or more rings either on one side of the double bond, or across the double bond. The linking of the R groups may be through a bond, or through a bridge which may be a heteroatom or a carbon containing group optionally containing one or more heteroatoms. Preferably, one of the R groups is an electron donating group, attached directly to the olefin or through conjugated double bonds. Enol ethers, enediol ethers, vinyl sulfides, enamines, and N-acylenamines are examples of olefins useful in the invention, where the heteroatom of the heteroalkyl substituent is attached directly to the double bond. The $R_1$-$R_4$ groups are independently selected from a wide variety of substituents. Preferred substituents include aryl groups, such as phenyl and naphthyl groups, oxy groups of the formula $YO_B$, wherein Y is aryl, alkyl, aralkyl, cycloalkyl, and the like, thio groups of the formula $YS_B$, amino groups of the formula $YHN_B$, and alkyl groups selected such that there is no proton in the allylic group position. Preferably, at least one R group is a $YO_B$ or $YS_B$ group, as the presence of the heteroatom promotes dioxetane formation. Each of the R groups may be substituted with optional substituents, including halogens, amines, alkoxy, heteroaryl, and the like. One or more of the R groups may comprise an auxiliary fluorophore, such as anthracenes, rhodamines, flyoescins, coumarins, eryth- rosins, acridines, pyrenes, stilbenes, nitrobenzoxadiazoles, quinolines, acidoacridines, carbazoles, flyorescent cyanines, carbocyanines, pyridinium salts, oxonols, resortins, and derivatives of these groups, as well as phenyl and naphthyl moieties. The lipophilic moiety (G) and the electrophoretic group (E) can be attached to the olefin directly, or via two of the R groups.

Further, one of the R groups may bear a protective group which, if removed, induces decomposition of the dioxetane group formed from the precursor. These include corresponding enzyme-labile substrates, such as phosphates, for example, and groups which may be removed by addition of non-enzymatic chemicals, such as base, electron donors, and the like, such as a silyl-protected OH group.

Thus in one aspect of the invention, L is a thioether or its selenium analog; or an olefin, which contains carbon-carbon double bonds, wherein cleavage of a double bond to an oxo group, releases the electrophoretic tag, E. Illustrative olefins include vinyl sulfides, vinyl ethers, enamines, imines substituted at the carbon atoms with an α-methine (CH, a carbon atom having at least one hydrogen atom), where the vinyl group may be in a ring, the heteroatom may be in a ring, or substituted on the cyclic olefinic carbon atom, and there will be at least one and up to four heteroatoms bonded to the olefinic carbon atoms. The resulting dioxetane may decompose spontaneously, by heating above ambient temperature, usually below about 75° C., by reaction with acid or base, or by photo-activation in the absence or presence of a photosensitizer. Such reactions are described in the following exemplary references: Adam and Liu, J. Amer. Chem. Soc. 94, 1206-1209, 1972, Ando, et al., J. C. S. Chem. Comm. 1972, 477-8, Ando, et al., Tetrahedron 29, 1507-13, 1973, Ando, et al., J. Amer. Chem. Soc. 96, 6766-8, 1974, Ando and Migita, ibid. 97, 5028-9, 1975, Wasserman and Terao, Tetra. Lett. 21, 1735-38, 1975, Ando and Watanabe, ibid. 47, 4127-30, 1975, Zaklika, et al., Photochemistry and Photobiology 30, 35-44, 1979, and Adam, et al., Tetra. Lett. 36, 7853-4, 1995. See also, U.S. Pat. No. 5,756,726.

The formation of dioxetanes is obtained by the reaction of singlet oxygen with an activated olefin substituted with an electrophoretic tag (eTag) at one carbon atom and the lipophilic binding moiety at the other carbon atom of the olefin. See, for example, U.S. Pat. No. 5,807,675. These cleavable linkages may be depicted by the following formula:

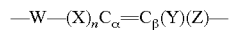

wherein:

W may be a bond, a heteroatom, e.g., O, S, N, P, M (intending a metal that forms a stable covalent bond), or a functionality, such as carbonyl, imino, etc., and may be bonded to X or $C_β$;

at least one X will be aliphatic, aromatic, alicyclic or heterocyclic and bonded to $C_α$ through a heteroatom, e.g., N, O, or S and the other X may be the same or different and may in addition be hydrogen, aliphatic, aromatic, alicyclic or heterocyclic, usually being aromatic or aromatic heterocyclic wherein one X may be taken together with Y to form a ring, usually a heterocyclic ring, with the carbon atoms to which they are attached, generally when other than hydrogen being from about 1 to 20, usually 1 to 12, more usually 1 to 8 carbon atoms and one X will have 0 to 6, usually 0 to 4 heteroatoms, while the other X will have at least one heteroatom and up to 6 heteroatoms, usually 1 to 4 heteroatoms;

Y will come within the definition of X, usually being bonded to $C_\beta$ through a heteroatom and as indicated may be taken together with X to form a heterocyclic ring;

Z will usually be aromatic, including heterocyclic aromatic, of from about 4 to 12, usually 4 to 10 carbon atoms and 0 to 4 heteroatoms, as described above, being bonded directly to $C_\beta$ or through a heteroatom, as described above;

n is 1 or 2, depending upon whether the electrophoretic moiety is bonded to $C_\alpha$ or X;

wherein one of Y and Z will have a functionality for binding to the lipophilic moiety, or be bound to the lipophilic moiety, e.g. by serving as, or including a linkage group, to a lipophilic moiety, G.

Preferably, W, X, Y, and Z are selected so that upon cleavage, the electrophoretic tag, E, is within the size limits described below.

While not depicted in the formula, there may be a plurality of electrophoretic moieties in a single molecule, by having one or more electrophoretic moieties joined to one or both Xs.

Illustrative cleavable linkages include S(eTag)-3-thiolacrylic acid, N(eTag)-, N-methyl 4-amino-4-butenoic acid, O-(eTag)-, 3-hydroxyacrolein, N-(4-carboxyphenyl)-2-(eTag)-imidazole, oxazole, and thiazole.

Also of interest are N-alkyl acridinyl derivatives, substituted at the 9 position with a divalent group of the formula:

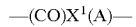

—(CO)X¹(A)— wherein:

$X^1$ is a heteroatom selected from the group consisting of O, S, N, and Se, usually one of the first three; and A is a chain of at least 2 carbon atoms and usually not more than 6 carbon atoms substituted with an electrophoretic tag reporter, where preferably the other valences of A are satisfied by hydrogen, although the chain may be substituted with other groups, such as alkyl, aryl, heterocyclic groups, etc., A generally being not more than 10 carbon atoms.

Also of interest are heterocyclic compounds, such as diheterocyclopentadienes, as exemplified by substituted imidazoles, thiazoles, oxazoles, etc., where the rings will usually be substituted with at least one aromatic group and in some instances hydrolysis will be necessary to release the electrophoretic tag reporter.

Also of interest are tellurium (Te) derivatives, where the Te is bonded to an ethylene group having a hydrogen atom β to the Te atom, wherein the ethylene group is part of an alicyclic or heterocyclic ring, that may have an oxo group, preferably fused to an aromatic ring and the other valence of the Te is bonded to the electrophoretic tag reporter. The rings may be coumarin, benzoxazine, tetralin, etc.

Several representative cleavable linkages and their cleavage products are illustrated in Table 1 and FIG. 3. The thiazole cleavable linkage, "—$CH_2$-thiazole-$(CH2)_n$—C (=O)—NH-protein," results in an electrophoretic tag with the moiety "—$CH_2$—C(=O)—NH—CHO." Preferably, n is in the range of from 1 to 12, and more preferably, from 1 to 6. The oxazole cleavable linkage, "—$CH_2$-oxazole-$(CH_2)_n$—C(=O)—NH-protein," results in an electrophoretic tag with the moiety "—$CH_2$—C(=O)O—CHO." An olefin cleavable linkage is shown in connection with the electrophoretic probe embodiment "G-L-M-D," described above and with D being a fluorescein dye. The olefin cleavable linkage may also be employed in other embodiments. Cleavage of the illustrated olefin linkage results in an electrophoretic tag of the form: "R—(C=O)-M-D," where "R" may be any substituent within the general description of the electrophoretic tags, E, provided above. Preferably, R is an electron-donating group, e.g. Ullman et al, U.S. Pat. No. 6,251,581; Smith and March, March=s Advanced Organic Chemistry: Reactions, Mechanisms, and Structure, 5$^{th}$ Edition (Wiley-Interscience, New York, 2001); and the like. More preferably, R is an electron-donating group having from 1-8 carbon atoms and from 0 to 4 heteroatoms selected from the group consisting of O, S, and N. In further preference, R is —$N(Q)_2$, —OQ, p-$[C_6H_4N(Q)_2]$, furanyl, n-alkylpyrrolyl, 2-indolyl, or the like, where Q is alkyl or aryl. In further reference to the olefin cleavable linkage of FIG. 3, substituents "X" and "R" are equivalent to substituents "X" and "Y" of the above formula describing cleavable linkage, L. In particular, X is preferably morpholino, —OR', or —SR", where R' and R" are aliphatic, aromatic, alicyclic or heterocyclic having from 1 to 8 carbon atoms and 0 to 4 heteroatoms selected from the group consisting of O, S. and N. A preferred thioether cleavable linkage is illustrated in FIG. 3 having the form "—$(CH_2)_2$—S—$CH(C_6H_5)C$(=O) NH—$(CH_2)_n$—NH—," wherein n is in the range of from 2 to 12, and more preferably, in the range of from 2 to 6. Thioether cleavable linkages may be attached to lipophilic moieties, G, and electrophoretic tags, E, by way of precursor compounds shown in FIG. 4. To attach to an amino group of a lipophilic moiety, G, the terminal hydroxyl is converted to an NHS ester by conventional chemistry. After reaction with the amino group and attachment, the Fmoc protection group is removed to produce a free amine which is then reacted with an NHS ester of the electrophoretic tag.

In another aspect of the invention, the cleavage moiety, L, is an "enzyme-cleavable peptide," which is a peptide comprising an amino acid sequence that is recognized by a peptidase. Enzyme-cleavable peptides, typically from about 2 to 20 amino acids in length, are of sufficient length to project above the surfaces of the lipid bilayers. Such peptides are well known to ordinarily skilled artisans and include, for example and without limitation, the amino acid sequences: Ala-Ala-, Ala-Ala-Pro-Val (SEQ ID NO:1), Ala-Ala-Met-, Ala-Ala-Pro-Phe- (SEQ ID NO:2), Ala-Ala-Pro-Met- (SEQ ID NO:3), Ala-Ala-Arg, Ser-Ala-Ala-Arg- (SEQ ID NO:4), Ser-Ser-Ala-Ala-Arg- (SEQ ID NO:5), Ser-S carboxyl sugar-Ala-Ala-Arg- (SEQ ID NO:6), Ala-Ala-Asp-, Ser-Ala-Ala-Asp- (SEQ ID NO:7), Ser-Ser-Ala-Ala-Asp- (SEQ ID NO:8), Arg-Pro-Lys-Pro-Leu-Ala-Nva- (SEQ ID NO:9), Ser-Arg-Pro-Lys-Pro-Leu-Ala-Nva- (SEQ ID NO:10), Ser-Ser-Arg-Pro-Lys-Pro-Leu-Ala-Nva (SEQ ID NO:11), Pro-Cha-Gly-Nva-His-Ala-Dpa-$NH_2$ (SEQ ID NO:12), Pro-Leu-Gly-Leu-Dpa-Ala-Arg-$NH_2$ (SEQ ID NO:13), Pro-Cha-Gly-Nva-, Pro-Leu-Gly-Leu (SEQ ID NO:14), Gly-Pro-Arg, Leu-Pro-Arg, Glu-Gly-Arg, and Gly-Pro-Gln-Gly-Ile- (SEQ ID NO: 15).

The Electrophoretic Group (E)

In one aspect of the invention, the electrophoretic tag, E, is a water soluble organic compound that is stable with respect to the active species, especially singlet oxygen, and that includes a detection or reporter group. Otherwise, E may vary widely in size and structure. Preferably, E carries a charge at neutral pH and has a molecular weight in the range of from about 150 to about 10,000 daltons, more preferably, from about 150 to about 5000 daltons, and most preferably, from about 150 to 2500 daltons. Preferred structures of E are described more fully below. Preferably, the detection group generates an electrochemical, fluorescent, or chromogenic signal. Most preferably, the detection group generates a fluorescent signal. Compositions of the invention include pluralities of electrophoretic tags that may be used together to carry out the multiplexed assays of the invention. Preferably, the plurality of electrophoretic tags in a composition is at least 5, and more preferably, at least 10. Still more preferably, the plurality of electrophoretic tags is in the range of from 5 to 200, and more preferably, from 5 to 100, or 5 to 75, or from 5 to 50, or from 10 to 30. Preferably, electrophoretic tags within a plurality of a composition each have either a unique charge-to-mass ratio and/or a unique optical property with respect to the other members of the same group of tags. Preferably, the optical property is a fluorescence property, such as emission spectrum, fluorescence lifetime, or the like. More preferably, the fluorescence property is an emission spectrum. For example, each electrophoretic tag of a plurality of tags may have the same fluorescent emission properties, but each will differ from one another by virtue of unique charge-to-mass ratios. On the other hand, two or more of the electrophoretic tags of a plurality of tags may have identical charge-to-mass ratios, but they will have unique fluorescent properties, e.g. spectrally resolvable emission spectra, so that all the members of the plurality are distinguishable by the combination of electrophoretic separation and fluorescence measurement.

Preferably, electrophoretic tags in a plurality of tags are detected by electrophoretic separation and fluorescence. Preferably, electrophoretic tags having substantially identical fluorescence properties have different electrophoretic mobilities so that distinct peaks in an electropherogram are formed under separation conditions. A measure of the distinctness, or lack of overlap, of adjacent peaks is electrophoretic resolution, which is the distance between adjacent peak maximums divided by four times the larger of the two standard deviations of the peaks. Preferably, adjacent peaks have a resolution of at least 1.0, and more preferably, at least 1.5, and most preferably, at least 2.0. In a given separation and detection system, the desired resolution may be obtained by selecting a plurality of electrophoretic tags whose members have electrophoretic mobilities that differ by at least a peak-resolving amount, such quantity depending on several factors well known to those of ordinary skill, including the signal detection system, the nature of the fluorescent moieties, the diffusion coefficients of the tags, the presence or absence of sieving matrices, nature of the electrophoretic apparatus, e.g. presence or absence of channels, length of separation channels, and the like. Preferably, pluralities of electrophoretic tags of the invention are separated by a conventional capillary electrophoresis apparatus, either in the presence or absence of a conventional sieving matix. Exemplary capillary electroresis apparatus include Applied Biosystems (Foster City, Calif.) models 310, 3100 and 3700; Beckman (Fullerton, Calif.) model P/ACE MDQ; Amersham Biosciences (Sunnyvale, Calif.) MegaBACE 1000 or 4000; SpectruMedix genetic analysis system; and the like. Preferably, in such a conventional apparatus, the electrophoretic mobilities of a plurality electrophoretic tags differ by at least one percent, and more preferably, by at least a percentage in the range of from 1 to 10 percent.

Electrophoretic mobility is proportional to $q/M^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01, and may be 0.02 or more.

A preferred structure of electrophoretic tag, E, is (M, D), where M is a mobility-modifying moiety and D is a detection moiety. The notation "(M, D)" is used to indicate that the ordering of the M and D moieties may be such that either moiety can be adjacent to the cleavable linkage, L. That is, "G-L-(M, D)" designates electrophoretic probe of either of two forms: "G-L-M-D" or "G-L-D-M."

Detection moiety, D, may be a fluorescent label or dye, a chromogenic label or dye, an electrochemical label, or the like. Preferably, D is a fluorescent dye. Exemplary fluorescent dyes for use with the invention include water-soluble rhodamine dyes, fluoresceins, 4,7-dichlorofluoresceins, benzoxanthene dyes, and energy transfer dyes, disclosed in the following references: Handbook of Molecular Probes and Research Reagents, 8th ed., (Molecular Probes, Eugene, 2002); Lee et al., U.S. Pat. No. 6,191,278; Lee et al., U.S. Pat. No. 6,372,907; Menchen et al., U.S. Pat. No. 6,096,723; Lee et al., U.S. Pat. No. 5,945,526; Lee et al., Nucleic Acids Research, 25: 2816-2822 (1997); Hobb, Jr., U.S. Pat. No. 4,997,928; Khanna et al., U.S. Pat. No. 4,318,846; Reynolds, U.S. Pat. No. 3,932,415; Eckert et al., U.S. Pat. No. 2,153,059; Eckert et al., U.S. Pat. No. 2,242,572; Taing et al., International patent publication WO 02/30944; and the like. Further specific exemplary fluorescent dyes include 5- and 6-carboxyrhodamine 6G; 5- and 6-carboxy-X-rhodamine, 5- and 6-carboxytetramethylrhodamine, 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 1',2',7',8'-dibenzo-4',5'-dichloro-5- and 6-carboxy-4,7-dichlorofluoresce, 2',7'-dichloro-5- and 6-carboxy-4,7-dichlorofluorescein, and 2',4',5',7'-tetrachloro-5- and 6-carboxy-4,7-dichlorofluorescein. Most preferably, D is a fluorescein or a fluorescein derivative.

M is generally a chemical group or moiety that has or is designed to have a particular charge-to-mass ratio, and thus a particular electrophoretic mobility in a defined electrophoretic system. Exemplary types of mobility-modifying moieties are discussed below. The mobility-modifying moiety may have a mass-modifying region and/or a charge-modifying region or a single region that acts as both a mass- and charge-modifying region. As noted above, D is typically common among a set or plurality of different electrophoretic probes, but may also differ among probe sets, contributing to the unique electrophoretic mobilities of the released electrophoretic tag. Preferably, the released electrophoretic tag (m,d), has a charge/mass ratio in the range of about -0.001 to 0.5.

The size, structure, and composition of M can vary widely. Design factors that affect selection of particular M's in a set include (i) solubility in desired reaction buffers and electrophoretic separation media, (ii) the nature of the cleavage agent and whether M is stable to its action, (iii) whether M imparts a charge/mass ratio on (M,D) that is distinct with respect to electrophoretic tags of the same set, (iv) whether M confers an electrophoretic mobility on (M,D) that permits separation on a particular electrophoresis instrument or in a particular electrophoretic separation media, and like factors. In one aspect, M is an organic moiety consisting of from 1 to 500 atoms selected from the group consisting of carbon, oxygen, hydrogen, sulfur, nitrogen, phosphorus, and boron. Preferably, such M consists of from 1 to 300 atoms, and more preferably, from 1 to 200 atoms. Where acid groups are present, depending upon the pH of the medium in which the mobility-modifying moiety is present, various cations may be associated with the acid group. The acids may be organic or inorganic, including carboxyl, thionocarboxyl, thiocarboxyl, hydroxamic, phosphate, phosphite, phosphonate, phosphinate, sulfonate, sulfinate, boronic, nitric, nitrous, etc.

For positive charges, substituents include amino (including ammonium), phosphonium, sulfonium, oxonium, etc., where substituents are generally aliphatic of from about 1-6 carbon atoms, the total number of carbon atoms per heteroatom, usually being less than about 12, usually less than about 9. The side chains include amines, ammonium salts, hydroxyl groups, including phenolic groups, carboxyl groups, esters, amides, phosphates, heterocycles. M may be a homo-oligomer or a hetero-oligomer, having different monomers of the same or different chemical characteristics, e.g., nucleotides and amino acids.

The charged mobility-modifying moieties generally have only negative or positive charges, although one may have a combination of charges, particularly where a region to which the mobility-modifying moiety is attached is charged and the mobility-modifying moiety has the opposite charge. The mobility-modifying moieties may have a single monomer that provides the different functionalities for oligomerization and that carries a charge. Alternatively, two monomers may be employed. Substituted diols may be used, where the substituents are charged and dibasic acids. Illustrative of such oligomers is the combination of diols or diamino, such as 2,3-dihydroxypropionic acid, 2,3-dihydroxysuccinic acid, 2,3-diaminosuccinic acid, 2,4-dihydroxyglutaric acid, etc. The diols or diamino compounds can be linked by dibasic acid, which dibasic acids include the inorganic dibasic acids indicated above, as well as dibasic acids, such as oxalic acid, malonic acid, succinic acid, maleic acid, fumaric acid, carbonic acid, etc. Instead of using esters, amides may be used, and amino acids or diamines and diacids may be employed. Alternatively, the hydroxyls or amines may be linked with alkylene or arylene groups.

By employing monomers that have substituents that provide for charges, or which may be modified to provide charges, for mobility-modifying moieties may be provided having the desired charge-to-mass ratio. For example, by using serine or threonine, the hydroxyl groups may be modified with phosphate to provide negatively charged mobility-modifying moieties. With arginine, lysine and histidine, positively charged mobility-modifying moieties are provided. Oligomerization may be performed in conventional ways to provide the appropriately sized mobility-modifying moiety. The different mobility-modifying moieties may have different orders of oligomers, generally from 1 to 20 monomeric units, more usually about 1 to 12, where a unit intends a repetitive unit that may have from 1 to 2 different monomers. For the most part, oligomers are used with other than nucleic acid target-binding regions. The polyfunctionality of the monomeric units provides for functionalities at the termini that may be used for conjugation to other moieties, so that the available functionality for reaction may be used to provide a different functionality. For example, a carboxyl group with an aminoethylthiol, to replace the carboxyl group can be used with a thiol functionality for reaction with an activated olefin.

By using monomers that have about 1 to about 3 charges, a low number of monomers can be employed to provide for mobility variation with changes in molecular weight. Of particular interest are polyolpolycarboxylic acids having from about two to four of each functionality, such as tartaric acid, 2,3-dihydroxyterephthalic acid, 3,4-dihydroxyphthalic acid, 3,4-dihydroxyphthalic acid, etc. To provide for an additional negative charge, these monomers may be oligomerized with a dibasic acid, such as a phosphoric acid derivative to form the phosphate diester. Alternatively, the carboxylic acids can be used with a diamine to form a polyamide, while the hydroxyl groups can be used to form esters, such as phosphate esters, or ethers such as the ether of glycolic acid, etc. To vary the mobility, various aliphatic groups of differing molecular weight may be employed, such as polymethylenes, polyoxyalkylenes, polyhaloaliphatic or aromatic groups, polyols, e.g., sugars, where the mobility will differ by at least about 0.01, more usually at least about 0.02 and more usually at least about 0.5.

In another aspect, (M,D) moieties are constructed from chemical scaffolds used in the generation of combinatorial libraries. For example, the following references describe scaffold compounds useful in generating diverse mobility modifying moieties: peptoids (PCT Publication No WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., Proc. Nat. Acad. Sci. U.S.A. 90: 6909-6913 (1993), vinylogous polypeptides (Hagihara et al. J. Amer. Chem. Soc. 114: 6568 (1992)), nonpeptidal peptidomimetics with a Beta-D-Glucose scaffolding (Hirschmann, R. et al., J. Amer. Chem. Soc. 114: 9217-9218 (1992)), analogous organic syntheses of small compound libraries (Chen, C. et al. J. Amer. Chem. Soc. 116: 2661(1994)), oligocarbamates (Cho, C. Y. et al. Science 261: 1303 (1993)), peptidyl phosphonates (Campbell, D. A. et al., J. Org. Chem. 59:658 (1994)); Cheng et al, U.S. Pat. No. 6,245,937; Heizmann et al, "Xanthines as a scaffold for molecular diversity," Mol. Divers. 2: 171-174 (1997); Pavia et al, Bioorg. Med. Chem., 4: 659-666 (1996); Ostresh et al, U.S. Pat. No. 5,856,107; Gordon, E. M. et al., J. Med. Chem. 37: 1385 (1994); and the like. Preferably, in this aspect, D is a substituent on a scaffold and M is the rest of the scaffold.

In yet another aspect, (M, D) moieties are constructed from one or more of the same or different common or commercially available linking, cross-linking, and labeling reagents that permit facile assembly, especially using a commercial DNA or peptide synthesizer for all or part of the synthesis. In this aspect, (M, D) moieties are made up of subunits usually connected by phosphodiester and amide bonds. Exemplary precursors that form amide bonds include Fmoc- or Boc-protected amino acid precursors, and derivatives thereof, e.g. as commercially available from AnaSpec, Inc. (San Jose, Calif.). Exemplary precursors that form phosphodiester bonds include, but are not limited to, dimethoxytrityl (DMT)-protected hexaethylene glycol phosphoramidite, 6-(4-Monomethoxytritylamino)hexyl-(2-cyanoethyl)-(N,N-diisopropyl)-phosphoramidite, 12-(4-Monomethoxytritylamino)dodecyl-(2-cyanoethyl)-(N,N-diisopropyl)-phosphoramidite, 2-[2-(4-Monomethoxytrityl)aminoethoxy]ethyl-(2-cyanoethyl), N,N-diisopropyl)-phosphoramidite, (S-Trityl-6-mercaptohexyl)-(2-cyanoethyl)-(N,N-diisopropyl)-phosphoramidite, 5'-Fluorescein phosphoramidite, 5'-Hexachloro-Fluorescein Phosphoramidite, 5'-Tetrachloro-Fluorescein Phosphoramidite, 9-O-Dimethoxytrityl-triethylene glycol, 1-[(2-cyanoethyl)-(N,N-diisopropyl)]-phosphoramidite, 3(4,4'-Dimethoxytrityloxy)propyl-1-[(2-cyanoethyl)-(N,N-diisopropyl)]-phosphoramidite, 5'-O-Dimethoxytrityl-1',2'-Dideoxyribose-3'-[(2-cyanoethyl)-(N,N-diisopropyl)]-phosphoramidite, 18-O-Dimethoxytritylhexaethyleneglycol, 1-[(2-cyanoethyl)-(N,N-diisopropyl)]-phosphoramidite, 12-(4,4'-Dimethoxytrityloxy)dodecyl-1-[(2-cyanoethyl)-(N,N-diisopropyl)]-phosphoramidite, 1,3-bis-[5-(4,4'-dimethoxytrityloxy)pentylamido]propyl-2-[(2-cyanoethyl)-(N,N-diisopropyl)]-phosphoramidite, 1-[5-(4,4'- dimethoxytrityloxy)pentylamido]-3-[5-fluorenomethoxycarbonyloxypentylamido]-propyl-2-[(2-cyanoethyl)-(N,N-diisopropyl)]-phosphoramidite, Tris-2,2,2-[3-(4,4'-dimethoxytrityloxy)propyloxymethyl]ethyl-[(2-cyanoethyl)-(N,N-diisopropyl)]-phosphoramidite, succinimidyl trans-4-(maleimidylmethyl) cyclohexane-1-carboxylate (SMCC), succinimidyl 3-(2-pyridyldithio)propionate (SPDP), succinimidyl acetylthioacetate, Texas Red-X-succinimidyl ester, 5- and 6-carboxytetramethylrhodamine succinimidyl ester, bis-(4-carboxypiperidinyl)sulfonerhodamine di(succinimidyl ester), 5- and 6-((N-(5-aminopentyl)aminocarbonyl)tetramethylrhodamine, succinimidyl 4-(p-maleimidophenyl)butyrate (SMPB); N-g-maleimidobutyryl-oxysuccinimide ester (GMBS); p-nitrophenyl iodoacetate (NPIA); 4-(4-N-maleimidophenyl)butyric acid hydrazide (MPBH); and like reagents. The above reagents are commercially available, e.g. from Glen Research (Sterling, Va.), Molecular Probes (Eugene, Oreg.), Pierce Chemical, and like reagent providers. Use of the above reagents in conventional synthetic schemes is well known in the art, e.g. Hermanson, Bioconjugate Techniques (Academic Press, New York, 1996). In particular, M may be constructed from the following reagents: dimethoxytrityl (DMT)-protected hexaethylene glycol phosphoramidite, 6-(4-Monomethoxytritylamino) hexyl-(2-cyanoethyl)-(N,N-diisopropyl)-phosphoramidite, 12-(4-Monomethoxytritylamino)dodecyl-(2-cyanoethyl)-(N,N-diisopropyl)-phosphoramidite, 2-[2-(4-Monomethoxytrityl)aminoethoxy]ethyl-(2-cyanoethyl), N,N-diisopropyl)-phosphoramidite, (S-Trityl-6-mercaptohexyl)-(2-cyanoethyl)-(N,N-diisopropyl)-phosphoramidite, 9-O-Dimethoxytrityl-triethylene glycol, 1-[(2-cyanoethyl)-(N,N-diisopropyl)]-phosphoramidite, 3(4,4'-Dimethoxytnityloxy) propyl-1-[(2-cyanoethyl)-(N,N-diisopropyl)]-phosphoramidite, 5'-O-Dimethoxytrityl-1',2'-Dideoxyribose-3'-[(2-cyanoethyl)-(N,N-diisopropyl)]-phosphoramidite, 18-O-Dimethoxytritylhexaethyleneglycol, 1-[(2-cyanoethyl)-(N,N-diisopropyl)]-phosphoramidite, 12-(4,4'-Dimethoxytrityloxy)dodecyl-1-[(2-cyanoethyl)-(N,N-diisopropyl)]-phosphoramidite, 1,3-bis-[5-(4,4'-dimethoxytrityloxy)pentylamido]propyl-2-[(2-cyanoethyl)-(N,N-diisopropyl)]-phosphoramidite, 1-[5-(4,4'-dimethoxytrityloxy)pentylamido]-3-[5-fluorenomethoxycarbonyloxypentylamido]-propyl-2-[(2-cyanoethyl)-(N,N-diisopropyl)]-phosphoramidite, Tris-2,2,2-[3-(4,4'-dimethoxytrityloxy)propyloxymethyl]ethyl-[(2-cyanoethyl)-(N,N-diisopropyl)]-phosphoramidite, succinimidyl trans-4-(maleimidylmethyl) cyclohexane-1-carboxylate (SMCC), succinimidyl 3-(2-pyridyldithio)propionate (SPDP), succinimidyl acetylthioacetate, succinimidyl 4-(p-maleimidophenyl)butyrate (SMPB); N-g-maleimidobutyryl-oxysuccinimide ester (GMBS); p-nitrophenyl iodoacetate (NPIA); and 4-(4-N-maleimidophenyl)butyric acid hydrazide (MPBH).

M may also comprise polymer chains prepared by known polymer subunit synthesis methods. Methods of forming selected-length polyethylene oxide-containing chains are well known, see, e.g. Grossman et al, U.S. Pat. No. 5,777,096. It can be appreciated that these methods, which involve coupling of defined-size, multi-subunit polymer units to one another, directly or via linking groups, are applicable to a wide variety of polymers, such as polyethers (e.g., polyethylene oxide and polypropylene oxide), polyesters (e.g., polyglycolic acid, polylactic acid), polypeptides, oligosaccharides, polyurethanes, polyamides, polysulfonamides, polysulfoxides, polyphosphonates, and block copolymers thereof, including polymers composed of units of multiple subunits linked by charged or uncharged linking groups. In addition to homopolymers, the polymer chains used in accordance with the invention include selected-length copolymers, e.g., copolymers of polyethylene oxide units alternating with polypropylene units. Additionally, polypeptides of selected lengths and amino acid composition (i.e., containing naturally occurring or man-made amino acid residues), as homopolymers or mixed polymers may be used.

In another aspect, the detection moiety of (M,D) generates a fluorescent signal by an energy transfer mechanism. Preferably, in this aspect, D has the form "$D_1$-g-$D_2$" where $D_1$ and $D_2$ are acceptor-donor pairs of molecules, e.g. Wu et al, Anal. Biochem., 218: 1-13 (1994), and g is a rigid linker that maintains $D_1$ and $D_2$ at a substantially constant distance. Guidance in selecting rigid linker, g, may be found in Wu et al (cited above) and in U.S. Pat. Nos. 5,863,727; 5,800,996; 5,945,526; and 6,008,379. Either $D_1$ or $D_2$ may be the acceptor and the other the donor molecule in the pair. Exemplary, energy transfer detection moieties for use with the invention are disclosed in Lee et al, U.S. Pat. No. 5,945,526; Lee et al, Nucleic Acids Research, 25: 2816-2822 (1997); Taing et al, International patent publication WO 02/30944; and like references. Preferably, rigid linker, g, is selected so that the distance between $D_1$ and $D_2$ is maintained at a substantially constant distance within the range of from 10-100 Angstroms. A wide variety of linking groups may be employed with the proviso that the linkage is stable to the presence of singlet oxygen. Preferably, $D_1$ and $D_2$ are selected from the set of fluorescein, rhodamine, rhodamine 6G, rhodamine 110, rhodamine X, tetramethylrhodamine, and halogenated derivatives thereof. More preferably, $D_1$ and $D_2$ are both fluorescein dyes.

In one aspect, g may be selected from any of $R_1$—$R_2$—$R_1$ and $R_1$—$R_2$—C(═O)—$X_1$—$R_3$, the latter being present in either orientation with respect to $D_1$ and $D_2$; where $X_1$ is O, S, or NH; $R_1$ is ($C_1$-$C_5$ alkyldiyl, $X_1$, C(═O)) such that any one to three the moieties in parentheses are arranged in any linear order; $R_2$ is a 5 to 6 membered ring selected from the group consisting of cyclopentene, cyclohexene, cyclopentadiene, cyclohexadiene, furan, pyrrole, isopyrole, isoazole, pyrazole, isoimidazole, pyran, pyrone, benzene, pyridine, pyridazine, pyrimidine, pyrazine oxazine, indene, benzofuran, thionaphthene, indole and naphthalene; $R_3$ is $C_1$-$C_5$ alkyldiyl.

In another aspect, after release, electrophoretic tag, E, is defined by the formula:

A-M-D wherein:

A is —C(═O)R, where R is aliphatic, aromatic, alicyclic or heterocyclic having from 1 to 8 carbon atoms and 0 to 4 heteroatoms selected from the group consisting of O, S, and N; —$CH_2$—C(═O)—NH—CHO; —$SO_2$H; —$CH_2$—C(═O)O—CHO; —C(═O)NH—$(CH_2)_n$—NH—C(═O)C(═O)—($C_6H_5$), where n is in the range of from 2 to 12;

D is a fluorescent dye;

M is as described above, with the proviso that the total molecular weight of A-M-D be within the range of from about 150 to about 5000 daltons, and In another aspect, a plurality of electrophoretic tags are released, having the formula (A-M-D)$_m$, where A, M, and D are as defined above, and m is an integer greater than or equal to 2, and less than about 1000. Thus, for multiplexing, m can be 2, 5, 10, 15, 20, 25, 50, or higher, depending on the number of different electrophoretic tags used. Preferably, m is about 5-20.

In a preferred aspect, D is a fluorescein and the total molecular weight of A-M-D is in the range of from about 150 to about 2500 daltons.

In another preferred aspect, D is of the form "$D_1$-g-$D_2$" as described above.

In some embodiments the electrophoretic moieties need not be charged but merely differ in mass. Thus, the same or similar monomers can be used, where the functionalities would be neutral or made neutral, such as esters and amides of carboxylic acids. Also, the electrophoretic moieties may be varied by isotopic substitution, such as $^2H$, $^{18}O$, $^{14}C$, etc.

Pluralities of electrophoretic tags may include oligopeptides for providing the charge, particularly oligopeptides of from 2-6, usually 2-4 monomers, either positive charges resulting from lysine, arginine and histidine or negative charges, resulting from aspartic and glutamic acid. Of course, one need not use naturally occurring amino acids, as well as unnatural or synthetic amino acids can be used, such as taurine, phosphate substituted serine or threonine, S-a-succinylcysteine, co-oligomers of diamines and amino acids, etc.

In one aspect of the present invention, the charge-imparting moiety is conveniently composed primarily of amino acids but also may include thioacids and other carboxylic acids having from one to five carbon atoms. The charge imparting moiety may have from about 1 to about 30, preferably about 1 to about 20, more preferably, about 1 to about 10 amino acids per moiety and may also comprise about 1 to about 3 thioacids or other carboxylic acids. However, when used with an uncharged sub-region, the charged sub-region will generally have from about 1 to about 4, frequently about 1 to about 3 amino acids. As mentioned above, any amino acid, either naturally occurring and/or synthetic, may be employed.

In another aspect, G-L-M-D may be represented by the formula:

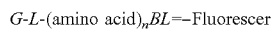

G-L-(amino acid)$_n$BL=—Fluorescer wherein L=is a bond or a linking group of from 1 to 20 atoms other than hydrogen, n is 1 to 20, and L is a cleavable linkage to the polypeptide-binding moiety. In this embodiment G is linked to the terminal amino acid by a cleavable linkage. An example of this embodiment, by way of illustration and not limitation, is one in which the fluorescer is fluorescein, L=is a bond in the form of an amide linkage involving the meta-carboxyl of the fluorescein and the terminal amine group of lysine, and G is a polypeptide-binding moiety.

In another aspect, mobility-modifying moiety, M, is dependent on using an alkylene or aralkylene (comprising a divalent aliphatic group having about 1 to about 2 aliphatic regions and about 1 to about 2 aromatic regions, generally benzene), where the groups may be substituted or unsubstituted, usually unsubstituted, of from about 2 to about 16, more usually about 2 to about 12, carbon atoms, where the mobility-modifying moiety may link the same or different fluorescers to a monomeric unit, e.g., a nucleotide. The mobility-modifying moiety may terminate in a carboxy, hydroxy or amino group, being present as an ester or amide. By varying the substituents on the fluorophore, one can vary the mass in units of at least about 5 or more, usually at least about 9, so as to be able to obtain satisfactory separation in capillary electrophoresis. To provide further variation, a thiosuccinimide group may be employed to join alkylene or aralkylene groups at the nitrogen and sulfur, so that the total number of carbon atoms may be in the range of about 2 to about 30, more usually about 2 to about 20. Instead of or in combination with the above groups and to add hydrophilicity, alkyleneoxy groups may be used.

Besides the nature of the mobility-modifying moiety, as already indicated, diversity can be achieved by the chemical and optical characteristics of the label, the use of energy transfer complexes, variation in the chemical nature of the mobility-modifying moiety, which affects mobility, such as folding, interaction with the solvent and ions in the solvent, and the like. In one embodiment of the invention, the mobility-modifying moiety may be an oligomer, where the mobility-modifying moiety may be synthesized on a support or produced by cloning or expression in an appropriate host. Conveniently, polypeptides can be produced where there is only one cysteine or serine/threonine/tyrosine, aspartic/glutamic acid, or lysine/arginine/histidine, other than an end group, so that there is a unique functionality, which may be differentially functionalized. By using protective groups, a side-chain functionality can be distinguished from a terminal amino acid functionality. Also, by appropriate design, one may provide for preferential reaction between the same functionalities present at different sites on the mobility-modifying moiety. Whether one uses synthesis or cloning for preparation of oligopeptides, is to a substantial degree dependent on the length of the mobility-modifying moiety.

Lipophilic Groups Indirectly Labeled with Electrophoretic Tags

As mentioned above, lipophilic moieties may be attached indirectly to cleavable linkages and electrophoretic tags by way of capture moieties and capture agents, as illustrated by the formula:

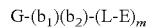

G-($b_1$)($b_2$)-(L-E)$_m$ wherein G, L, E, and m are as defined above, and $b_1$ is a capture moiety and $b_2$ is its corresponding capture agent. Exemplary capture moieties include biotin, iminobiotin, diaminobiotin, digoxigenin, fluorescein, dinitrophenol, or the like. Exemplary capture agents for biotin are avidin or streptavidin. Exemplary capture agents for digoxigenin, fluorescein, and dinitrophenol include specific monoclonal antibodies. Preferably, the capture moiety is biotin and the capture agent is either avidin or streptavidin.

In one aspect of the invention, the lipophilic group can be coupled to biotin. The lipophilic biotin compound can then be attached to the cells, membranes, liposomes, and the like, by incorporation into the bilayer, as detailed below. The labeled cells thus obtained can be contacted with a biotin-binding moiety, such as avidin, streptavidin, or anti-biotin antibodies. In one aspect, the biotin-binding moiety can be covalently attached to an electrophoretic tag. In another aspect, the biotin-binding moiety can be attached to the electrophoretic tag via a cleavable linker. In yet another aspect, the biotin-binding moiety can be contacted with a second biotin where an electrophoretic tag is attached to the second biotin via a cleavable linker. The binding of the lipophilic biotin to the biotin-binding moiety can be determined, as detailed below, by using a cleavage agent to cleave the cleavable linker, thereby releasing the electrophoretic tag. In another aspect, the labeled cells, membranes, liposomes, and the like, can be exposed to an endocytosis inducing agent, the remaining electrophoretic tags exposed on the surface can be cleaved with a cleavage agent, and the released tags detected and quantified thereby providing information on the extent of endocytosis.

The lipophilic group can be derivatized with biotin. Biotin is a low molecular weight, optically active organic acid, and the active form is the d isomer. Besides biotin, biocytin, D-sulfoxide of biotin, L-sulfoxide of biotin, biotin sulfane or desthiobiotin can be used in the present invention. Biotin or its analogues can be attached to the lipophilic group via an ester bond, an ether bond, an amide bond, via the N-hydroxysuccinimide ester, and the like, by methods known in the art. The biotinylated lipophilic group (biotin-G) retains the basic characteristics of the non-conjugated lipophilic group with respect to the orientation and position in the membrane bilayer. The biotinylated lipophilic group can thus be used to study the interaction of receptors, such as G-protein coupled receptors, with ligands, such as agonists and antagonists.

In one aspect of the present invention, biotinylated lipophilic groups (biotin-G) are non-covalently coupled to biotin-binding moieties. The biotin-binding moieties can be streptavidin or avidin. In this aspect of the invention, the first step involves incorporation of biotin-G into the cell membranes, membranes, liposomes or micelles, followed by a second step of binding the avidin or streptavidin to the biotin-G. There are four biotin binding sites on the streptavidin, which makes cells, membranes or liposomes containing biotin aggregate with streptavidin in an excess of biotin-G. In one aspect, the amount of biotin-G to incorporate into the membranes or liposomes can be titrated in order to prevent this aggregation, while maximizing the avidin or streptavidin coupling. Values for biotin-G may range from about 0.05 to about 0.8 mole % of the membranes or liposomes, or more preferably about 0.1 to about 0.5 mole % of the membranes or liposomes. In another aspect, the labeled cell membranes contacted with avidin or streptavidin that are optionally derivatized with L-E, can be contacted with another biotin. Preferably, the second biotin is derivatized with L-E. Thus, cell membranes can be labeled with biotin-G, contacted with avidin or streptavidin to provide a cell-biotin-avidin complex, and the complex then further contacted with biotinylated cleavable linker attached to an electrophoretic tags. The cleavable linker that is biotinylated can be the same or can be different than the cleavable linker attached to avidin or streptavidin. Thus, multiple cleavable linkers that are cleaved under different conditions can be used to study different reactions with the same cell membrane, liposome or micelle. Biotinylated electrophoretic tags of the form, biotin-L-E, are disclosed in U.S. patent publication 2003/0013126 dated Jan. 16, 2003, which is incorporated herein by reference.

Figure 1C:
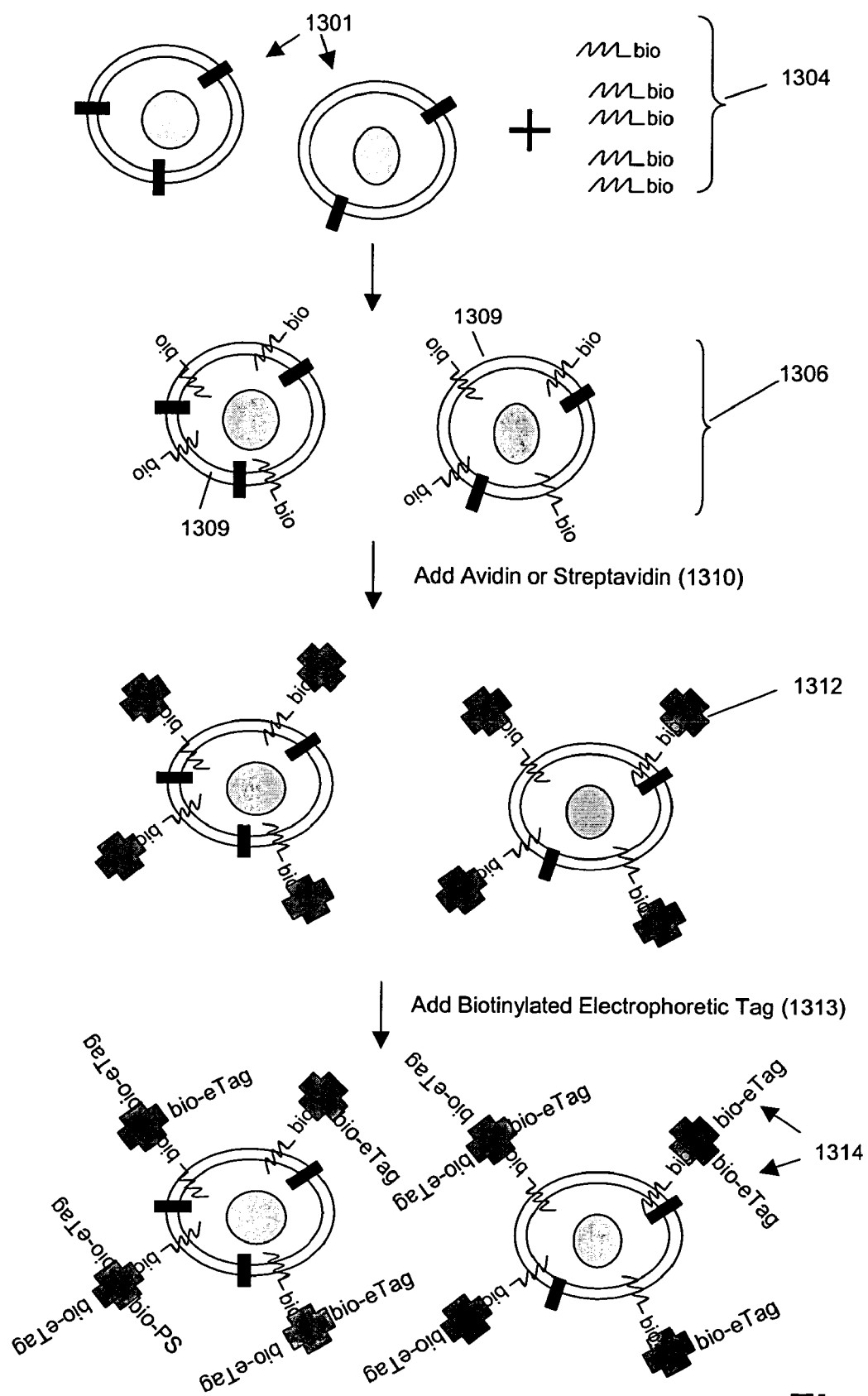
FIG. 1C illustrates the use of biotinylated lipophilic moieties and avidinated electrophoretic tags in accordance with one embodiment of the invention.

The above process is illustrated in FIG. 1C. Cells (1301) are combined with biotin having a lipophilic moiety (1304) (referred to below as biotin-G) to form a population of cells (1306) having membranes containing free biotin. To this population is added avidin or streptavidin (1310) to form biotin-avidin or biotin-streptavidin complexes (1312) on the cell surfaces. These cells are then combined (1313) with biotinylated electrophoretic tag to form complexes (1312) on the cell or membrane surface.

Multiple Electrophoretic Tags

It may be advantageous to have the release of multiple electrophoretic tag reporters for a binding event involving an individual target molecule. In a sense, this results in an amplification of signal. Where the lipophilic moiety has a plurality of sites for attachment such as, for example, multiple functional groups to which L-E can be attached, a plurality of electrophoretic tags can be attached to provide compounds of the structure $G\text{-}(L\text{-}E)_m$. For example, each lipophilic moiety (G) can have attached L-E moieties that result in the release of from 2-1000, preferably from 2-300, and more preferably from 2-100, and still more preferably from about 2 to about 10 molecules of detectable moieties per molecule. Each electrophoretic tag (E) released can be the same or can be different such that each different E is detectable. In another aspect, where the cleavable moiety has a plurality of sites for attachment, a plurality of electrophoretic tags can be attached thereto, thus providing compounds of the structure $G\text{-}L\text{-}(E)_m$.

In another aspect of the invention, the electrophoretic tag moieties are cleavably attached to a hub, to which the lipophilic moiety (G) is also attached. The hub nucleus can be a polyfunctional material, normally polymeric, having a plurality of functional groups, e.g., hydroxy, amino, mercapto, carboxy, ethylenic, aldehyde, etc., as sites for linking. The compounds of this aspect have the formula $G\text{-}P\text{-}(L\text{-}E)_m$, where P is the polyfunctional material comprising the hub. The functionalities on the hub should be those that are reactive with a functionality on the L-E moiety or the G moiety to be attached. Some functionalities are preferred over others because of their ability to resist participation in unwanted side reactions. The hub nucleus is usually at least about 35,000 molecular weight and may be about 10 million or more molecular weight, but usually under about 600,000, more usually under about 300,000. Illustrative hub nuclei include polysaccharides, polypeptides, such as polylysine, polynucleotides, ion exchange resins, and the like. The hub is in one aspect a branched linker, which has multiple sites for attachment of the L-E moieties. Thus, the hub has an attachment site for attaching the lipophilic moiety and a plurality of sites for attachment of a plurality of L-E moieties. In another aspect, such as a branched linker may comprise a streptavidin, or like polyvalent molecule, that is bound to a biotin covalently linked to a lipophilic moiety, G. Multiple electrophoretic tags are attached by cleavable linkages to a biotinylated polymeric backbone, such as aminodextran, which is then attached to the membrane-bound streptavidin through an available biotin binding site.

In one embodiment the hub nucleus is a hydrophilic polymer, generally, an addition or condensation polymer with multiple functionality to permit the attachment of multiple moieties. One class of polymers that is useful for the reagents of the present invention comprises hydrophilic polymers, such as polysaccharide polymers. Polysaccharides such as dextrans, sepharose, polyribose, polyxylose, and the like may be used. Another class of polymers are those that result from the addition polymerization of substituted ethylene or butadiene type monomers, including short chain unsaturated monomers such as propylene, wherein these monomers have substituents that are hydrophilic groups or can be derivatized to hydrophilic groups. Suitable hydrophilic groups that may be attached to the ethylene include hydroxy, carboxy and the ester and amides thereof, amines, and the like. If acrylic acid monomers are used, the acid can be derivatized to suitable reactive groups prior to or subsequent to polymerization. Thus, for example, the ester formed from ethylene glycol and acrylic acid provides a hydroxyl group for derivatization to the components of the e-tag probe. Other suitable polymers include polyallyl amines and alcohols such as, for example, polyvinyl alcohol. In addition to utilizing polymers derived from a single monomer, mixed polymers may also be employed. In this case, the hydrophilicity may be provided by a non-reactive component such as polyethylene glycol, which is then further polymerized to monomers that bear the appropriate functional groups for reaction with the components of the e-tag probe. One such polymer is a copolymer of polyethylene glycol with polyvinyl alcohol. One specific example of a hub is dextran to which about 10 to about 300 molecules of e-tag moieties may be attached per one molecule of dextran.

Accordingly, in the present invention one or more hub molecules can be attached to a lipid bilayer by means of the lipophilic moiety (G). The electrophoretic tag moieties can be attached to the hub by means of a cleavable linkage. Upon exposure to a cleavage-inducing reagent, multiple electrophoretic tag reporters are released for subsequent detection. Depending upon the reagent to which the electrophoretic tag moiety is attached as discussed above, there may be a single electrophoretic tag moiety or a plurality of electrophoretic tag moieties, generally ranging from about 1 to about $10^5$, more usually ranging from about 1 to about 300, more particularly ranging from about 1 to about 20. The number of electrophoretic tag moieties attached to a lipid bilayer depends upon the sensitivity required, the solubility of the electrophoretic tag moiety, the effect on the assay of a plurality of electrophoretic tag moieties, and the like.

Cleavage Agents

As mentioned above, cleavable linkage, L, is cleaved by a cleavage agent that may vary widely depending on several factors including the chemical nature of the cleavable linkage, whether other assay components are stable in the presence of the cleavage agent, whether the membrane anchored electrophoretic probes are used in a homogeneous or non-homogeneous assay format, and the like. In a non-homogeneous assay format, where the linkages sought to be cleaved are separated from those that are intended to remain intact, cleavage agents may include acids, bases, oxidants, including singlet oxygen, hydrogen peroxide, and the like, reductants, light, enzymes, including proteases and nucleases, nucleophilic reagents, and the like. In such formats, after separation, selection of cleavage reagent depends on the chemical nature of the cleavable linkage, the stability of the released electrophoretic tag in the presence of the cleavage agent, the affect of side products created in the cleavage step on the electrophoretic separation and detection of the electrophoretic tags, and the like. Generally, in a non-homogeneous format the cleavage agent, such as a photosensitizer or enzyme, need not be attached to a binding agent to localizing its action. On the other hand, in a homogeneous format, a cleavage agent must act only in the proximity of the cleavable linkages intended to be cleaved. Preferably, this is accomplished by attaching a cleavage agent to a binding agent, such as an antibody, antibody binding composition, or the like. As used herein, the term "cleavage-inducing moiety" refers to a cleavage agent that is attached to a binding agent for the purpose of localizing the cleavage effects of the cleavage agent.

In one aspect, a cleavage-inducing moiety is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background beyond the proximity of its creation, or a quencher compound is employed that efficiently reacts with the active species, so that it is not available to react with cleavable linkages beyond a short distance from the site of its generation. Illustrative active species include singlet oxygen, hydrogen peroxide, NADH, and hydroxyl radicals, phenoxy radical, superoxide, and the like. Illustrative quenchers for active species that cause oxidation include polyenes, carotenoids, vitamin E, vitamin C, amino acid-pyrrole N-conjugates of tyrosine, histidine, and glutathione, and the like, e.g. Beutner et al., Meth. Enzymol., 319: 226-241 (2000).

An important consideration for the cleavage-inducing moiety and the cleavable linkage is that they not be so far removed from one another when bound to a target protein that the active species generated by the sensitizer diffuses and loses its activity before it can interact with the cleavable linkage. Accordingly, a cleavable linkage preferably are within 1000 nm, preferably 20-100 nm of a bound cleavage-inducing moiety. This effective range of a cleavage-inducing moiety is referred to herein as its "effective proximity."

Generators of active species include enzymes, such as oxidases, such as glucose oxidase, xanthene oxidase, D-amino acid oxidase, NADH-FMN oxidoreductase, galactose oxidase, glyceryl phosphate oxidase, sarcosine oxidase, choline oxidase and alcohol oxidase, that produce hydrogen peroxide, horse radish peroxidase, that produces hydroxyl radical, various dehydrogenases that produce NADH or NADPH, urease that produces ammonia to create a high local pH. One cleavable linkage can be based on the oxidation of sulfur or selenium, where a thioether, sulfoxide, or selenium analog thereof, is present at the $\alpha$- or $\beta$-position in relation to an activating group, which makes the hydrogen $\alpha$ to the activating group acidic and capable of being removed by base, so as to release the oxidized functionality to which is attached the releasable portion of the e-tag, or to be subject to oxidation with release of the e-tag. Alternatively, one may use metal chelates that are stable at one oxidation state and unstable at another oxidation state. Other compounds include $\alpha$-substituted methylquinones, which have the releasable portion of a reagent bonded through a leaving group, such as sulfonyl, oxy, amino, etc.

A sensitizer is a molecule, usually a compound, that can be induced to generate a reactive intermediate, or species, usually singlet oxygen. Preferably, a sensitizer used in accordance with the invention is a photosensitizer. However, other sensitizers can be employed in the present invention such as, for example, chemi-activated (e.g., enzymes and metal salts) including, by way of example and not limitation, other substances and compositions that can produce singlet oxygen with or, less preferably, without activation by an external light source. Thus, for example, molybdate $(MoO_4^=)$ salts and chloroperoxidase and myeloperoxidase plus bromide or chloride ion have been shown to catalyze the conversion of hydrogen peroxide to singlet oxygen and water. For the above examples of sensitizers, hydrogen peroxide may be included as an ancillary reagent, chloroperoxidase may be bound to a surface and molybdate may be incorporated in the aqueous phase of a liposome, respectively. Other sensitizers included within the scope of the invention are compounds that are not true sensitizers but which on excitation by heat, light, ionizing radiation, or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed in the following references: Di Mascio et al, FEBS Lett., 355: 287 (1994) (peroxidases and oxygenases); Kanofsky, J. Biol. Chem. 258: 5991-5993 (1983) (lactoperoxidase); Pierlot et al, Meth. Enzymol., 319: 3-20 (2000) (thermal lysis of endoperoxides); and the like.

Attachment of a binding agent, such as an antibody, to the cleavage-inducing moiety may be direct or indirect, covalent or non-covalent and can be accomplished by well-known techniques, commonly available in the literature. See, for example, "Immobilized Enzymes," Ichiro Chibata, Halsted Press, New York (1978); Cuatrecasas, J. Biol. Chem., 245: 3059 (1970). A wide variety of functional groups are available or can be incorporated. Functional groups include carboxylic acids, aldehydes, amino groups, cyano groups, ethylene groups, hydroxyl groups, mercapto groups, and the like. The manner of linking a wide variety of compounds is well known and is amply illustrated in the literature (see above). The length of a linking group to a binding agent may vary widely, depending upon the nature of the compound being linked, the effect of the distance on the specific binding properties and the like.

It may be desirable to have multiple cleavage-inducing moieties attached to a binding agent to increase, for example, the number of active species generated. In one approach the binding agent has a plurality of sites for attachment such as, for example, an antibody, a lectin, and so forth. To further enhance the number of cleavage-inducing moieties, a hub molecule or nucleus is employed. The hub nucleus is a polyfunctional material, normally polymeric, having a plurality of functional groups, e.g., hydroxy, amino, mercapto, carboxy, ethylenic, aldehyde, etc., as sites for linking. An exemplary hub material is aminodextran which may be attached to binding agents, such as antibodies, using well-known techniques. Preferably, NHS-esters of cleavage-inducing moieties are then reacted with the aminodextran for attachment.

Photosensitizers as Cleavage-Inducing Moieties

As mentioned above, the preferred cleavage-inducing moiety in accordance with the present invention is a photosensitizer that produces singlet oxygen. As used herein, "photosensitizer" refers to a light-adsorbing molecule that when activated by light converts molecular oxygen into singlet oxygen. Photosensitizers may be attached directly or indirectly, via covalent or non-covalent linkages, to the binding agent of a class-specific reagent. Guidance for constructing of such compositions, particularly for antibodies as binding agents, available in the literature, e.g. in the fields of photodynamic therapy, immunodiagnostics, and the like. The following are exemplary references: Ullman, et al., Proc. Natl. Acad. Sci. USA 91, 5426-5430 (1994); Strong et al, Ann. New York Acad. Sci., 745: 297-320 (1994); Yarmush et al, Crit. Rev. Therapeutic Drug Carrier Syst., 10: 197-252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516,636; and the like.

Likewise, there is guidance in the literature regarding the properties and selection of photosensitizers suitable for use in the present invention. The following are exemplary references: Wasserman and R. W. Murray. Singlet Oxygen. (Academic Press, New York, 1979); Baumstark, Singlet Oxygen, Vol. 2 (CRC Press Inc., Boca Raton, Fla. 1983); and Turro, Modern Molecular Photochemistry (University Science Books, 1991).

The photosensitizers are sensitizers for generation of singlet oxygen by excitation with light. The photosensitizers include dyes and aromatic compounds, and are usually compounds comprised of covalently bonded atoms, usually with multiple conjugated double or triple bonds. The compounds typically absorb light in the wavelength range of about 200 to about 1,100 nm, usually, about 300 to about 1,000 nm, preferably, about 450 to about 950 nm, with an extinction coefficient at its absorbance maximum greater than about 500 $M^{-1}$ $cm^{-1}$, preferably, about 5,000 $M^{-1}$ $cm^{-1}$, more preferably, about 50,000 $M^{-1}$ $cm^{-1}$, at the excitation wavelength. The lifetime of an excited state produced following absorption of light in the absence of oxygen will usually be at least about 100 nanoseconds, preferably, at least about 1 millisecond. In general, the lifetime must be sufficiently long to permit cleavage of a linkage in a reagent in accordance with the present invention. Such a reagent is normally present at concentrations as discussed below. The photosensitizer excited state usually has a different spin quantum number (S) than its ground state and is usually a triplet (S=1) when the ground state, as is usually the case, is a singlet (S=0). Preferably, the photosensitizer has a high intersystem crossing yield. That is, photoexcitation of a photosensitizer usually produces a triplet state with an efficiency of at least about 10%, desirably at least about 40%, preferably greater than about 80%.

Photosensitizers chosen are relatively photostable and, preferably, do not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3-6 of the periodic table, especially iodine or bromine, or they may have extended aromatic structures.

A large variety of light sources are available to photoactivate photosensitizers to generate singlet oxygen. Both polychromatic and monchromatic sources may be used as long as the source is sufficiently intense to produce enough singlet oxygen in a practical time duration. The length of the irradiation is dependent on the nature of the photosensitizer, the nature of the cleavable linkage, the power of the source of irradiation, and its distance from the sample, and so forth. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include, by way of illustration and not limitation, lasers such as, e.g., helium-neon lasers, argon lasers, YAG lasers, He/Cd lasers, and ruby lasers; photodiodes; mercury, sodium and xenon vapor lamps; incandescent lamps such as, e.g., tungsten and tungsten/halogen; flashlamps; and the like.

Examples of photosensitizers that may be utilized in the present invention are those that have the above properties and are enumerated in the following references: Turro, Modem Molecular Photochemistry (cited above); Singh and Ullman, U.S. Pat. No. 5,536,834; Li et al, U.S. Pat. No. 5,763,602; Ullman, et al., Proc. Natl. Acad. Sci. USA 91, 5426-5430 (1994); Strong et al, Ann. New York Acad. Sci., 745: 297-320 (1994); Martin et al, Methods Enzymol., 186: 635-645 (1990); Yarmush et al, Crit. Rev. Therapeutic Drug Carrier Syst., 10: 197-252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516, 636; Wohrle, Chimia, 45: 307-310 (1991); Thetford, European patent publ. 0484027; Sessler et al, SPIE, 1426: 318-329 (1991); Madison et al, Brain Research, 522: 90-98 (1990); Polo et al, Inorganica Chimica Acta, 192: 1-3

(1992); Demas et al, J. Macromol. Sci., A25: 1189-1214 (1988); and the like. Exemplary photosensitizers are listed in Table 1.

TABLE 1

Exemplary Photosensitizers

| | |
|---|---|
| Hypocrellin A | Tetraphenylporphyrin |
| Hypocrellin B | Halogenated derivatives of rhodamine dyes |
| Hypericin | metallo-Porphyrins |
| Halogenated derivatives of fluorescein dyes | Phthalocyanines |
| Rose bengal | Naphthalocyanines |
| Merocyanine 540 | Texaphyrin-type macrocycles |
| Methylene blue | Hematophorphyrin |
| 9-Thioxanthone | 9,10-Dibromoanthracene |
| Chlorophylls | Benzophenone |
| Phenaleone | Chlorin e6 |
| Protoporphyrin | Perylene |
| Benzoporphryin A monacid | Benzoporphryin B monacid |

Synthesis of G-L-E Compounds

The compounds of the invention comprise the lipophilic group (G), the cleavable linkage (L), and the electrophoretic group (E), as described above. The compounds of the present invention, having the structure G-L-E, can be synthesized using techniques and materials known to those of skill in the art, such as described, for example, in March, ADVANCED ORGANIC CHEMISTRY $4^{th}$ Ed., (Wiley 1992); Carey and Sundberg, ADVANCED ORGANIC CHEMISTY $3^{rd}$ Ed., Vols. A and B (Plenum 1992), and Green and Wuts, PROTECTIVE GROUPS IN ORGANIC SYNTHESIS $2^{nd}$ Ed. (Wiley 1991). Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Apin Chemicals, Ltd. (New Brunswick, N.J.), Ryan Scientific (Columbia, S.C.), Maybridge (Cornwall, England) and Trans World Chemicals (Rockville, Md.).

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1H$ and $^{13}C$ NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts.

The chemistry for performing the types of syntheses to form the charge-imparting moiety or mobility modifier as a peptide chain is well known in the art. See, for example, Marglin, et al., Ann. Rev. Biochem. (1970) 39:841-866. In general, such syntheses involve blocking, with an appropriate protecting group, those functional groups that are not to be involved in the reaction. The free functional groups are then reacted to form the desired linkages. The peptide can be produced on a resin as in the Merrifield synthesis (Merrifield, J. Am. Chem. Soc. (1980) 85:2149-2154 and Houghten et al., Int. J. Pep. Prot. Res. (1980) 16:311-320. The peptide is then removed from the resin according to known techniques.

A summary of the many techniques available for the synthesis of peptides may be found in J. M. Stewart, et al., "Solid Phase Peptide Synthesis, W. H. Freeman Co, San Francisco (1969); and J. Meienhofer, "Hormonal Proteins and Peptides", (1973), vol. 2, p. 46, Academic Press (New York), for solid phase peptide synthesis; and E. Schroder, et al., "The Peptides", vol. 1, Academic Press (New York), 1965 for solution synthesis.

In general, these methods comprise the sequential addition of one or more amino acids, or suitably protected amino acids, to a growing peptide chain. Normally, a suitable protecting group protects either the amino or carboxyl group of the first amino acid. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide. The protecting groups are removed, as desired, according to known methods depending on the particular protecting group utilized. For example, the protecting group may be removed by reduction with hydrogen and palladium on charcoal, sodium in liquid ammonia, etc.; hydrolysis with trifluoroacetic acid, hydrofluoric acid, and the like.

For synthesis of electrophoretic tag probes employing phosphoramidite, or related chemistry, many guides are available in the literature: Handbook of Molecular Probes and Research Products, $8^{th}$ edition (Molecular Probes, Inc., Eugene, Oreg., 2002); Beaucage and Iyer, Tetrahedron, 48: 2223-2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Many of these chemistries allow components of the electrophoretic probe to be conveniently synthesized on an automated DNA synthesizer, e.g. an Applied Biosystems, Inc. (Foster City, Calif.) model 392 or 394 DNA/RNA Synthesizer, or the like.

Synthesis of electrophoretic tag reagents comprising nucleotides as part of the mobility-modifying moiety can be easily and effectively achieved via assembly on a solid phase support using standard phosphoramidite chemistries. The resulting mobility modifying moiety may be linked to the label and/or polypeptide-binding moiety as discussed above.

The aforementioned label conjugates with different electrophoretic mobility permit a multiplexed detection of multiple polypeptides having induced binding sites. It is, of course, within the purview of the present invention to prepare any number of label conjugates for performing multiplexed determinations. Representative compounds of the invention are illustrated in FIG. 6.

The Membrane

The membranes for use in the practice of the invention can be obtained from cells, such as a cellular membrane, nuclear membrane, mitochondrial membrane, or other intracellular membrane, or can be artificially created, as exemplified by micelles and liposomes. The cell(s) used in the methods described herein can be of any origin, including from prokaryotes, eukaryotes, or archeons, but preferably contain membranes that are lipophilic. The cell(s) may be living or dead. If obtained from a multicellular organism, the cell may be of any cell type. Thus, the cell(s) may be a cultured cell line or a primary isolate, the cell(s) may be mammalian, amphibian, reptilian, plant, yeast, bacterium, spirochetes, or protozoan. The cell(s) may be, for example, human, murine, rat, hamster, chicken, quail, goat or dog. The cell may be a normal cell, a mutated cell, a genetically manipulated cell, a tumor cell, hybridomas that are positive for secretion of selected antibodies, and the like. Of particular interest are membranes obtained from the type of cell that differentially expresses (over-expresses or under-expresses) a disease-causing gene. As is apparent to one skilled in the art, various cell lines, such as CHO, for example, may be obtained from public or private repositories. T he largest depository agent is American Type Culture Collection (http://www.atcc.org), which offers a diverse collection of well-characterized cell lines derived from a vast number of organisms and tissue samples.

Exemplary cell types from multicellular organisms include acidophils, acinar cells, pinealocytes, adipocytes, ameloblasts, astrocytes, basal (stem) cells, basophils, hepatocytes, neurons, bulging surface cells, C cells, cardiac muscle cells, centroacinar cells, chief cells, chondrocytes, Clara cells, columnar epithelial cells, corpus luteal cells, decidual cells, dendrites, endrocrine cells, endothelial cells, enteroendocrine cells, eosinophils, erythrocytes, extraglomerular mesangial cells, fetal fibroblasts, fetal red blood cells, fibroblasts, follicular cells, ganglion cells, giant Betz cells, goblet cells, hair cells, inner hair cells, type I hair cells, hepatocytes, endothelial cells, Leydig cells, lipocytes, liver parenchymal cells, lymphocytes, lysozyme-secreting cells, macrophages, mast cells, megakaryocytes, melanocytes, mesangial cells, monocytes, myoepithelial cells, myoid cells, neck mucous cells, nerve cells, neutrophils, oligodendrocytes, oocytes, osteoblasts, osteochondroclasts, osteoclasts, osteocytes, pillar cells, sulcal cells, parathyroid cells, parietal cells, pepsinogen-secreting cells, pericytes, pinealocytes, pituicytes, plasma cells, platelets, podocytes, spermatocytes, Purkinje cells, pyramidal cells, red blood cells, reticulocytes, Schwann cells, Sertoli cells, columnar cells, skeletal muscle cells, smooth muscle cells, somatostatin cells, enteroendocrine cells, spermatids, spermatogonias, spermatozoas, stellate cells, supporting Deiter cells, support Hansen cells, surface cells, surface epithelial cells, surface mucous cells, sweat gland cells, T lymphocytes, theca lutein cells, thymocytes, thymus epithelial cell, thyroid cells, transitional epithelial cells, type I pneumonocytes, and type II pneumonocytes.

Cell membranes can also be obtained from cell type that is associated with a particular disease or with a specific disease stage. The association with a particular disease or disease stage may be established by the cell=s aberrant behavior in one or more biological processes such as cell cycle regulation, cell differentiation, apoptosis, chemotaxsis, cell motility and cytoskeletal rearrangement. A disease cell may also be confirmed by the presence of a pathogen causing the disease of concern (e.g. HIV for AIDS and HBV for hepatitis B). The types of diseases involving abnormal functioning of specific types of cells may include but are not limited to autoimmune diseases, cancer, obesity, hypertension, diabetes, neuronal and/or muscular degenerative diseases, cardiac diseases, endocrine disorders, and any combinations thereof. Exemplary types of tumor cells include adenomas, carcinomas, adenocarcinomas, fibroadenomas, ameloblastomas, astrocytomas, mesotheliomas, cholangiocarcinomas, cholangiofibromas, cholangiomas, chondromas, chondrosarcomas, chordomas, choriocarcinomas, craniopharyngiomas, cystadenocarcinomas, cystadenomas, dysgerminomas, ependymomas, epitheliomas, erythroid leukemias, fibroadenomas, fibromas, fibrosarcomas, gangliogliomas, ganglioneuromas, ganglioneuroblastomas, gliomas, granulocytic leukemias, hemangiomas, hemangiopericytomas, hemangiosarcomas, hibemomas, histiocytomas, keratoacanthomas, leiomyomas, leiomyosarcomas, lipomas, liposarcomas, luteomas, lymphangiomas, lymphangiosarcomas, lymphomas, medulloblastomas, melanomas, meningiomas, mesotheliomas, myelolipomas, nephroblastomas, neuroblastomas, neuromyoblastomas, odontomas, oligodendrogliomas, osteochondromas, osteomas, osteosarcomas, papillomas, paragangliomas, pheochromocytomas, pinealomas, pituicytomas, retinoblastomas, rhabdomyosarcomas, sarcomas, schwannomas, seminomas, teratomas, thecomas and thymomas.

In another aspect of the invention, the membrane comprises liposomes. "Liposomes" are self-assembling structures comprising one or more lipid bilayers. Liposomes are usually composed of phospholipid bilayers, although other molecules, such as cholesterol or fatty acids can also be included in the bilayer construction. The phospholipid constituents of liposomes includes a hydrophobic lipid tail connected to a head constructed of various glycerylphophate or silicone derivatives. Liposomes are thus normally made from amphipathic lipids comprise a polar (hydrophilic) headgroup region covalently linked to one or two non-polar (hydrophobic) acyl chains. Energetically unfavorable contacts between the hydrophobic acyl chains and the aqueous medium are generally believed to induce lipid molecules to rearrange such that the polar headgroups are oriented towards the aqueous medium while the acyl chains reorient towards the interior of the bilayer. An energetically stable structure is formed in which the acyl chains are effectively shielded from coming into contact with the aqueous medium. The hydrophobic interaction between the fatty acid tails thus creates the liposomal bilayers in aqueous solutions. In more complicated liposomal structures, one or more of the lipid bilayers can surround an aqueous compartment and comprises two opposing monolayers of amphipathic lipid molecules. Liposomes are thus completely closed bilayer membranes containing an encapsulated aqueous phase. Thus, liposomes may be any variety of multilamellar vesicles (concentric membrane bilayers each separated by an aqueous layer) or unilamellar vesicles (possessing a single membrane bilayer).

The liposomes may be prepared according to the method of Bangham et al. (1965) J. Mol. Biol. 13: 238-252, in which phospholipids were suspended in an organic solvent which was then evaporated to dryness leaving a waxy deposit of phospholipid on the reaction vessel. Then an appropriate amount of aqueous phase was added, the mixture was allowed to swell, and the resulting liposomes which consisted of multilamellar vesicles were dispersed by mechanical means. The structure of the resulting membrane bilayer is such that the hydrophobic (non-polar) "tails" of the lipid orient toward the center of the bilayer while the hydrophilic (polar) "heads" orient towards the aqueous phase. This technique provided the basis for the development of the small sonicated unilamellar vesicles described by Papahadjopoulos and Miller (1967) Biochim. Biophys. Acta. 135: 624-638. Normally, mixtures of phospholipids in aqueous solution will spontaneously associated to form liposomal structures, although techniques for controlling the size and shape of the liposomes are known in the art.

Labeling Membranes with G-L-Es

The compounds of the invention, having the structure G-(L-E)$_m$, can be attached to the cells, liposomes, etc. by incorporation into the bilayer. Without being bound by theory, the G-(L-E)$_m$ compounds can be incorporated into the lipid membranes in an orientation and manner similar to that of phospholipids where the hydrophobic moiety comprising of the hydrocarbon chains can orient inward and the more hydrophilic entities L-E can orient outwards. Thus, as in the usual cellular membranes, the hydrocarbon portion of the inventive compounds can be incorporated into the lipid environment whereas the hydrophilic L-E can be exposed to the aqueous interface at the membrane surface. The compounds of the invention can thus be incorporated into the membranes where the cleavable linkage and the electrophoretic moiety are exposed on the surface of the membrane and are accessible to the cleavage reagent, such as singlet oxygen, described above. The compounds of the invention can also be used to label liposomes. Useful liposomes include cationic phospholipids, neutral phospholipids, lipids and mixtures thereof.

Where intact cellular structures are required, the methods used to label the cells preferably cause minimal disruption of the cell and of the integrity of membranes. In addition, the cells can be fixed and treated with routine histochemical or cytochemical procedures, where the procedure preferably does not affect the labeling. Additional components may be included, such as targeting peptides or proteins, fusion peptides (e.g., from Sendai virus, influenza virus, hemagluttinating virus of Japan (HVJ)), envelope proteins of viruses, polycationic substances such as poly-L-lysine or DEAE-dextran, molecules which bind to the surface of airway epithelial cells including antibodies, adhesion molecules and growth factors, and the like.

The membranes can be labeled with the compounds of the invention according to the method described in Barak and Webb (1981) J. Cell Biol. 90:595-604. Typically, the membrane, such as the intact cell, is contacted with the compounds of the invention, preferably in an aqueous media. The aqueous media can be water, water and organic solvent, such as DMSO, DMF, DMA, or a mixture thereof, and can contain buffers such as phosphate, acetate, tris, and the like. The membranes and compounds having the structure G-L-E are contacted for between 1 min. to about 1 week, preferably about 1 h to 76 h, more preferably about 2 h to about 48 h, or any integer in between. The formulations may additionally be subjected to chemical or mechanical treatment, such as the addition of a surfactant (Tween 80, for example), shaking, stirring, electroporation, and the like. Alternatively, the formulation can be heated to about 30° C. to 50° C., preferably about 35° C. to about 40° C., until labeling is achieved. After labeling, the unbound components can be removed by washing, or by centrifugation, for example, and the labeled membranes isolated.

Endocytosis

Figure 4A:
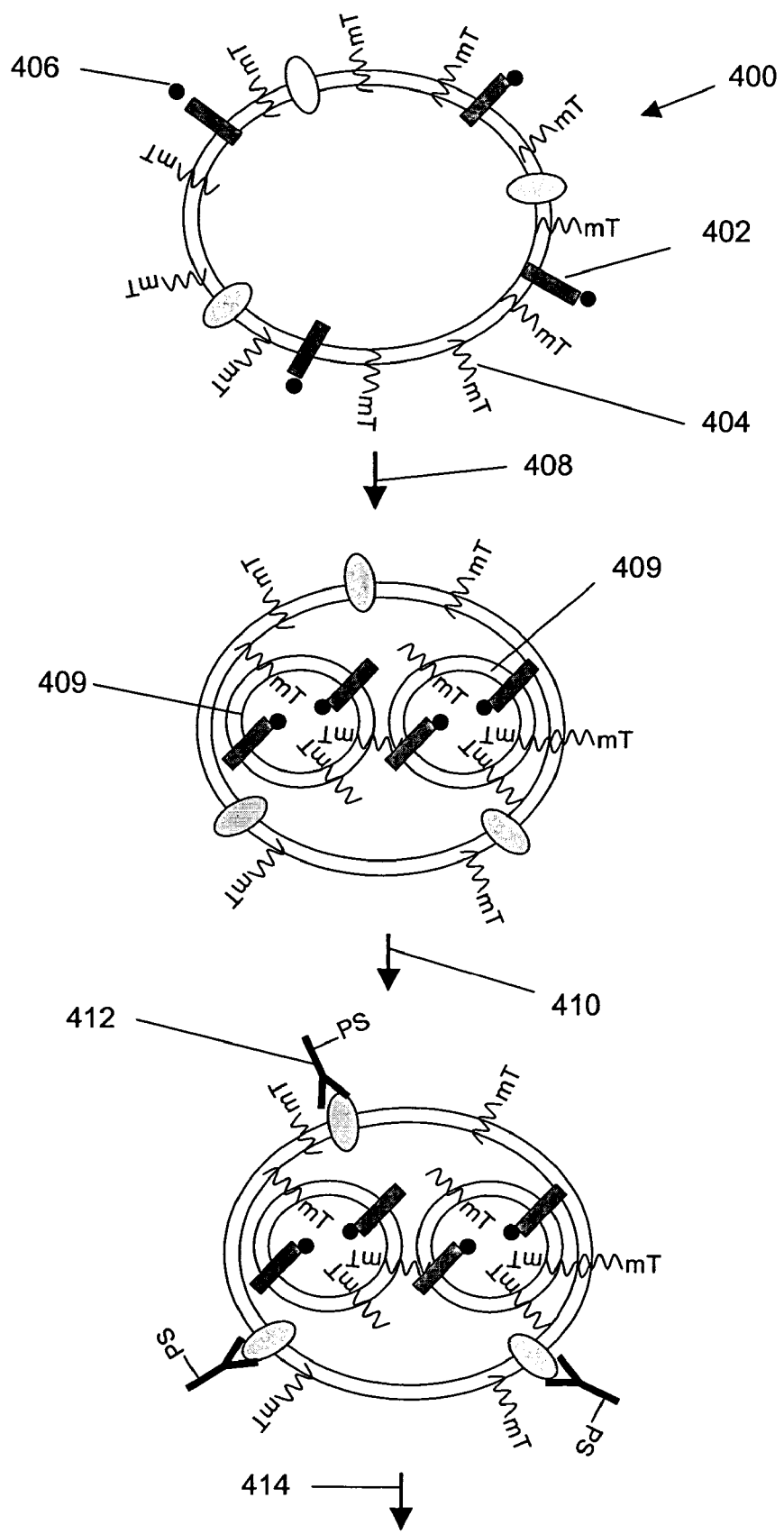
FIGS. 4A-4C illustrate the ligand induced internalization of the lipophilic electrophoretic compounds that are incorporated into the cell membranes.
Figure 4B:
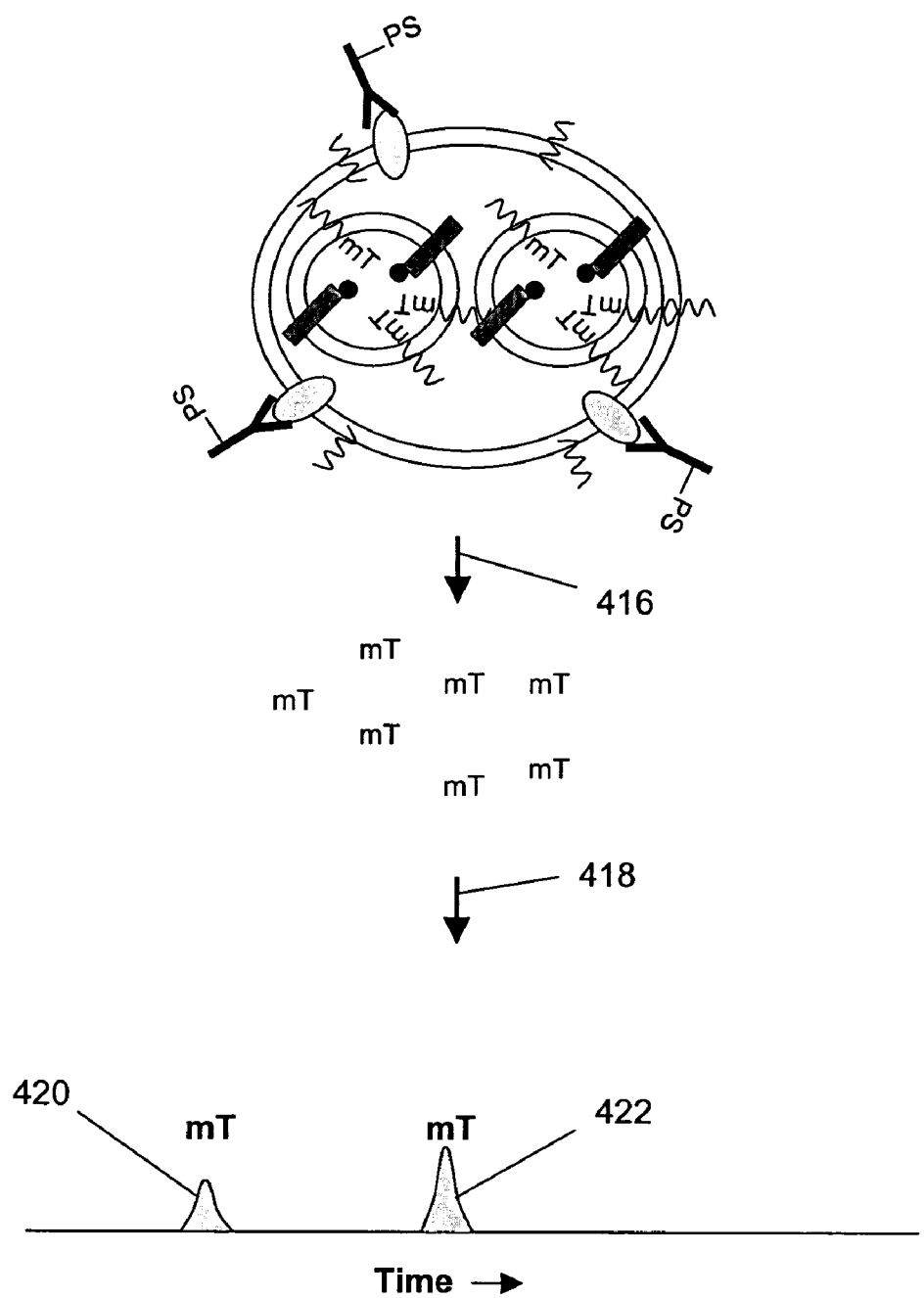

In one aspect of the invention, the lipophilic compounds of the invention, such as G-L-E, G-(L-E)$_m$, biotin-G, and the like, once incorporated into the lipid bilayer, may be endocytosed, or swallowed up, by the cells (FIGS. 4A-4B). Adsorbed lipophilic compounds can also exchange lipids with cell membranes. Endocytosis of lipophilic compounds occurs in cells that are phagocytic, or able to ingest foreign particles. When phagocytic cells take up lipophilic compounds, the cells move them into subcellular organelles known as lysosomes, where the lipophilic compounds can be degraded. Alternatively, lipid exchange involves the transfer of individual lipid molecules from the lipophilic compounds into the plasma membrane (and vice versa). Thus, once lipophilic compounds join the cell membrane, they can either remain in the membrane for a long time or be redistributed to a variety of intracellular membranes.

In one aspect of the invention, the lipophilic compounds can be introduced into the interior of the cells by exposing the cell to a molecule recognized by a receptor on the surface of the cell and allowing an active uptake procedure to occur (e.g., receptor mediated endocytosis) or by forcing the lipophilic compounds into the cell, such as by transient permeabilization or by high speed injection. Thus, the receptor ligand of choice in this instance can be interferons, MIP-1α, MIP-1β, RANTES, MDC, I-309, eotaxin, MCP-3, SDF-1, IL-12, PF4, folate, vitamins, insulin, galactose, EGF, VCAM, ICAM, HIV 120/41, and the like.

The cells with internalized lipophilic compounds can be subjected to an assay. The initial sample of cells having lipophilic compounds of the invention incorporated in their membranes can be grown in the presence or absence of a selective force (e.g., heat, ultraviolet light, osmotic stress, shear stress, selective media, a cytostatic or cytotoxic agent, and the like). After a certain growth period (for example, from 1 minute to 1 week depending on the cell type and type of assay being performed) the number of cells bearing the diluted label can be determined.

Nonlimiting examples of artificial means for transporting lipophilic compounds across cell membranes include action of chemical agents such as detergents, enzymes or adenosine triphosphate; receptor- or transport protein-mediated uptake; phagocytosis; pore-forming proteins; microinjection; electroporation; hypoosmotic shock; or minimal physical disruption such as scrape loading, or patch clamp methods (see, U.S. Pat. Nos. 4,743,548, 4,795,855, 5,068,193, 5,188,958, 5,463,174, 5,565,346 and 5,565,347).

One method for introducing lipophilic compounds into cells employs the use of peptides that encourage entry of lipophilic compounds into the cell, e.g., the HIV-Tat peptide that facilitates viral passage into cells; the Tat peptide has been used to introduce magnetic nanoparticles into mammalian cells. The cells labeled with the lipophilic compounds of the invention can be exposed to Tat peptide sequences alone or along with other peptides, oligonucleotide or other affinity molecule. Incubation of the labeled cells with the peptides allows the lipophilic compounds to enter the cell, probably via endocytosis.

Still another method for introducing the lipophilic compounds into the cells uses the process of receptor-mediated endocytosis. Thus, cell membranes labeled with the lipophilic compounds can be exposed to proteins to trigger receptor-mediated endocytosis. The proteins can include a ligand train to induce receptor-mediated endocytosis (e.g., transferrin) and proteins that induce fusion to the endosome under acidic conditions e.g., hemagglutinin, or some portion of such a proteins that is sufficient to generate its activity. The ligand used for receptor-mediated endocytosis can also act as a specific cell-targeting agent. The lipophilic compounds incorporated into the cellular membranes will be deposited into the cytoplasm of the target cells.

In another method, the lipophilic compounds of the invention can be incorporated into cells by forming pores in the cells. The pores can be formed by, for example, electroporation, osmotic shock, or by the use of a porogen. Electroporation is a common method for introducing foreign material, such as DNA, into cells (see Hui, 1995, Methods in Molecular Biology, Chapter 2, 48:2940). The electroporation method of the invention consists of delivering high voltage pulses to cells thereby making pores in the cell membrane to facilitate the transport of lipophilic compounds into cells. The electroporation process consists of two major steps: reversible breakdown of the cell membranes, and recovery of permeablized cells. Thus, the electrical and incubation parameters are optimized to facilitate the transfer of lipophilic compounds across the membrane. In general, cells labeled with the lipophilic compounds (from 1 to $10^{10}$ cells) can be placed in an electroporation cuvette. The cuvette is then connected to an appropriate power supply and the cells are subjected to a high voltage pulse of defined magnitude and length. The voltage, capacitance and resistance can be varied appropriately depending on the cells or efficiency of the protocol. For example the voltage can be varied between about 1 V to about 100 kV, preferably 1 to 5 kV), the capacitance can be varied between about 0.1 µf to about 100 f, preferably between about 1 µf to about 50 µf, and the resistance can be varied from about 0.1 Ω to about infinity. Cells should then be allowed to recover in the appropriate medium and successfully transfected cells can be assessed using the appropriate detection systems.

Alternatively, porogen can be digitonin, saporin, or a member of the complement cascade. Cells may be permeabilized with digitonin as described in Hagstrom et al. (1997) *J. Cell. Sci.* 110:2323-31, and in Sterne-Marr et al. (1992) *Meth. Enzymol.* 219:97-111, to allow the lipophilic compounds on the cell membrane to be incorporated into the cell.

Figure 4C:
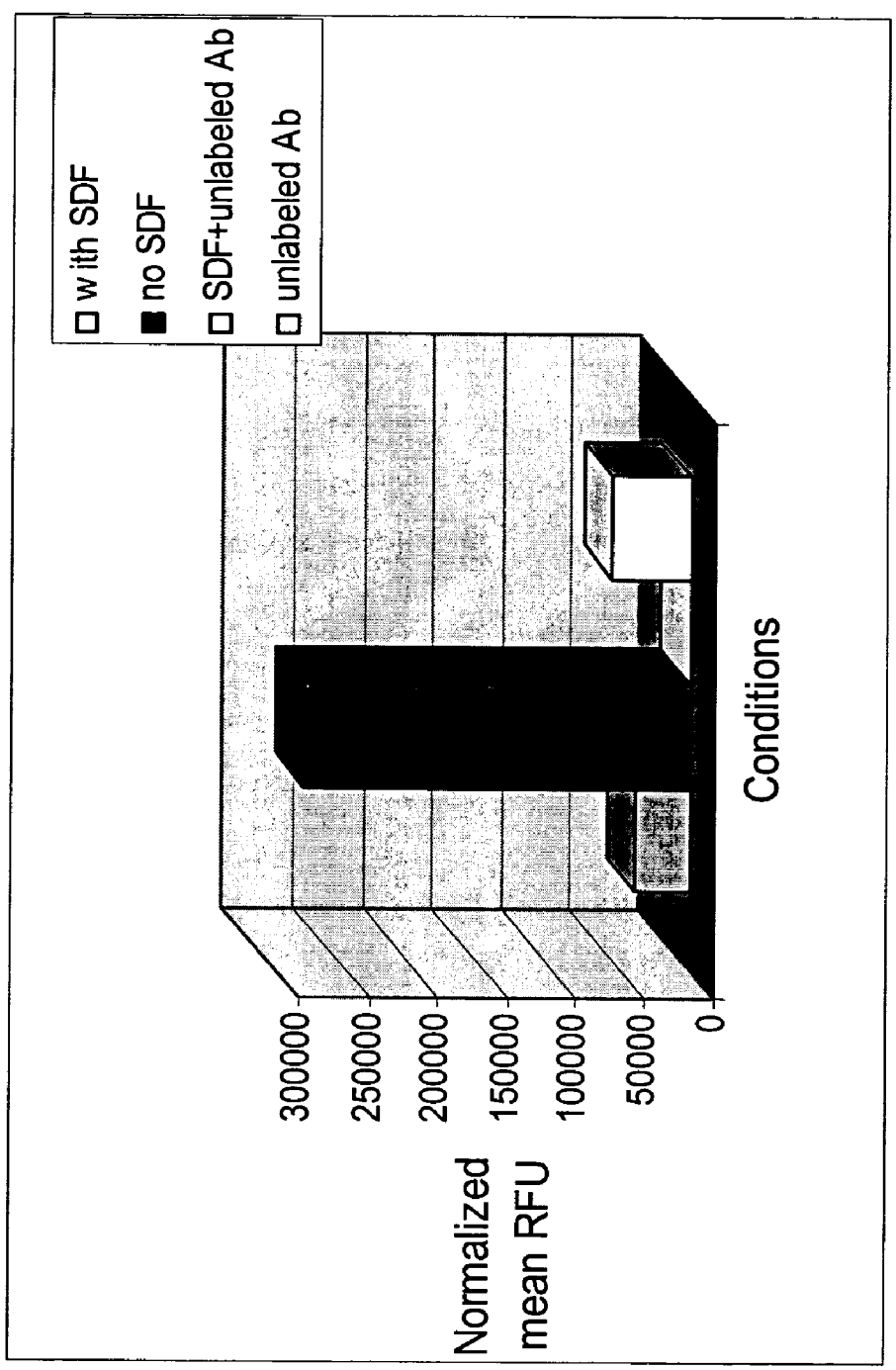
Figure 5A:
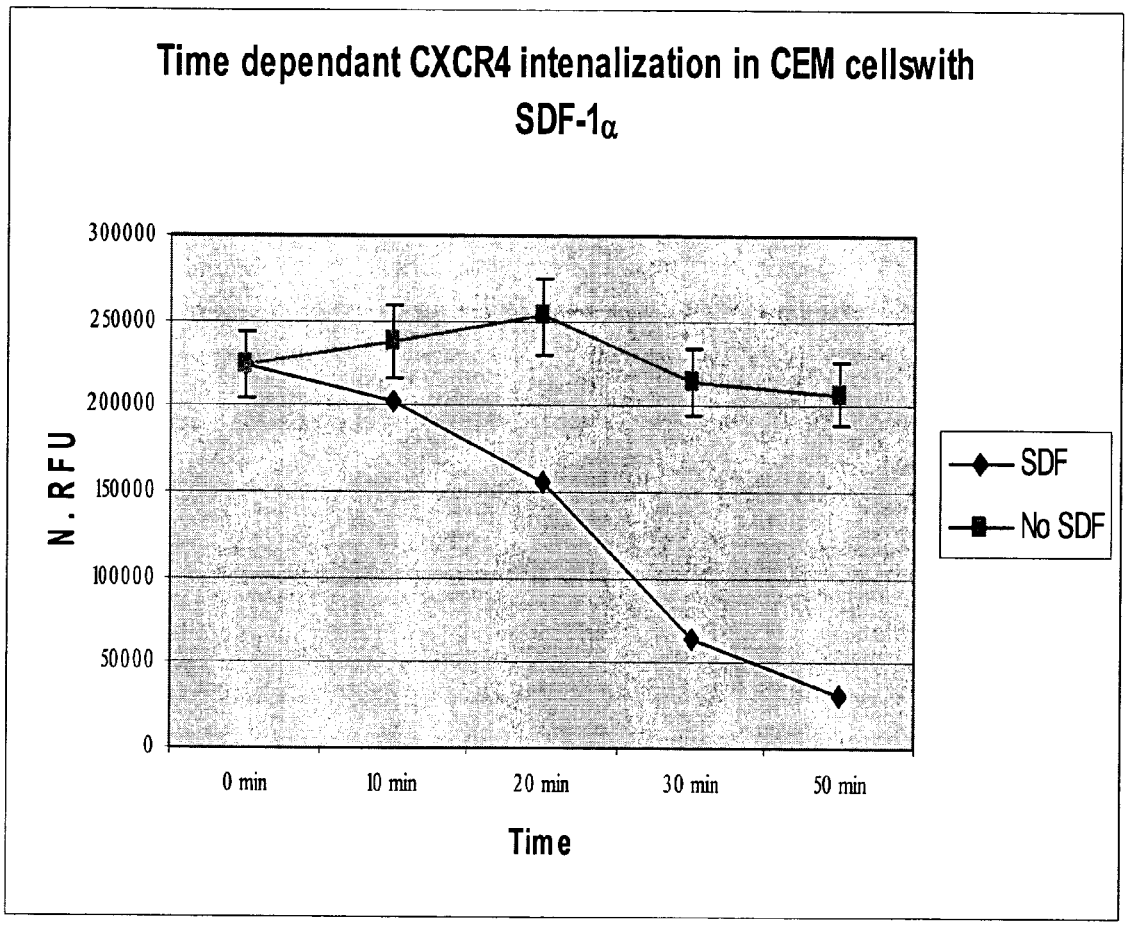
FIGS. 5A-5B depict the rate of internalization of the labeling compounds as a function of time and as a function of concentration of the ligand.
Figure 5B:
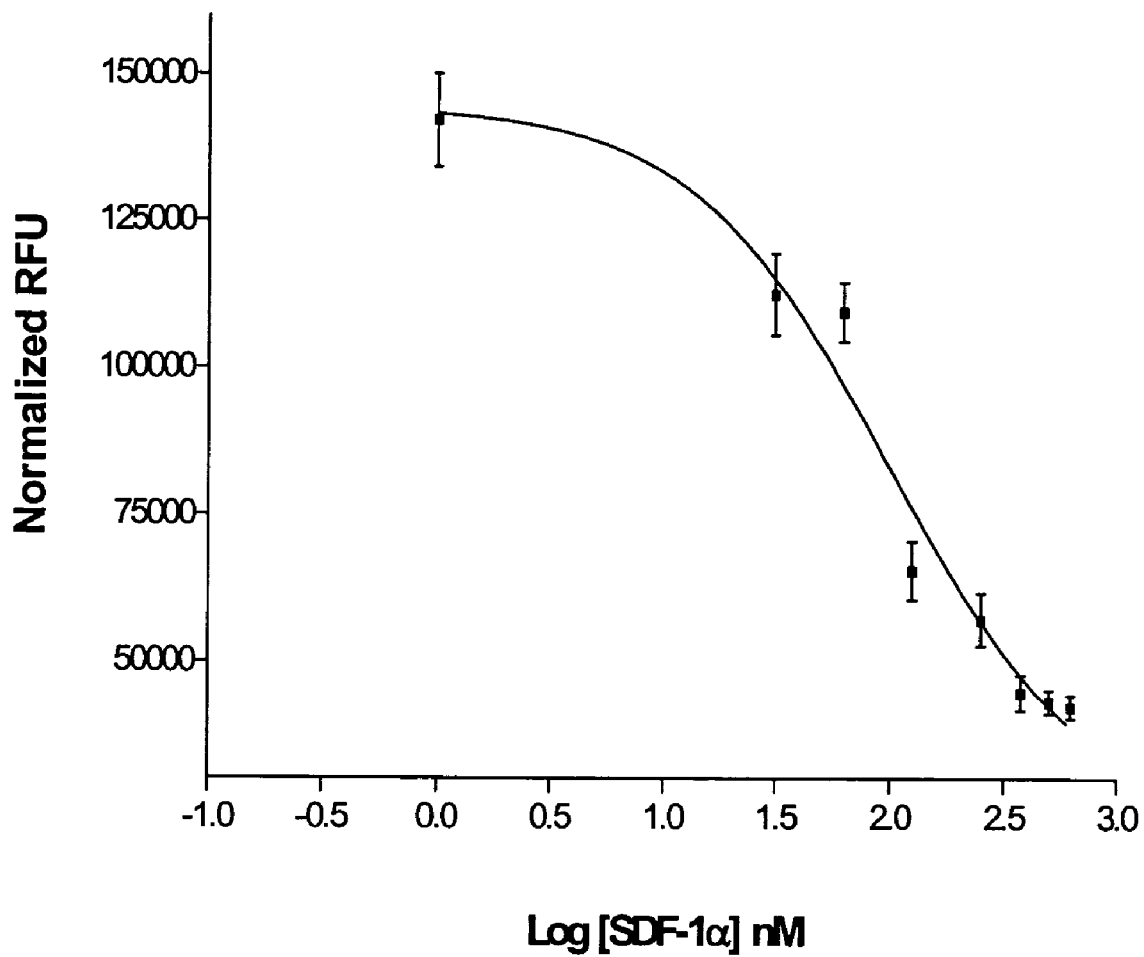
Figure 6A:
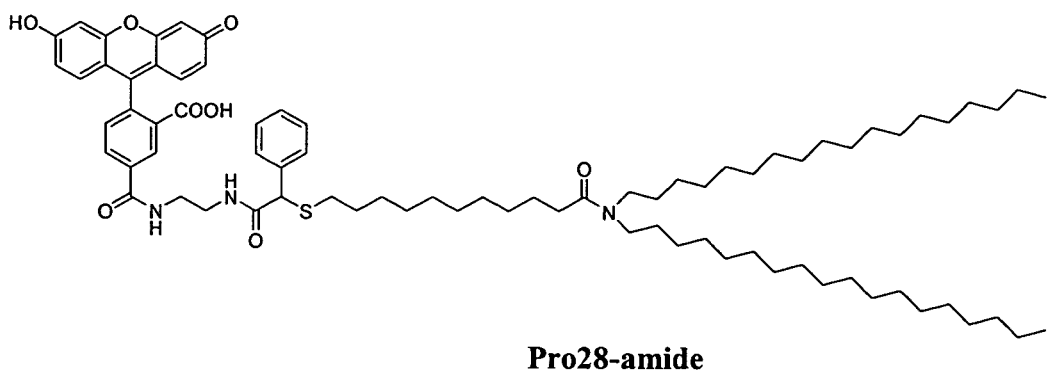
FIGS. 6A-6B illustrate several compounds of the invention.
Figure 6A:
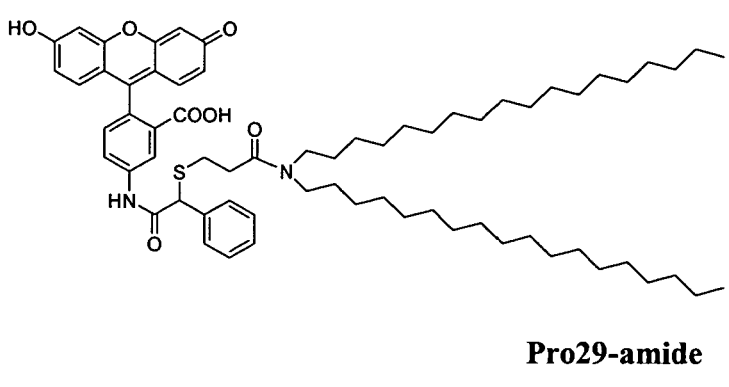
Figure 6A:
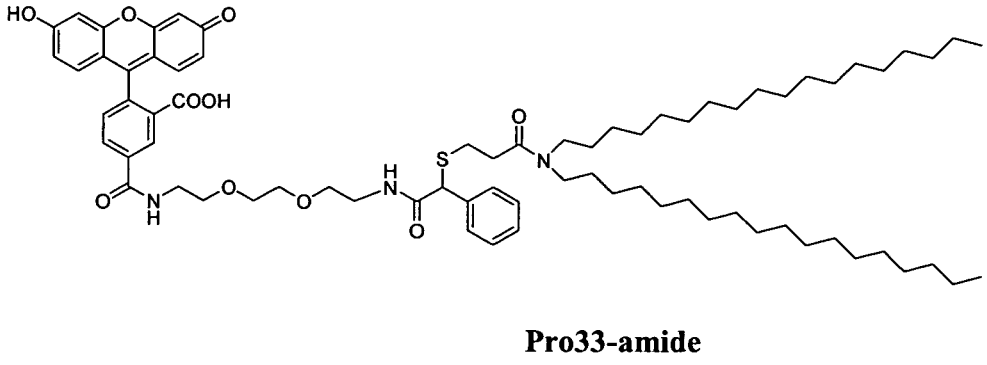
Figure 6A:
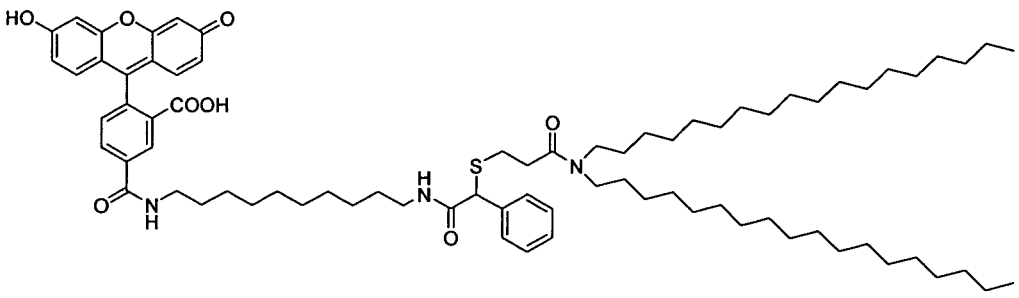
Figure 6B:
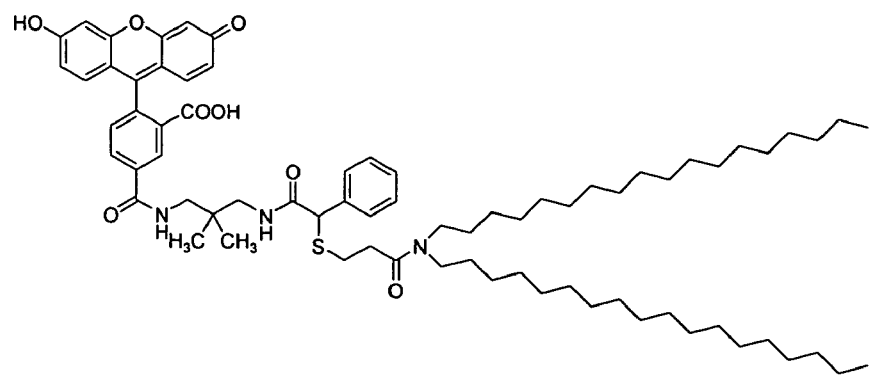
Figure 6B:
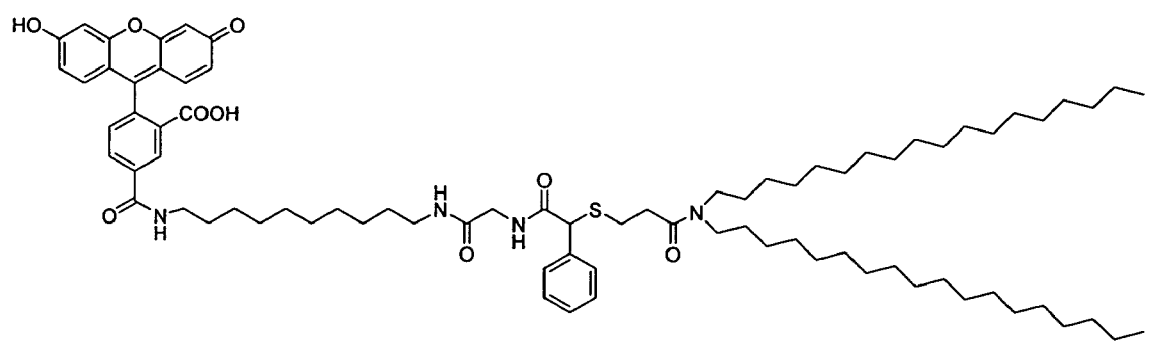
Figure 7A:
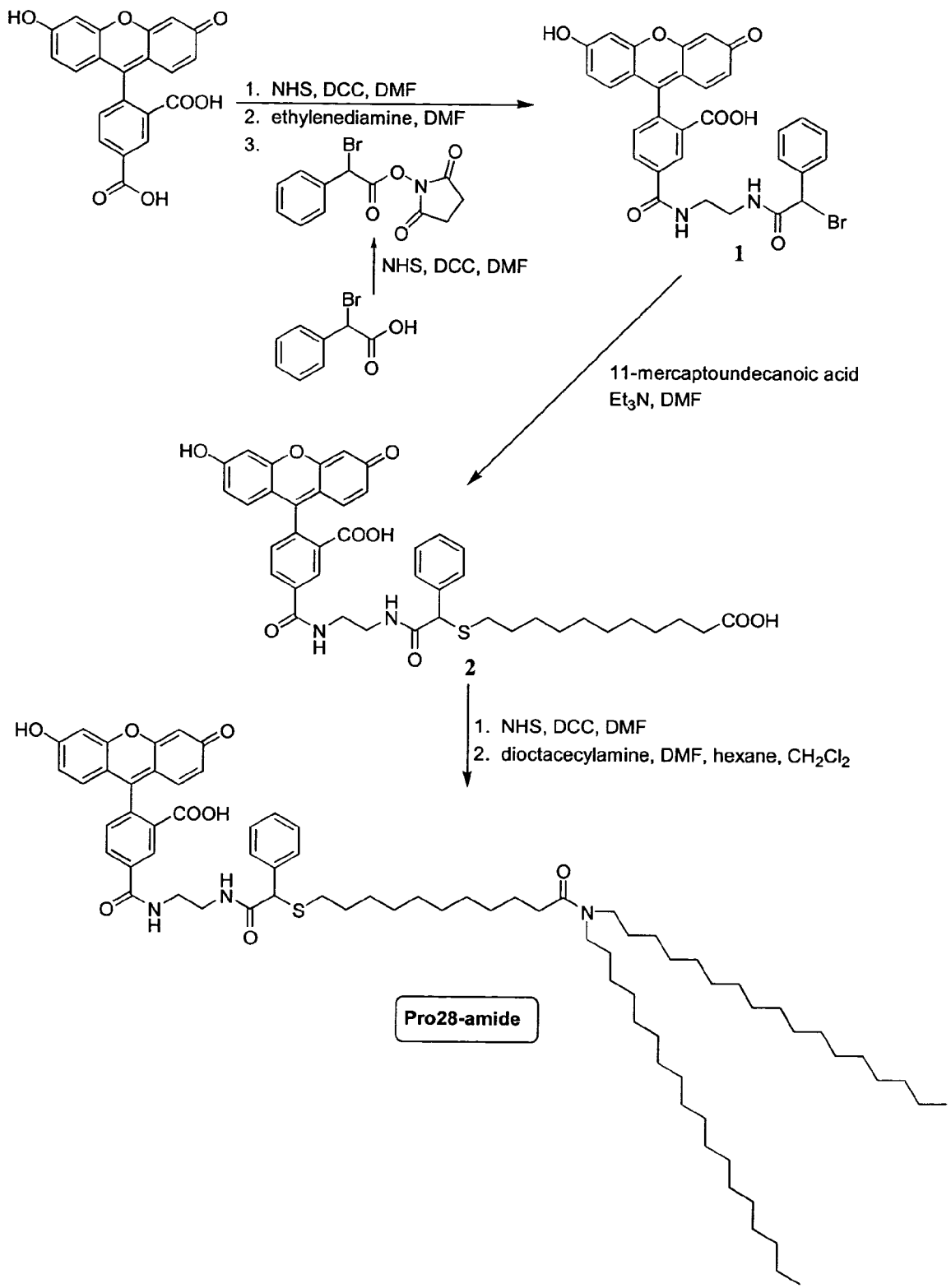
FIGS. 7A-7C illustrate synthetic schemes for compounds of the invention.
Figure 7B:
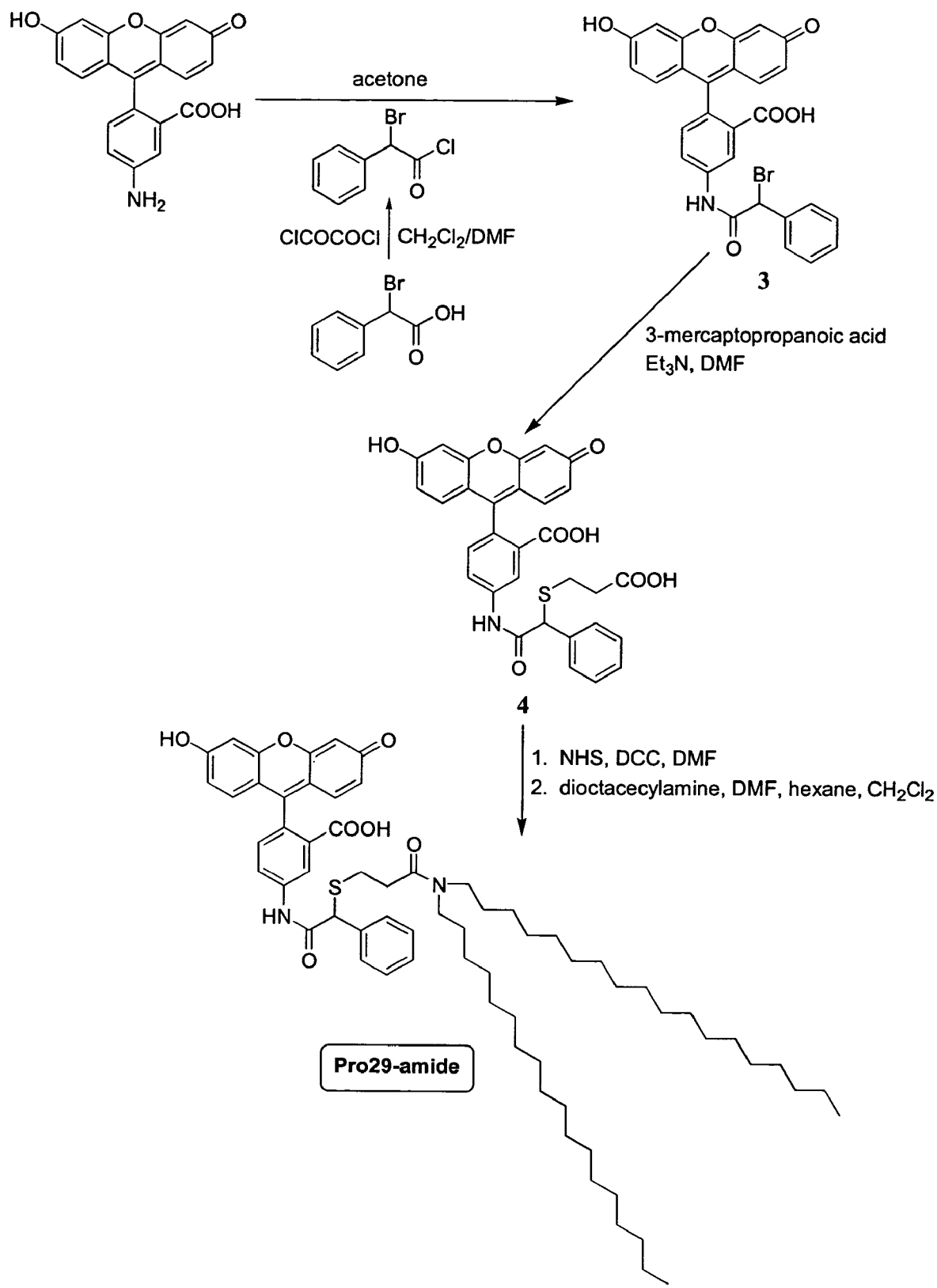
Figure 7C:
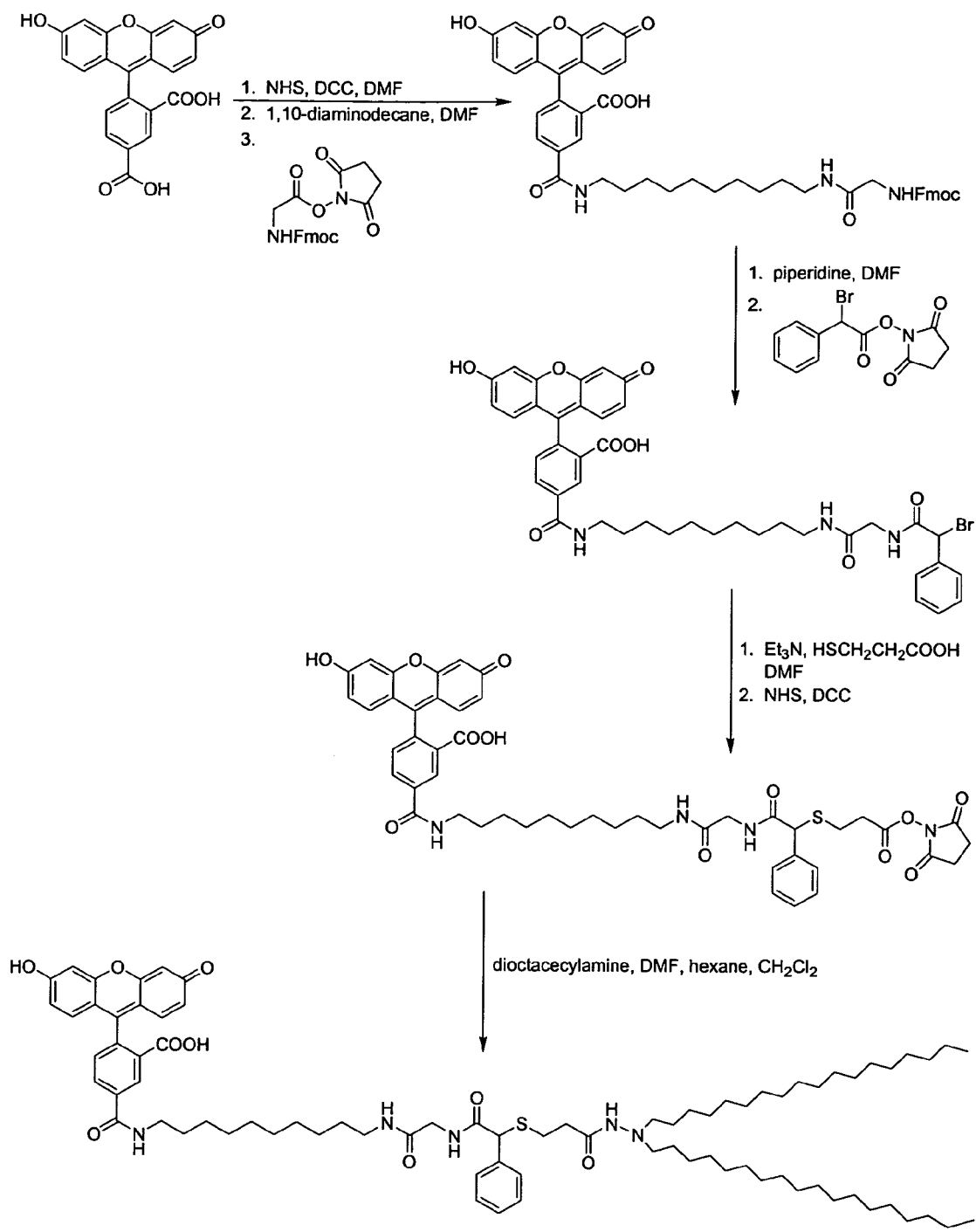

In an example of the invention illustrated in FIGS. 4A-4C, CEM cells (400) expressing CXCR4 (402) are contacted with the lipophilic compounds of the invention, such as G-L-E or G-(L-E)$_m$ (404, where E is denoted "mT" in the figure). CXCR4, the receptor for the CXC/ELR-chemokine stromal cell-derived factor-1 (SDF-1) (406), is found on endothelial cells. Mice lacking CXCR4 or lacking SDF-1 have defective vasculogenesis. The lipophilic group (G) becomes incorporated into the cellular membrane of the cells, and the electrophoretic tags ("mT") are exposed on the surface (FIG. 4A). The labeled CEM cells (400) are then contacted with SDF-1α (406), thereby causing the internalization (408) of some of the G-L-E or G-(L-E)$_m$. The SDF-1α exposed cells are then contacted (410) with and an antibody (412) having a photosensitizer attached. This may be a biotinylated anti-CXCR antibody. After such antibody binds to its cell surface target, it is exposed to light (414) to release (416) the electrophoretic tags. The amount of the electrophoretic tag released in the presence of the ligand SDF-1α can be determined after separation (418) by electrophoresis by quantifying the peak (422) formed by such separation. This quantity can be compared to the amount of the electrophoretic tag released in the absence of the ligand (control). The comparison may be made by comparing peaks (420 and 422) on an electropherogram corresponding to the two experimental circumstances, or the released tags may be quantified separately and then compared. The results, shown in FIGS. 5A and 5B, indicate that the amount of tag released is lower when the cells are exposed to the SDF-1α ligand, and the amount decreases with increasing length of exposure to the ligand and with increasing concentration of the ligand. The results show that the lipohilic compounds incorporated into the cellular membrane of CEM cells are internalized when the cells are exposed to the ligand.

Separation of Released Electrophoretic Tags

As mentioned above, electrophoretic tags are designed for separation by a separation technique that can distinguish electrophoretic tags based on one or more physical, chemical, and/or optical characteristics. Preferably, such separation technique is capable of providing quantitative information as well as qualitative information about the presence or absence of electrophoretic tags (and therefore, corresponding analytes). In one aspect, a liquid phase separation technique is employed so that a solution, e.g. buffer solution, reaction solvent, or the like, containing a mixture of electrophoretic tags is processed to bring about separation of individual kinds of electrophoretic tags.

Usually, such separation is accompanied by the differential movement of electrophoretic tags from such a starting mixture along a path until discernable peaks or bands form that correspond to regions of increased concentration of the respective electrophoretic tags. Such a path may be defined by a fluid flow, electric field, magnetic field, or the like. The selection of a particular separation technique depends on several factors including the expense and convenience of using the technique, the resolving power of the technique given the chemical nature of the electrophoretic tags, the number of electrophoretic tags to be separated, the type of detection mode employed, and the like. Preferably, electrophoretic tags are electrophoretically or chromatographically separated.

A. Electrophoretic Separation

Methods for electrophoresis of are well known and there is abundant guidance for one of ordinary skill in the art to make design choices for forming and separating particular pluralities of electrophoretic tags. The following are exemplary references on electrophoresis: Krylov et al, Anal. Chem., 72: 11 IR-128R (2000); P. D. Grossman and J. C. Colburn, Capillary Electrophoresis: Theory and Practice, Academic Press, Inc., NY (1992); U.S. Pat. Nos. 5,374,527; 5,624,800; 5,552,028; ABI PRISM 377 DNA Sequencer User's Manual, Rev. A, January 1995, Chapter 2 (Applied Biosystems, Foster City, Calif.); and the like. In one aspect, electrophoretic tags are separated by capillary electrophoresis. Design choices within the purview of those of ordinary skill include but are not limited to selection of instrumentation from several commercially available models, selection of operating conditions including separation media type and concentration, pH, desired separation time, temperature, voltage, capillary type and dimensions, detection mode, the number of electrophoretic tags to be separated, and the like.

In one aspect of the invention, during or after electrophoretic separation, the electrophoretic tags are detected or identified by recording fluorescence signals and migration times (or migration distances) of the separated compounds, or by constructing a chart of relative fluorescent and order of migration of the electrophoretic tags (e.g., as an electropherogram). To perform such detection, the electrophoretic tags can be illuminated by standard means, e.g. a high intensity mercury vapor lamp, a laser, or the like. Typically, the electrophoretic tags are illuminated by laser light generated by a He—Ne gas laser or a solid-state diode laser. The fluorescence signals can then be detected by a light-sensitive detector, e.g., a photomultiplier tube, a charged-coupled device, or the like. Exemplary electrophoresis detection systems are described elsewhere, e.g. U.S. Pat. Nos. 5,543, 026; 5,274,240; 4,879,012; 5,091,652; 6,142,162; or the like. In another aspect, electrophoretic tags may be detected electrochemically detected, e.g. as described in U.S. Pat. No. 6,045,676.

Electrophoretic separation involves the migration and separation of molecules in an electric field based on differences in mobility. Various forms of electrophoretic separation include, by way of example and not limitation, free zone electrophoresis, gel electrophoresis, isoelectric focusing, isotachophoresis, capillary electrochromatography, and micellar electrokinetic chromatography. Capillary electrophoresis involves electroseparation, preferably by electrokinetic flow, including electrophoretic, dielectrophoretic and/or electroosmotic flow, conducted in a tube or channel of from about 1 to about 200 micrometers, usually, from about 10 to about 100 micrometers cross-sectional dimensions. The capillary may be a long independent capillary tube or a channel in a wafer or film comprised of silicon, quartz, glass or plastic.

In capillary electroseparation, an aliquot of the reaction mixture containing the electrophoretic tags is subjected to electroseparation by introducing the aliquot into an electroseparation channel that may be part of, or linked to, a capillary device in which the amplification and other reactions are performed. An electric potential is then applied to the electrically conductive medium contained within the channel to effectuate migration of the components within the combination. Generally, the electric potential applied is sufficient to achieve electroseparation of the desired components according to practices well known in the art. One skilled in the art will be capable of determining the suitable electric potentials for a given set of reagents used in the present invention and/or the nature of the cleaved labels, the nature of the reaction medium and so forth. The parameters for the electroseparation including those for the medium and the electric potential are usually optimized to achieve maximum separation of the desired components. This may be achieved empirically and is well within the purview of the skilled artisan.

Detection may be by any of the known methods associated with the analysis of capillary electrophoresis columns including the methods shown in U.S. Pat. Nos. 5,560,811 (column 11, lines 19-30), U.S. Pat. Nos.4,675,300, 4,274,240 and 5,324,401, the relevant disclosures of which are incorporated herein by reference. Those skilled in the electrophoresis arts will recognize a wide range of electric potentials or field strengths may be used, for example, fields of 10 to 1000 V/cm are used with about 200 to about 600 V/cm being more typical. The upper voltage limit for commercial systems is about 30 kV, with a capillary length of about 40 to about 60 cm, giving a maximum field of about 600 V/cm. For DNA, typically the capillary is coated to reduce electroosmotic flow, and the injection end of the capillary is maintained at a negative potential.

For ease of detection, the entire apparatus may be fabricated from a plastic material that is optically transparent, which generally allows light of wavelengths ranging from about 180 to about 1500 nm, usually about 220 to about 800 nm, more usually about 450 to about 700 nm, to have low transmission losses. Suitable materials include fused silica, plastics, quartz, glass, and so forth.

B. Chromatographic Separation

In one aspect of the invention, pluralities of electrophoretic tags are designed for separation by chromatography based on one or more physical characteristics that include but are not limited to molecular weight, shape, solubility, pKa, hydrophobicity, charge, polarity, or the like. A chromatographic separation technique is selected based on parameters such as column type, solid phase, mobile phase, and the like, followed by selection of a plurality of electrophoretic tags that may be separated to form distinct peaks or bands in a single operation. Several factors determine which HPLC technique is selected for use in the invention, including the number of electrophoretic tags to be detected (i.e. the size of the plurality), the estimated quantities of each electrophoretic tag that will be generated in the assays, the availability and ease of synthesizing electrophoretic tags that are candidates for a set to be used in multiplexed assays, the detection modality employed, and the availability, robustness, cost, and ease of operation of HPLC instrumentation, columns, and solvents. Generally, columns and techniques are favored that are suitable for analyzing limited amounts of sample and that provide the highest resolution separations. Guidance for making such selections can be found in the literature, e.g. Snyder et al, Practical HPLC Method Development, (John Wiley & Sons, New York, 1988); Millner, "High Resolution Chromatography: A Practical Approach", Oxford University Press, New York (1999), Chi-San Wu, "Column Handbook for Size Exclusion Chromatography", Academic Press, San Diego (1999), and Oliver, "HPLC of Macromolecules: A Practical Approach, Oxford University Press", Oxford, England (1989). In particular, procedures are available for systematic development and optimization of chromatographic separations given conditions, such as column type, solid phase, and the like, e.g. Haber et al, J. Chromatogr. Sci., 38: 386-392 (2000); Outinen et al, Eur. J. Pharm. Sci., 6: 197-205 (1998); Lewis et al, J. Chromatogr., 592: 183-195 and 197-208 (1992); and the like.

In one aspect, initial selections of electrophoretic tag candidates are governed by the physiochemical properties of molecules typically separated by the selected column and stationary phase. The initial selections are then improved empirically by following conventional optimization procedure, as described in the above reference, and by substituting more suitable candidate electrophoretic tags for the separation objectives of a particular embodiment. In one aspect, separation objectives of the invention include (i) separation of the electrophoretic tags of a plurality into distinguishable peaks or bands in a separation time of less than 60 minutes, and more preferably in less than 40 minutes, and still more preferably in a range of between 10 to 40 minutes, (ii) the formation of peaks or bands such that any pair has a resolution of at least 1.0, more preferably at least 1.25, and still more preferably, at least 1.50, (iii) column pressure during separation of less than 150 bar, (iv) separation temperature in the range of from 25° C. to 90° C., preferably in the range of from 35° C. to 80° C., and (v) the plurality of distinguishable peaks is in the range of from 5 to 30 and all of the peaks in the same chromatogram. As used herein, "resolution" in reference to two peaks or bands is the distance between the two peak or band centers divided by the average base width of the peaks, e.g. Snyder et al (cited above).

A chromatographic method is used to separate electrophoretic tags based on their chromatographic properties. A chromatographic property can be, for example, a retention time of a electrophoretic tag on a specific chromatographic medium under defined conditions, or a specific condition under which a electrophoretic tag is eluted from a specific chromatographic medium. A chromatographic property of a electrophoretic tag can also be an order of elution, or pattern of elution, of a electrophoretic tag contained in a group or set of electrophoretic tags being chromatographically separated using a specific chromatographic medium under defined conditions. A chromatographic property of a electrophoretic tag is determined by the physical properties of the electrophoretic tag and its interactions with a chromatographic medium and mobile phase. Defined conditions for chromatography include particular mobile phase solutions, column geometry, including column diameter and length, pH, flow rate, pressure and temperature of column operation, and other parameters that can be varied to obtain the desired separation of electrophoretic tags. A electrophoretic tag, or chromatographic property of a electrophoretic tag, can be detected using a variety of chromatography methods.

Although standard liquid chromatography methods can be used to separate electrophoretic tags, high pressure (or performance) liquid chromatography (HPLC) provides the advantages of high resolution, increased speed of analysis, greater reproducibility, and ease of automation of instrument operation and data analysis. HPLC methods also allow separation of electrophoretic tags based on a variety of physiochemical properties. Electrophoretic tags having similar properties can be used together in the same experiment since HPLC can be used to differentiate between closely related tags. The high degree of resolution achieved using HPLC methods allows the use of large sets of tagged probes because the resulting electrophoretic tags can be distinguished from each other. The ability to detect large sets of tagged probes is an advantage when performing multiplexed detection of target nucleic acids and target analytes. As used herein, "HPLC" refers to a liquid phase chromatographic separation that (i) employs a rigid cylindrical separation column having a length of up to 300 mm and an inside diameter of up to 5 mm, (ii) has a solid phase comprising rigid spherical particles (e.g. silica, alumina, or the like) having the same diameter of up to 5 μm packed into the separation column, (iii) takes place at a temperature in the range of from 35° C. to 80° C. and at column pressure up to 150 bars, and (iv) employs a flow rate in the range of from 1 μL/min to 4 mL/min. Solid phase particles for use in HPLC are further characterized in (i) having a narrow size distribution about the mean particle diameter, with substantially all particle diameters being within 10% of the mean, (ii) having the same pore size in the range of from 70 to 300 angstroms, (iii) having a surface area in the range of from 50 to 250 $m^2/g$, and (iv) having a bonding phase density (i.e. the number of retention ligands per unit area) in the range of from 1 to 5 per $nm^2$.

Sets of electrophoretic tags detected in a single experiment generally are a group of chemically related molecules that differ by mass, charge, mass-charge ratio, detectable tag, such as differing fluorophores or isotopic labels, or other unique characteristic. Therefore, both the chemical nature of the electrophoretic tag and the particular differences among electrophoretic tags in a group of electrophoretic tags can be considered when selecting a suitable chromatographic medium for separating electrophoretic tags in a sample.

Reverse phase chromatography is a type of chromatography in which the chemically bonded phase is hydrophobic (nonpolar) than the mobile phase. This is "reversed" from normal phase chromatography, in which the stationary phase is hydrophilic (polar), and the starting mobile phase is more nonpolar than the stationary phase. Mobile phase gradients that increase in concentration of an organic modifier (usually acetonitrile or methanol) are commonly used in reverse phase HPLC. These gradients elute solute molecules in order of increasing hydrophobicity. Exemplary mobile phases for use with the invention to separate water soluble electrophoretic tags include but are not limited to water, nitromethane, methanol, dimethyl sulfoxide, dimethylformamide, acetonitrile, acetic acid, methoxyethanol, benzyl alcohol, acetone, and the like. The mobile phases may be used isocratically or they may be combined and delivered to a column in continuously varying proportions. In the latter case, usually two solvents are combined in proportions that vary linearly over time, i.e. gradient delivery.

Various mobile phase additives can be used to provide different selectivity to improve separation of electrophoretic tags. For example, ion pairing reagents may be used in reverse phase HPLC methods. Exemplary ion pairing reagents include trifluoroacetic acid (TFA), which is an anionic ion-pairing reagent, and tetrabutylammonium phosphate, which is a cationic ion pairing reagent.

Reverse phase HPLC can be used to separate a variety of types of electrophoretic tags, including organic molecules, oligonucleotides, peptides and polypeptides. Reversed phase HPLC is particularly useful for separating peptide or polypeptide electrophoretic tags that are closely related to each other. Exemplary reversed phase chromatography media for separating electrophoretic tags include particles, e.g. silica or alumina, having bonded to their surfaces retention ligands, such as phenyl groups, cyano groups, or aliphatic groups selected from the group including $C_8$ through $C_{18}$. Preferably, the particles have a pore size in the range of from 80 to 300 angstroms.

Exemplary reversed phase chromatography media for separating electrophoretic tags that are peptides, include particles having aliphatic retention ligands in the range of from $C_8$ to $C_{18}$ bonded to their surfaces and having a pore size of between 60 and 80 angstroms. Commercial preparations useful for separating electrophoretic tags include, for example, Apex WP Octadecyl $C_{18}$, Octyl $C_{18}$, Butyl $C_4$ and Phenyl, Aquaprep RP-3000 $C_4$ and $C_8$, Bakerbond WP Octadecyl $C_{18}$, Octyl C8, Butyl $C_4$ and Diphenyl.

Prior to separation by HPLC, a sample can be fractionated or subjected to a pre-separation step, for example, to remove particulate matter or molecules other than reporter tags. In addition to standard biochemical methods for fractionating samples, such as centrifugation, precipitation, filtration and extraction, a variety of HPLC pre-columns or guard columns can be used for this purpose.

Separated electrophoretic tags can be detected using a variety of analytical methods, including detection of intrinsic properties of electrophoretic tags, such as absorbance, fluorescence or electrochemical properties, as well as detection of a detection group or moiety attached to a electrophoretic tag. Although not required, a variety of detection groups or moieties can be attached to electrophoretic tags to facilitate detection after chromatographic separation.

Detection methods for use with liquid chromatography are well known, commercially available, and adaptable to automated and high-throughput sampling. The detection method selected for analysis of electrophoretic tags will depend upon whether the electrophoretic tags contain a detectable group or moiety, the type of detectable group used, and the physicochemical properties of the electrophoretic tag and detectable group, if used. Detection methods based on fluorescence, electrolytic conductivity, refractive index, and evaporative light scattering can be used to detect various types of electrophoretic tags.

A variety of optical detectors can be used to detect a electrophoretic tag separated by liquid chromatography. Methods for detecting nucleic acids, polypeptides, peptides, and other macromolecules and small molecules using ultraviolet (UV)/visible spectroscopic detectors are well known, making UV/visible detection the most widely used detection method for HPLC analysis. Infrared spectrophotometers also can be used to detect macromolecules and small molecules when used with a mobile phase that is a transparent polar liquid.

Variable wavelength and diode-array detectors represent two commercially available types of UV/visible spectrophotometers. A useful feature of some variable wavelength UV detectors is the ability to perform spectroscopic scanning and precise absorbance readings at a variety of wavelengths while the peak is passing through the flowcell. Diode array technology provides the additional advantage of allowing absorbance measurements at two or more wavelengths, which permits the calculation of ratios of such absorbance measurements. Such absorbance rationing at multiple wavelengths is particularly helpful in determining whether a peak represents one or more than one electrophoretic tag.

Fluorescence detectors can also be used to detect fluorescent electrophoretic tags, such as those containing a fluorescent detection group and those that are intrinsically fluorescent. Typically, fluorescence sensitivity is relatively high, providing an advantage over other spectroscopic detection methods when electrophoretic tags contain a fluorophore. Although electrophoretic tags can have detectable intrinsic fluorescence, when a electrophoretic tag contains a suitable fluorescent detection group, it can be possible to detect a single electrophoretic tag in a sample.

Electrochemical detection methods are also useful for detecting electrophoretic tags separated by HPLC. Electrochemical detection is based on the measurement of current resulting from oxidation or reduction reaction of the electrophoretic tags at a suitable electrode. Since the level of current is directly proportional to electrophoretic tag concentration, electrochemical detection can be used quantitatively, if desired.

Mass spectrometry methods also can be used to detect electrophoretic tags separated by HPLC. Mass spectrometers can resolve ions with small mass differences and measure the mass of ions with a high degree of accuracy and sensitivity. Mass spectrometry methods are well known in the art (see Burlingame et al. *Anal. Chem.* 70:647R-716R (1998); Kinter and Sherman, Protein Sequencing and Identification Using Tandem Mass Spectrometry Wiley-Interscience, New York (2000)).

Analysis of data obtained using any detection method, such as spectral deconvolution and quantitative analysis can be manual or computer-assisted, and can be performed using automated methods. A variety of computer programs can be used to determine peak integration, peak area, height and retention time. Such computer programs can be used for convenience to determine the presence of a electrophoretic tag qualitatively or quantitatively. Computer programs for use with HPLC and corresponding detectors are well known to those skilled in the art and generally are provided with commercially available HPLC and detector systems.

The particular electrophoretic tags contained in a sample can be determined, for example, by comparison with a database of known chromatographic properties of reference electrophoretic tags, or by algorithmic methods such as chromatographic pattern matching, which allows the identification of components in a sample without the need to integrate the peaks individually. The identities of electrophoretic tags in a sample can be determined by a combination of methods when large numbers of electrophoretic tags are simultaneously identified, if desired.

A variety of commercially available systems are well-suited for high throughput analysis of electrophoretic tags. Those skilled in the art can determine appropriate equipment, such as automated sample preparation systems and autoinjection systems, useful for automating HPLC analysis of electrophoretic tags. Automated methods can be used for high-throughput analysis of electrophoretic tags, for example, when a large number of samples are being processes or for multiplexed application of the methods of the invention for detecting target analytes. An exemplary HPLC instrumentation system suitable for use with the present invention is the Agilent 1100 Series HPLC system (Agilent Technologies, Palo Alto, Calif.).

Those skilled in the art will be aware of quality control measures useful for obtaining reliable analysis of electrophoretic tags, particular when analysis is performed in a high-throughput format. Such quality control measures include the use of external and internal reference standards, analysis of chromatograph peak shape, assessment of instrument performance, validation of the experimental method, for example, by determining a range of linearity, recovery of sample, solution stability of sample, and accuracy of measurement.

In another aspect of the invention, electrophoretic tags are separated by capillary electrochromatography (CEC). In CEC, the liquid phase is driven by electroosmotic flow through a capillary-sized column, e.g. with inside diameters in the range of from 30 to 100 μm. CEC is disclosed in Svec, Adv. Biochem. Eng. Biotechnol. 76: 147 (2002); Vanhoenacker et al, Electrophoresis, 22: 4064-4103 (2001); and like references. CEC column may used the same solid phase materials as used in conventional reverse phase HPLC and additionally may use so-called "monolithic" non-particular packings. In some forms of CEC, pressure as well as electroosmosis drives a sample-containing solvent through a column.

GPCR Pathway Assays

G-protein coupled receptors (GPCRs) represent one of the most important families of drug targets. G protein-mediated signaling systems have been identified in many divergent organisms, such as mammals and yeast. GPCRs respond to, among other extracellular signals, neurotransmitters, hormones, odorants and light. GPCRs are thought to represent a large superfamily of proteins that are characterized by the seven distinct hydrophobic regions, each about 20-30 amino acids in length, that forms the transmembrane domain. The amino acid sequence is not conserved across the entire superfamily, but each phylogenetically related subfamily contains a number of highly conserved amino acid motifs that can be used to identify and classify new members. Individual GPCRs activate particular signal transduction pathways, although at least ten different signal transduction pathways are known to be activated via GPCRs. For example, the beta 2-adrenergic receptor (βAR) is a prototype mammalian GPCR. In response to agonist binding, βAR receptors activate a G protein ($G_s$) which in turn stimulates adenylate cyclase and cyclic adenosine monophosphate production in the cell.

It has been postulated that members of the GPCR superfamily desensitize via a common mechanism involving G protein-coupled receptor kinase (GRK) phosphorylation followed by arrestin binding. The protein β-arrestin regulates GPCR signal transduction by binding agonist-activated receptors that have been phosphorylated by G protein receptor kinases. The β-arrestin protein remains bound to the GPCR during receptor internalization. The interaction between a GPCR and α-arrestin can be measured using several methods. In one example, the β-arrestin protein is fused to green fluorescent protein to create a protein fusion (Barak et al. (1997) *J. Biol. Chem.* 272(44):27497-500). The agonist-dependent binding of β-arrestin to a GPCR can be visualized by fluorescence microscopy. Microscopy can also be used to visualize the subsequent trafficking of the GPCR β-arrestin complex to clathrin coated pits. Other methods for measuring binding of β-arrestin to a GPCR in live cells include techniques such as FRET (fluorescence resonance energy transfer), BRET (bioluminescent energy transfer) or enzyme complementation (Rossi et al. (1997) *Proc. Natl. Acad. Sci. USA* 94(16):8405-10).

At present, there are nearly 400 GPCRs whose natural ligands and function are known. These known GPCRs, named for their endogenous ligands, have been classified into five major categories: Class-A Rhodopsin-like; Class-B Secretin-like; Class-C Metabotropic glutamate/pheromone; Class-D Fungal pheromone; Class-E cAMP (dictyostelium). Representative members of Class-A are the amine receptors (e.g., muscarinic, nicotinic, adrenergic, adenosine, dopamine, histamine and serotonin), the peptide receptors (e.g., angiotensin, bradykinin, chemokines, endothelin and opioid), the hormone receptors (e.g., follicle stimulating, lutropin and thyrotropin), and the sensory receptors, including rhodopsin (light), olfactory (smell) and gustatory (taste) receptors. Representatives of Class-B include secretin, calcitonin, gastrin and glucagon receptors.

Many available therapeutic drugs in use today target GPCRs, as they mediate vital physiological responses, including vasodilation, heart rate, bronchodilation, endocrine secretion, and gut peristalsis (Wilson and Bergsma (2000) Pharm. News 7: 105-114). For example, ligands to β-adrenergic receptors are used in the treatment of anaphylaxis, shock, hypertension, hypotension, asthma and other conditions. Additionally, diseases can be caused by the occurrence of spontaneous activation of GPCRS, where a GPCR cellular response is generated in the absence of a ligand. Drugs that are antagonists of GPCRs decrease this spontaneous activity (a process known as inverse agonism) are important therapeutic agents.

Due to the therapeutic importance of GPCRs, methods for the rapid screening of compounds for GPCR ligand activity are desirable. The present invention provides a method of screening test compounds and test conditions for the ability to modulate (activate or inhibit, enhance or depress) a GPCR pathway, and provides methods of assessing GPCR pathway function, such as the function of an orphan GPCR, in a cell in general. In another aspect of the present method, compounds having the formula G-L-E are attached to the cellular membranes. A candidate ligand or a library of candidate ligands can be attached to a sensitizer or sensitizers, such as photosensitizers that are activated at different wavelengths. The ligand is allowed to bind to the receptor, followed by excitation of the photosensitizer with a light source whereupon the cleavable linker is cleaved releasing the electrophoretic group. The released electrophoretic group can be detected in the extracellular fluid, as detailed above, which is an indication of modulation (inhibition or activation) of GPCR activity or of the presence of a GPCR in a cell, in a cell membrane, and the like.

In another aspect, cells that contain the GPCR receptor can be labeled with the G-L-E compounds of the invention, and the ligand titrated to saturation. The concentration of the unbound ligand can be calculated thereby providing information on the amount of receptors present on the cell surface. If binding is not observed then either the GPCR receptors are not present on the membranes or the ligand is unable to associate with the receptor.

The binding of the ligand may thus be detected by comparing changes in the detectable signal in the same cell over time (i.e., pre- and post-exposure to the test compound or to one or more members of the library of test compounds). Alternatively, a test cell may be compared to a pre-established standard. If a known modulator, e.g., an agonist or antagonist ligand, is available, the present methods can be used to screen a chemical compound library for and study candidate GPCR agonists and antagonists. The methods of the present invention thus provide easily detectable results.

In one aspect, the present invention provides methods for screening modulators of GPCR activity comprising: a) providing a cell expressing a known or unknown GPCR, wherein the cell is labeled with a compound having the formula G-L-E, other detectable label as disclosed herein or combination thereof; b) exposing the cell to a test compound and a cleavage reagent, such as singlet oxygen; c) detecting the signal from the released label; and (d) comparing the signal produced in the presence of the test compound with the signal produced in the absence, wherein changes in the signal indicates that the compound is a modulator of a GPCR. As will be evident, the methods of the invention can be used to permit multiplexed cellular assay simultaneously, such as for example 2-100 fold multiplexing, and more preferably, 2-20 fold multiplexing.

In another aspect, the present invention provides methods for screening candidate GPCR modulator compounds comprising: a) associating the cell or a population of cells with compounds of formula G-L-E and a cleavage-inducing moiety; b) exposing the cell to a predetermined concentration of a test compound or each member of a library of test compounds; c) detecting the signal from the released label and comparing the label signal in the presence and absence of the candidate modulator.

In yet another aspect, the present invention provides methods for screening a cell or a population of cells for the presence of a GPCR, comprising (a) providing a cell or a population of cells; (b) associating the cell or population of cells with membrane anchored electrophoretic probes of the invention; (c) exposing the cell or population of cells to a test solution containing a known agonist to a GPCR; (d) exposing the cell or population of cells to conditions where the cleavable linker is cleaved and the electrophoretic label (E) is released; and (e) detecting the released label, wherein the release of the label indicates the presence of such a GPCR. Preferably, in the above methods, such known antagonist is labeled with a cleavage-inducing moiety, as illustrated in FIG. 1A. Populations of cells to be screened are discussed above, and can additionally include a tissue, an organ, or an organism.

The present invention thus provides a convenient method of identifying modulators for an orphan GPCR. Orphan GPCRs are novel receptors typically identified by sequence comparison-based methods, but whose cognate ligands are not known. It is estimated that from 400 to as many as 5000 orphan GPCRs may be coded for in the human genome, representing a vast potential for developing new drugs.

Preparation of Cells that Express GPCRs

Methods for preparing cells that express GPCRs have been described. See, e.g., U.S. Pat. Nos. 6,051,386, 6,069, 296, 6,111,076 and 6,280,934. Generally, complementary DNA encoding GPCRs can be obtained and can be expressed in an appropriate cell host using techniques well known in the art. Typically, once a full-length GPCR cDNA has been obtained, it can be expressed in a mammalian cell line, yeast cell, amphibian cell or insect cell for functional analysis. Preferably, the cell line is a mammalian cell line that has been characterized for GPCR expression and that optionally contains a wide repertoire of G-proteins to allow functional coupling to downstream effectors. Examples of such cell lines include Chinese Hamster Ovary (CHO) or Human Embryonic Kidney 293 (HEK293) lines. Cells in which the cDNA is expressed can be encoded using the methods disclosed herein, thus allowing the multiplex screening of ligands. The expressed receptor can then be screened in a variety of functional assays to identify an activating ligand as disclosed above.

Kits

Kits comprising reagents useful for performing the methods of the invention are also provided. The components of the kit are retained by a housing. Instructions for using the kit to perform a method of the invention are provided with the housing, and may be located inside the housing or outside the housing, and may be printed on the interior or exterior of any surface forming the housing which renders the instructions legible. In one embodiment, kits of the invention comprise one or more membrane anchored electrophoretic probes of the invention. Preferably, kits of the invention comprise a plurality of from 2 to 100 membrane anchored electrophoretic probes, and more preferably, a plurality of from 2 to 50 membrane anchored electrophoretic probes, such that the electrophoretic probes of a kit each have a releasable electrophoretic tag with electrophoretic and/or optical properties distinct from those of every other electrophoretic tag of the kit. Kits of the invention may provide materials for either homogeneous assay formats or non-homogeneous assay formats. In the former embodiments, kits preferably include a cleavage-inducing moiety bound to, or for binding to, an antibody or antibody binding composition specific for a target molecule of interest to a customer. Such antibody or antibody binding composition may be provided as a component of the kit, or it may be provided by the customer. In further preference, such kits include a photosensitizer bound to an antibody or antibody binding composition. In the latter embodiments, kits of the invention may further include an antibody or antibody binding composition for separating membranes having desired components that such antibody or binding composition is specific for. In such latter embodiments, kit further include a cleavage agent for releasing electrophoretic tags after a separation step. In another embodiment, kits of the invention comprise a plurality of cell lines wherein the membranes of each cell line contains different membrane anchored electrophoretic probes of the invention. Preferably, such plurality comprises from 2 to 100 different cell lines, and more preferably, from 2 to 50 different cell lines, and still more preferably, for 2 to 20 different cell lines. As above, such kits may be provided for either homogeneous or non-homogeneous assay formats, and may comprise the same components as above for releasing electrophoretic tags for separating cell lines with desired properties from other cell lines.

III. Experimental

Below are examples of specific embodiments for carrying out the present invention. The examples are offered for illustrative purposes only, and are not intended to limit the scope of the present invention in any way.

EXAMPLE 1

Synthesis of Lipophilic eTag Pro28-amide

Reaction of 5-carboxyfluorescein with N-hydroxysuccinimide (NHS) and 1,3-dicyclohexylcarbodiimide (DCC) in DMF gave the corresponding NHS ester, which was then treated with ethylenediamine. The resulting amine was reacted with α-bromophenylacetic acid NHS ester to afford the desired α-bromo derivative 1 (see FIG. 6A). Treatment of 1 with 11-mercaptoundecanoic acid and $ET_3N$ in DMF provided the acid 2. Finally, conversion of 2 to its NHS ester followed by reaction with dioctadecylamine gave the target structure Pro28-amide, also referred to herein as Pro28.

EXAMPLE 2

Synthesis of Lipophilic eTag Pro29-amide

Reaction of 5-aminofluorescein with α-bromophenylacetyl chloride (prepared by treating α-bromophenylacetic acid with oxalyl chloride) gave the bromo compound 3 (see FIG. 6B), which was then reacted with 3-mercaptopropanoic acid and triethylamine in DMF. The resulting α-thioacid 4 was finally converted, as described above, to Pro29-amide.

EXAMPLE 3

Synthesis of Lipophilic eTag Pro36-amide

The synthesis of Pro36-amide, utilizing 5-carboxyfluorescein as starting material, was carried out as follows (see FIG. 6C). The fluorescein derivative was condensed with 1,10-diaminodecane, forming an amide linkage at the less hindered carboxyl group. The terminal amine was reacted with the NHS ester of Fmoc-protected glycine. The Fmoc-protected amine was then deprotected and reacted with the NHS ester of α-bromophenylacetic acid. Nucleophilic displacement of the bromide with 3-mercaptopropanoic acid, followed by NHS activation of the acid and condensation with dioctadecylamine, gave the product.

Novel compounds and the use of the compounds for labeling membranes have been disclosed. From the foregoing, it will be appreciated that, although specific embodiments of the invention have been described herein for purposes of illustration, various modifications may be made without deviating from the spirit and scope thereof.

We claim:

1. A compound of formula:

$$G\text{-}(L\text{-}E)_m$$

wherein:

G is a lipophilic moiety capable of incorporating into a lipid membrane;

L is a cleavable linker;

E is an electrophoretic tag; and m is an integer greater than 1 and less than 100, and wherein $G\text{-}(L\text{-}E)_m$ is selected from the group consisting of Pro28-amide, Pro29-amide, Pro33-amide, Pro34-amide, Pro35-amide, and Pro36-amide.

2. The compound of claim 1, wherein the lipid membrane is derived from a cell.

3. The compound of claim 1, wherein the lipid membrane is a liposome.

4. The compound of claim 1, wherein the cleavable linkage is an oxidation-labile linkage.

5. The compound of claim 1, wherein E is a fluorescent, water-soluble organic compound having a molecular weight in the range of from about 150 to 5000 daltons.

6. A mixture comprising a plurality of compounds having the formula:

$$G\text{-}(L\text{-}E)_m$$

wherein:

G is a lipophilic moiety capable of incorporating into a lipid membrane;

L is a cleavable linker;

E is an electrophoretic tag;

m is an integer greater than 1 and less than 100; and wherein E of each compound of the plurality is individually detectable, and wherein each $G\text{-}(L\text{-}E)_m$ is independently selected from the group consisting of Pro28-amide, Pro29-amide, Pro33-amide, Pro34-amide, Pro35-amide, and Pro36-amide.

7. The mixture of claim 6, wherein the cleavable linkage is an oxidation-labile linkage.

8. The mixture of claim 6, wherein E is a fluorescent, water-soluble organic compound having a molecular weight in the range of from about 150 to 2500 daltons.

9. Lipid membranes labeled with compounds of formula:

$$G\text{-}(L\text{-}E)_m$$

wherein:
G is a lipophilic moiety capable of incorporating into a lipid membrane;
L is a cleavable linker;
E is an electrophoretic tag; and
m is an integer greater than 1 and less than 100, and wherein $G\text{-}(L\text{-}E)_m$ is selected from the group consisting of Pro28-amide, Pro29-amide, Pro33-amide, Pro34-amide, Pro35-amide, and Pro36-amide.

10. The lipid membranes of claim 9, wherein the compounds are incorporated into the structure of the membranes.

11. The lipid membranes of claim 9, wherein the lipid membranes comprise individual cells.

12. The lipid membranes of claim 9, wherein the lipid membranes comprise a tissue comprised of multiple populations of cells.

13. The lipid membranes of claim 9, wherein the lipid membranes comprise liposomes.

* * * * *

SEQUENCE LISTING

<160> NUMBER OF SEQ ID NOS: 14

<210> SEQ ID NO 1
<211> LENGTH: 4
<212> TYPE: PRT
<213> ORGANISM: Artificial
<220> FEATURE:
<223> OTHER INFORMATION: Probe -continued

```
<400> SEQUENCE: 1

Ala Ala Pro Val
1

<210> SEQ ID NO 2
<211> LENGTH: 4
<212> TYPE: PRT
<213> ORGANISM: Artificial
<220> FEATURE:
<223> OTHER INFORMATION: Probe

<400> SEQUENCE: 2

Ala Ala Pro Phe
1

<210> SEQ ID NO 3
<211> LENGTH: 4
<212> TYPE: PRT
<213> ORGANISM: Artificial
<220> FEATURE:
<223> OTHER INFORMATION: Probe

<400> SEQUENCE: 3

Ala Ala Pro Met
1

<210> SEQ ID NO 4
<211> LENGTH: 4
<212> TYPE: PRT
<213> ORGANISM: Artificial
<220> FEATURE:
<223> OTHER INFORMATION: Probe

<400> SEQUENCE: 4

Ser Ala Ala Arg
1

<210> SEQ ID NO 5
<211> LENGTH: 5
<212> TYPE: PRT
<213> ORGANISM: Artificial
<220> FEATURE:
<223> OTHER INFORMATION: Probe

<400> SEQUENCE: 5

Ser Ser Ala Ala Arg
1               5

<210> SEQ ID NO 6
<211> LENGTH: 4
<212> TYPE: PRT
<213> ORGANISM: Artificial
<220> FEATURE:
<223> OTHER INFORMATION: Probe

<400> SEQUENCE: 6

Ser Ala Ala Asp
1

<210> SEQ ID NO 7
<211> LENGTH: 5
<212> TYPE: PRT
<213> ORGANISM: Artificial
<220> FEATURE:
<223> OTHER INFORMATION: Probe
```

```
<400> SEQUENCE: 7

Ser Ser Ala Ala Asp
1               5

<210> SEQ ID NO 8
<211> LENGTH: 7
<212> TYPE: PRT
<213> ORGANISM: Artificial
<220> FEATURE:
<223> OTHER INFORMATION: Probe
<220> FEATURE:
<221> NAME/KEY: misc_feature
<222> LOCATION: (7)..(7)
<223> OTHER INFORMATION: Xaa can be any naturally occurring amino acid

<400> SEQUENCE: 8

Arg Pro Lys Pro Leu Ala Xaa
1               5

<210> SEQ ID NO 9
<211> LENGTH: 8
<212> TYPE: PRT
<213> ORGANISM: Artificial
<220> FEATURE:
<223> OTHER INFORMATION: Probe
<220> FEATURE:
<221> NAME/KEY: misc_feature
<222> LOCATION: (8)..(8)
<223> OTHER INFORMATION: Xaa can be any naturally occurring amino acid

<400> SEQUENCE: 9

Ser Arg Pro Lys Pro Leu Ala Xaa
1               5

<210> SEQ ID NO 10
<211> LENGTH: 9
<212> TYPE: PRT
<213> ORGANISM: Artificial
<220> FEATURE:
<223> OTHER INFORMATION: Probe
<220> FEATURE:
<221> NAME/KEY: misc_feature
<222> LOCATION: (9)..(9)
<223> OTHER INFORMATION: Xaa can be any naturally occurring amino acid

<400> SEQUENCE: 10

Ser Ser Arg Pro Lys Pro Leu Ala Xaa
1               5

<210> SEQ ID NO 11
<211> LENGTH: 8
<212> TYPE: PRT
<213> ORGANISM: Artificial
<220> FEATURE:
<223> OTHER INFORMATION: Probe
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
```

```
-continued

<400> SEQUENCE: 11

Pro Xaa Gly Xaa His Ala Xaa Xaa
1               5

<210> SEQ ID NO 12
<211> LENGTH: 8
<212> TYPE: PRT
<213> ORGANISM: Artificial
<220> FEATURE:
<223> OTHER INFORMATION: Probe
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 12

Pro Leu Gly Leu Xaa Ala Arg Xaa
1               5

<210> SEQ ID NO 13
<211> LENGTH: 4
<212> TYPE: PRT
<213> ORGANISM: Artificial
<220> FEATURE:
<223> OTHER INFORMATION: Probe

<400> SEQUENCE: 13

Pro Leu Gly Leu
1

<210> SEQ ID NO 14
<211> LENGTH: 5
<212> TYPE: PRT
<213> ORGANISM: Artificial
<220> FEATURE:
<223> OTHER INFORMATION: Probe

<400> SEQUENCE: 14

Gly Pro Gln Gly Ile
1               5
```